United States Patent [19]
Bienkowski et al.

[11] Patent Number: 5,882,873
[45] Date of Patent: Mar. 16, 1999

[54] HUMAN DNA SEQUENCE ENCODING A KIDNEY ATP-DEPENDENT POTASSIUM CHANNEL

[75] Inventors: Michael Jerome Bienkowski, Portage; Vincent Edward Groppi, Jr., Kalamozoo, both of Mich.

[73] Assignee: Pharmacia & Upjohn Company, Kalamazoo, Mich.

[21] Appl. No.: 501,003

[22] PCT Filed: Feb. 15, 1994

[86] PCT No.: PCT/US94/01210

§ 371 Date: Aug. 9, 1995

§ 102(e) Date: Aug. 9, 1995

[87] PCT Pub. No.: WO94/19464

PCT Pub. Date: Sep. 1, 1994

Related U.S. Application Data

[63] Continuation-in-part of Ser. No. 122,797, Sep. 17, 1993, abandoned, which is a continuation-in-part of Ser. No. 21,616, Feb. 19, 1993, abandoned.

[51] Int. Cl.[6] .......................... C12N 15/12; C12N 15/63; C12N 5/10; G01N 33/50
[52] U.S. Cl. ..................... 435/7.21; 435/325; 435/320.1; 536/23.5
[58] Field of Search ................................. 435/7.21, 70.1, 435/240.1, 252.3, 254.11, 325, 320.1; 530/350; 536/23.5

[56] References Cited

U.S. PATENT DOCUMENTS

| | | | |
|---|---|---|---|
| 5,356,775 | 10/1994 | Herbert et al. | 435/6 |
| 5,670,335 | 9/1997 | Jan et al. | 435/29 |

FOREIGN PATENT DOCUMENTS

| | | |
|---|---|---|
| 92/02634 | 2/1992 | WIPO. |
| 92/02639 | 2/1992 | WIPO. |

OTHER PUBLICATIONS

Yano et al. Alternative splicing of human inwardly rectifying $K^+$ channel ROMK1 mRNA. Molecular Pharmacology. vol. 45, No. 5, pp. 854–860, May 1994.
George et al. Current methods in sequence comparison. In Macromolecular Sequencing and Synthesis, D. Schlesinger, ed., Alan R. Liss, Inc, NY. pp. 127–149, 1988.
Shiraga et al. Proceedings of the National Academy of Sciences, USA. vol. 89, No. 1, pp. 426–430, Jan. 1, 1992.
Hoyer. GenBank Accession No. M83248, Apr. 16, 1994.
Chandy, K. G., et al., *Science*, 247, pp. 973–975 (1990).
Lazdunski, M., *Cardiovascular Drugs and Therapy*, 6, pp. 313–319 (1992).
Bond, C.T., et al., *Receptors and Channels*, 2, pp. 183–191 (1994).
Takumi, T., et al., *J. Biol. Chem.*, 270, pp. 16339–16346 (1995).
Bredt, D. S., et al., *Proc. Natl. Acad. Sci. USA*, 92, pp. 6753–6757 (1995).

*Primary Examiner*—Lila Feisee
*Assistant Examiner*—Michael D. Pak
*Attorney, Agent, or Firm*—Thomas A. Wootton

[57] ABSTRACT

The present invention comprises human DNA compositions encoding proteins that confer potassium channel activity to membranes or recipient cell lines. The DNA compositions include structural genes coding for the potassium channel proteins, expression and replication plasmids or vectors containing the structural genes and host cells expressing those genes. Methods of screening compounds for potassium channel modulating activity are also described.

35 Claims, 37 Drawing Sheets

FIG. 1A

```
     ATGCCAACTGTTTATCTCTGCTCTGAACAGATCAGGGTGTTGACAGAAAG
248--+---------+---------+---------+---------+-------
     TACGGTTGACAAATAGAGACGAGACTTGTCTAGTCCCACAACTGTCTTTC

M  P  T  V  Y  L  C  S  E  Q  I  R  V  L  T  E  S

TATGTTCAAACATCTTCGGAAATGGGTCGTCACTCGCTTTTTTGGGCATT
   --+---------+---------+---------+---------+-------347
     ATACAAGTTTGTAGAAGCCTTTACCCAGCAGTGAGCGAAAAAACCCGTAA

M  F  K  H  L  R  K  W  V  V  T  R  F  F  G  H  S

CTCGGCAAAGAGCAAGGCTAGTCTCCAAAGATGGAAGGTGCAACATAGAA
348--+---------+---------+---------+---------+-------
     GAGCCGTTTCTCGTTCCGATCAGAGGTTTCTACCTTCCACGTTGTATCTT

R  Q  R  A  R  L  V  S  K  D  G  R  C  N  I  E

TTTGGCAATGTGGAGGCACAGTCAAGGTTTATATTCTTTGTGGACATCTG
   --+---------+---------+---------+---------+-------447
     AAACCGTTACACCTCCGTGTCAGTTCCAAATATAAGAAACACCTGTAGAC

F  G  N  V  E  A  Q  S  R  F  I  F  F  V  D  I  W

GACAACGGTACTTGACCTCAAGTGGAGATACAAAATGACCATTTTCATCA
448--+---------+---------+---------+---------+-------
     CTGTTGCCATGAACTGGAGTTCACCTCTATGTTTTACTGGTAAAAGTAGT

T  T  V  L  D  L  K  W  R  Y  K  M  T  I  F  I  T

CAGCCTTCTTGGGGAGTTGGTTTTTCTTTGGTCTCCTGTGGTATGCAGTA
   --+---------+---------+---------+---------+-------547
     GTCGGAAGAACCCCTCAACCAAAAAGAAACCAGAGGACACCATACGTCAT

A  F  L  G  S  W  F  F  F  G  L  L  W  Y  A  V

GCGTACATTCACAAAGACCTCCCGGAATTCCATCCTTCTGCCAATCACAC
548--+---------+---------+---------+---------+-------
     CGCATGTAAGTGTTTCTGGAGGGCCTTAAGGTAGGAAGACGGTTAGTGTG

A  Y  I  H  K  D  L  P  E  F  H  P  S  A  N  H  T

TCCCTGTGTGGAGAATATTAATGGCTTGACCTCAGCTTTTCTGTTTTCTC
   --+---------+---------+---------+---------+-------647
     AGGGACACACCTCTTATAATTACCGAACTGGAGTCGAAAAGACAAAAGAG

```
     TGGAGACTCAAGTGACCATTGGATATGGATTCAGGTGTGTGACAGAACAG
648--+---------+---------+---------+---------+-------
     ACCTCTGAGTTCACTGGTAACCTATACCTAAGTCCACACACTGTCTTGTC

E  T  Q  V  T  I  G  Y  G  F  R  C  V  T  E  Q

TGTGCCACTGCCATTTTTCTGCTTATCTTTCAGTCTATACTTGGAGTTAT
   --+---------+---------+---------+---------+-------747
     ACACGGTGACGGTAAAAAGACGAATAGAAAGTCAGATATGAACCTCAATA

C  A  T  A  I  F  L  L  I  F  Q  S  I  L  G  V  I

AATCAATTCTTTCATGTGTGGGGCCATCTTAGCCAAGATCTCCAGGCCCA
748--+---------+---------+---------+---------+-------
     TTAGTTAAGAAAGTACACACCCCGGTAGAATCGGTTCTAGAGGTCCGGGT

I  N  S  F  M  C  G  A  I  L  A  K  I  S  R  P  K

AAAAACGTGCCAAGACCATTACGTTCAGCAAGAACGCAGTGATCAGCAAA
   --+---------+---------+---------+---------+-------847
     TTTTTGCACGGTTCTGGTAATGCAAGTCGTTCTTGCGTCACTAGTCGTTT

K  R  A  K  T  I  T  F  S  K  N  A  V  I  S  K

CGGGGAGGGAAGCTTTGCCTCCTAATCCGAGTGGCTAATCTCAGGAAGAG
848--+---------+---------+---------+---------+-------
     GCCCCTCCCTTCGAAACGGAGGATTAGGCTCACCGATTAGAGTCCTTCTC

R  G  G  K  L  C  L  L  I  R  V  A  N  L  R  K  S

CCTTCTTATTGGCAGTCACATTTATGGAAAGCTTCTGAAGACCACAGTCA
   --+---------+---------+---------+---------+-------947
     GGAAGAATAACCGTCAGTGTAAATACCTTTCGAAGACTTCTGGTGTCAGT

L  L  I  G  S  H  I  Y  G  K  L  L  K  T  T  V  T

CTCCTGAAGGAGAGACCATTATTTTGGACCAGATCAATATCAACTTTGTA
948--+---------+---------+---------+---------+-------
     GAGGACTTCCTCTCTGGTAATAAAACCTGGTCTAGTTATAGTTGAAACAT

P  E  G  E  T  I  I  L  D  Q  I  N  I  N  F  V

GTTGACGCTGGGAATGAAAATTTATTCTTCATCTCCCCATTGACAATTTA
   --+---------+---------+---------+---------+-------1047
     CAACTGCGACCCTTACTTTTAAATAAGAAGTAGAGGGGTAACTGTTAAAT

```
         CCATGTCATTGATCACAACAGCCCTTTCTTCCACATGGCAGCGGAGACCC
1048 --+---------+---------+---------+---------+-------
         GGTACAGTAACTAGTGTTGTCGGGAAAGAAGGTGTACCGTCGCCTCTGGG

H  V  I  D  H  N  S  P  F  F  H  M  A  A  E  T  L

TTCTCCAGCAGGACTTTGAATTAGTGGTGTTTTTAGATGGCACAGTGGAG
     --+---------+---------+---------+---------+-------
         AAGAGGTCGTCCTGAAACTTAATCACCACAAAAATCTACCGTGTCACCTC

L  Q  Q  D  F  E  L  V  V  F  L  D  G  T  V  E

TCCACCAGTGCTACCTGCCAAGTCCGGACATCCTATGTCCCAGAGGAGGT
1148 --+---------+---------+---------+---------+-------
         AGGTGGTCACGATGGACGGTTCAGGCCTGTAGGATACAGGGTCTCCTCCA

S  T  S  A  T  C  Q  V  R  T  S  Y  V  P  E  E  V

GCTTTGGGGCTACCGTTTTGCTCCCATAGTATCCAAGACAAAGGAAGGGA
     --+---------+---------+---------+---------+-------
         CGAAACCCCGATGGCAAAACGAGGGTATCATAGGTTCTGTTTCCTTCCCT

L  W  G  Y  R  F  A  P  I  V  S  K  T  K  E  G  K

AATACCGAGTGGATTTCCATAACTTTAGCAAGACAGTGGAAGTGGAGACC
1248 --+---------+---------+---------+---------+-------
         TTATGGCTCACCTAAAGGTATTGAAATCGTTCTGTCACCTTCACCTCTGG

Y  R  V  D  F  H  N  F  S  K  T  V  E  V  E  T

CCTCACTGTGCCATGTGCCTTTATAATGAGAAAGATGTTAGAGCCAGGAT
     --+---------+---------+---------+---------+-------
         GGAGTGACACGGTACACGGAAATATTACTCTTTCTACAATCTCGGTCCTA

P  H  C  A  M  C  L  Y  N  E  K  D  V  R  A  R  M

GAAGAGAGGCTATGACAACCCCAACTTCATCTTGTCAGAAGTCAATGAAA
1348 --+---------+---------+---------+---------+-------
         CTTCTCTCCGATACTGTTGGGGTTGAAGTAGAACAGTCTTCAGTTACTTT

K  R  G  Y  D  N  P  N  F  I  L  S  E  V  N  E  T

CAGATGACACCAAAATGTAA
     --+---------+-------1417
         GTCTACTGTGGTTTTACATT

```
       ATGTTCAAACATCTTCGGAAATGGGTCGTCACTCGCTTTTTTGGGCATTC
391 --+---------+---------+---------+---------+-------
       TACAAGTTTGTAGAAGCCTTTACCCAGCAGTGAGCGAAAAAACCCGTAAG

M   F   K   H   L   R   K   W   V   V   T   R   F   F   G   H   S

TCGGCAAAGAGCAAGGCTAGTCTCCAAAGATGGAAGGTGCAACATAGAAT
    --+---------+---------+---------+---------+-------490
       AGCCGTTTCTCGTTCCGATCAGAGGTTTCTACCTTCCACGTTGTATCTTA

R   Q   R   A   R   L   V   S   K   D   G   R   C   N   I   E   F

TTGGCAATGTGGAGGCACAGTCAAGGTTTATATTCTTTGTGGACATCTGG
491 --+---------+---------+---------+---------+-------
       AACCGTTACACCTCCGTGTCAGTTCCAAATATAAGAAACACCTGTAGACC

G   N   V   E   A   Q   S   R   F   I   F   F   V   D   I   W

ACAACGGTACTTGACCTCAAGTGGAGATACAAAATGACCATTTTCATCAC
    --+---------+---------+---------+---------+-------590
       TGTTGCCATGAACTGGAGTTCACCTCTATGTTTTACTGGTAAAAGTAGTG

T   T   V   L   D   L   K   W   R   Y   K   M   T   I   F   I   T

AGCCTTCTTGGGGAGTTGGTTTTTCTTTGGTCTCCTGTGGTATGCAGTAG
591 --+---------+---------+---------+---------+-------
       TCGGAAGAACCCCTCAACCAAAAAGAAACCAGAGGACACCATACGTCATC

A   F   L   G   S   W   F   F   F   G   L   L   W   Y   A   V   A

CGTACATTCACAAAGACCTCCCGGAATTCCATCCTTCTGCCAATCACACT
    --+---------+---------+---------+---------+-------690
       GCATGTAAGTGTTTCTGGAGGGCCTTAAGGTAGGAAGACGGTTAGTGTGA

Y   I   H   K   D   L   P   E   F   H   P   S   A   N   H   T

CCCTGTGTGGAGAATATTAATGGCTTGACCTCAGCTTTTCTGTTTTCTCT
691 --+---------+---------+---------+---------+-------
       GGGACACACCTCTTATAATTACCGAACTGGAGTCGAAAAGACAAAAGAGA

P   C   V   E   N   I   N   G   L   T   S   A   F   L   F   S   L

GGAGACTCAAGTGACCATTGGATATGGATTCAGGTGTGTGACAGAACAGT
    --+---------+---------+---------+---------+-------790
       CCTCTGAGTTCACTGGTAACCTATACCTAAGTCCACACACTGTCTTGTCA

```
     GTGCCACTGCCATTTTTCTGCTTATCTTTCAGTCTATACTTGGAGTTATA
791--+---------+---------+---------+---------+-------
     CACGGTGACGGTAAAAAGACGAATAGAAAGTCAGATATGAACCTCAATAT
```

A  T  A  I  F  L  L  I  F  Q  S  I  L  G  V  I

```
   ATCAATTCTTTCATGTGTGGGGCCATCTTAGCCAAGATCTCCAGGCCCAA
   --+---------+---------+---------+---------+-------890
   TAGTTAAGAAAGTACACACCCCGGTAGAATCGGTTCTAGAGGTCCGGGTT
```

I  N  S  F  M  C  G  A  I  L  A  K  I  S  R  P  K

```
     AAAACGAGCCAAGACCATTACGTTCAGCAAGAACGCAGTGATCAGCAAAC
891--+---------+---------+---------+---------+-------
     TTTTGCTCGGTTCTGGTAATGCAAGTCGTTCTTGCGTCACTAGTCGTTTG
```

K  R  A  K  T  I  T  F  S  K  N  A  V  I  S  K  R

```
   GGGGAGGGAAGCTTTGCCTCCTAATCCGAGTGGCTAATCTCAGGAAGAGC
   --+---------+---------+---------+---------+-------990
   CCCCTCCCTTCGAAACGGAGGATTAGGCTCACCGATTAGAGTCCTTCTCG
```

G  G  K  L  C  L  L  I  R  V  A  N  L  R  K  S

```
     CTTCTTATTGGCAGTCACATTTATGGAAAGCTTCTGAAGACCACAGTCAC
991--+---------+---------+---------+---------+-------
     GAAGAATAACCGTCAGTGTAAATACCTTTCGAAGACTTCTGGTGTCAGTG
```

L  L  I  G  S  H  I  Y  G  K  L  L  K  T  T  V  T

```
   TCCTGAAGGAGAGACCATTATTTTGGACCAGATCAATATCAACTTTGTAG
   --+---------+---------+---------+---------+-------
   AGGACTTCCTCTCTGGTAATAAAACCTGGTCTAGTTATAGTTGAAACATC
```

P  E  G  E  T  I  I  L  D  Q  I  N  I  N  F  V  V

```
     TTGACGCTGGGAATGAAAATTTATTCTTCATCTCCCCATTGACAATTTAC
1091-+---------+---------+---------+---------+-------
     AACTGCGACCCTTACTTTTAAATAAGAAGTAGAGGGGTAACTGTTAAATG
```

D  A  G  N  E  N  L  F  F  I  S  P  L  T  I  Y

```
   CATGTCATTGATCACAACAGCCCTTTCTTCCACATGGCAGCGGAGACCCT
   --+---------+---------+---------+---------+-------1190
   GTACAGTAACTAGTGTTGTCGGGAAAGAAGGTGTACCGTCGCCTCTGGGA
```

```
     TCTCCAGCAGGACTTTGAATTAGTGGTGTTTTAGATGGCACAGTGGAGT
1191--+---------+---------+---------+---------+-------
     AGAGGTCGTCCTGAAACTTAATCACCACAAAATCTACCGTGTCACCTCA

L  Q  Q  D  F  E  L  V  V  F  L  D  G  T  V  E  S

CCACCAGTGCTACCTGCCAAGTCCGGACATCCTATGTCCCAGAGGAGGTG
     --+---------+---------+---------+---------+-------1290
     GGTGGTCACGATGGACGGTTCAGGCCTGTAGGATACAGGGTCTCCTCCAC

T  S  A  T  C  Q  V  R  T  S  Y  V  P  E  E  V

CTTTGGGGCTACCGTTTTGCTCCCATAGTATCCAAGACAAAGGAAGGGAA
1291--+---------+---------+---------+---------+-------
     GAAACCCCGATGGCAAAACGAGGGTATCATAGGTTCTGTTTCCTTCCCTT

L  W  G  Y  R  F  A  P  I  V  S  K  T  K  E  G  K

ATACCGAGTGGATTTCCATAACTTTAGCAAGACAGTGGAAGTGGAGACCC
     --+---------+---------+---------+---------+-------1390
     TATGGCTCACCTAAAGGTATTGAAATCGTTCTGTCACCTTCACCTCTGGG

Y  R  V  D  F  H  N  F  S  K  T  V  E  V  E  T  P

CTCACTGTGCCATGTGCCTTTATAATGAGAAAGATGTTAGAGCCAGGATG
1391--+---------+---------+---------+---------+-------
     GAGTGACACGGTACACGGAAATATTACTCTTTCTACAATCTCGGTCCTAC

H  C  A  M  C  L  Y  N  E  K  D  V  R  A  R  M

AAGAGAGGCTATGACAACCCCAACTTCATCTTGTCAGAAGTCAATGAAAC
     --+---------+---------+---------+---------+-------1490
     TTCTCTCCGATACTGTTGGGGTTGAAGTAGAACAGTCTTCAGTTACTTTG

K  R  G  Y  D  N  P  N  F  I  L  S  E  V  N  E  T

AGATGACACCAAAATGTAA
1491--+---------+------1509
     TCTACTGTGGTTTTACATT

```
    ATGTTCAAACATCTTCGGAAATGGGTCGTCACTCGCTTTTTTGGGCATTC
226 --+---------+---------+---------+---------+-------
    TACAAGTTTGTAGAAGCCTTTACCCAGCAGTGAGCGAAAAAACCCGTAAG

M  F  K  H  L  R  K  W  V  V  T  R  F  F  G  H  S

TCGGCAAAGAGCAAGGCTAGTCTCCAAAGATGGAAGGTGCAACATAGAAT
    --+---------+---------+---------+---------+-------325
    AGCCGTTTCTCGTTCCGATCAGAGGTTTCTACCTTCCACGTTGTATCTTA

R  Q  R  A  R  L  V  S  K  D  G  R  C  N  I  E  F

TTGGCAATGTGGAGGCACAGTCAAGGTTTATATTCTTTGTGGACATCTGG
326 --+---------+---------+---------+---------+-------
    AACCGTTACACCTCCGTGTCAGTTCCAAATATAAGAAACACCTGTAGACC

G  N  V  E  A  Q  S  R  F  I  F  F  V  D  I  W

ACAACGGTACTTGACCTCAAGTGGAGATACAAAATGACCATTTTCATCAC
    --+---------+---------+---------+---------+-------425
    TGTTGCCATGAACTGGAGTTCACCTCTATGTTTTACTGGTAAAAGTAGTG

T  T  V  L  D  L  K  W  R  Y  K  M  T  I  F  I  T

AGCCTTCTTGGGGAGTTGGTTTTTCTTTGGTCTCCTGTGGTATGCAGTAG
426 --+---------+---------+---------+---------+-------
    TCGGAAGAACCCCTCAACCAAAAGAAACCAGAGGACACCATACGTCATC

A  F  L  G  S  W  F  F  F  G  L  L  W  Y  A  V  A

CGTACATTCACAAAGACCTCCCGGAATTCCATCCTTCTGCCAATCACACT
    --+---------+---------+---------+---------+-------525
    GCATGTAAGTGTTTCTGGAGGGCCTTAAGGTAGGAAGACGGTTAGTGTGA

Y  I  H  K  D  L  P  E  F  H  P  S  A  N  H  T

CCCTGTGTGGAGAATATTAATGGCTTGACCTCAGCTTTTCTGTTTTCTCT
526 --+---------+---------+---------+---------+-------
    GGGACACACCTCTTATAATTACCGAACTGGAGTCGAAAAGACAAAAGAGA

P  C  V  E  N  I  N  G  L  T  S  A  F  L  F  S  L

GGAGACTCAAGTGACCATTGGATATGGATTCAGGTGTGTGACAGAACAGT
    --+---------+---------+---------+---------+-------625
    CCTCTGAGTTCACTGGTAACCTATACCTAAGTCCACACACTGTCTTGTCA

```
    GTGCCACTGCCATTTTTCTGCTTATCTTTCAGTCTATACTTGGAGTTATA
626 --+---------+---------+---------+---------+-------
    CACGGTGACGGTAAAAAGACGAATAGAAAGTCAGATATGAACCTCAATAT

A  T  A  I  F  L  L  I  F  Q  S  I  L  G  V  I

ATCAATTCTTTCATGTGTGGGGCCATCTTAGCCAAGATCTCCAGGCCCAA
    --+---------+---------+---------+---------+-------725
    TAGTTAAGAAAGTACACACCCCGGTAGAATCGGTTCTAGAGGTCCGGGTT

I  N  S  F  M  C  G  A  I  L  A  K  I  S  R  P  K

AAAACGTGCCAAGACCATTACGTTCAGCAAGAACGCAGTGATCAGCAAAC
726 --+---------+---------+---------+---------+-------
    TTTTGCACGGTTCTGGTAATGCAAGTCGTTCTTGCGTCACTAGTCGTTTG

K  R  A  K  T  I  T  F  S  K  N  A  V  I  S  K  R

GGGGAGGGAAGCTTTGCCTCCTAATCCGAGTGGCTAATCTCAGGAAGAGC
    --+---------+---------+---------+---------+-------825
    CCCCTCCCTTCGAAACGGAGGATTAGGCTCACCGATTAGAGTCCTTCTCG

G  G  K  L  C  L  L  I  R  V  A  N  L  R  K  S

CTTCTTATTGGCAGTCACATTTATGGAAAGCTTCTGAAGACCACAGTCAC
826 --+---------+---------+---------+---------+-------
    GAAGAATAACCGTCAGTGTAAATACCTTTCGAAGACTTCTGGTGTCAGTG

L  L  I  G  S  H  I  Y  G  K  L  L  K  T  T  V  T

TCCTGAAGGAGAGACCATTATTTTGGACCAGATCAATATCAACTTTGTAG
    --+---------+---------+---------+---------+-------925
    AGGACTTCCTCTCTGGTAATAAAACCTGGTCTAGTTATAGTTGAAACATC

P  E  G  E  T  I  I  L  D  Q  I  N  I  N  F  V  V

TTGACGCTGGGAATGAAAATTTATTCTTCATCTCCCCATTGACAATTTAC
926 --+---------+---------+---------+---------+-------
    AACTGCGACCCTTACTTTTAAATAAGAAGTAGAGGGGTAACTGTTAAATG

D  A  G  N  E  N  L  F  F  I  S  P  L  T  I  Y

CATGTCATTGATCACAACAGCCCTTTCTTCCACATGGCAGCGGAGACCCT
    --+---------+---------+---------+---------+-------1025
    GTACAGTAACTAGTGTTGTCGGGAAAGAAGGTGTACCGTCGCCTCTGGGA

```
      TCTCCAGCAGGACTTTGAATTAGTGGTGTTTTTAGATGGCACAGTGGAGT
1026--+---------+---------+---------+---------+-------
      AGAGGTCGTCCTGAAACTTAATCACCACAAAAATCTACCGTGTCACCTCA

L  Q  Q  D  F  E  L  V  V  F  L  D  G  T  V  E  S

CCACCAGTGCTACCTGCCAAGTCCGGACATCCTATGTCCCAGAGGAGGTG
    --+---------+---------+---------+---------+-------
      GGTGGTCACGATGGACGGTTCAGGCCTGTAGGATACAGGGTCTCCTCCAC

T  S  A  T  C  Q  V  R  T  S  Y  V  P  E  E  V

CTTTGGGGCTACCGTTTTGCTCCCATAGTATCCAAGACAAAGGAAGGGAA
1126--+---------+---------+---------+---------+-------
      GAAACCCCGATGGCAAAACGAGGGTATCATAGGTTCTGTTTCCTTCCCTT

L  W  G  Y  R  F  A  P  I  V  S  K  T  K  E  G  K

ATACCGAGTGGATTTCCATAACTTTAGCAAGACAGTGGAAGTGGAGACCC
    --+---------+---------+---------+---------+-------
      TATGGCTCACCTAAAGGTATTGAAATCGTTCTGTCACCTTCACCTCTGGG

Y  R  V  D  F  H  N  F  S  K  T  V  E  V  E  T  P

CTCACTGTGCCATGTGCCTTTATAATGAGAAAGATGTTAGAGCCAGGATG
1226--+---------+---------+---------+---------+-------
      GAGTGACACGGTACACGGAAATATTACTCTTTCTACAATCTCGGTCCTAC

H  C  A  M  C  L  Y  N  E  K  D  V  R  A  R  M

AAGAGAGGCTATGACAACCCCAACTTCATCTTGTCAGAAGTCAATGAAAC
    --+---------+---------+---------+---------+-------
      TTCTCTCCGATACTGTTGGGGTTGAAGTAGAACAGTCTTCAGTTACTTTG

K  R  G  Y  D  N  P  N  F  I  L  S  E  V  N  E  T

AGATGACACCAAAATGTAA
1326--+---------+------1344
      TCTACTGTGGTTTTACATT

```
     ATGTTCAAACATCTTCGGAAATGGGTCGTCACTCGCTTTTTTGGGCATTC
258 --+---------+---------+---------+---------+-------
     TACAAGTTTGTAGAAGTCTTTACCCAGCAGTGAGCGAAAAAACCCGTAAG

M  F  K  H  L  Q  K  W  V  V  T  R  F  F  G  H  S

TCGGCAAAGAGCAAGGCTAGTCTCCAAAGATGGAAGGTGCAACATAGAAT
    --+---------+---------+---------+---------+-------357
     AGCCGTTTCTCGTTCCGATCAGAGGTTTCTACCTTCCACGTTGTATCTTA

R  Q  R  A  R  L  V  S  K  D  G  R  C  N  I  E  F

TTGGCAATGTGGAGGCACAGTCAAGGTTTATATTCTTTGTGGACATCTGG
358 --+---------+---------+---------+---------+-------
     AACCGTTACACCTCCGTGTCAGTTCCAAATATAAGAAACACCTGTAGACC

G  N  V  E  A  Q  S  R  F  I  F  F  V  D  I  W

ACAACGGTACTTGACCTCAAGTGGAGATACAAAATGACCATTTTCATCAC
    --+---------+---------+---------+---------+-------457
     TGTTGCCATGAACTGGAGTTCACCTCTATGTTTTACTGGTAAAAGTAGTG

T  T  V  L  D  L  K  W  R  Y  K  M  T  I  F  I  T

AGCCTTCTTGGGGAGTTGGTTTTTCTTTGGTCTCCTGTGGTATGCAGTAG
458 --+---------+---------+---------+---------+-------
     TCGGAAGAACCCCTCAACCAAAAAGAAACCAGAGGACACCATACGTCATC

A  F  L  G  S  W  F  F  F  G  L  L  W  Y  A  V  A

CGTACATTCACAAAGACCTCCCGGAATTCCATCCTTCTGCCAATCACACT
    --+---------+---------+---------+---------+-------557
     GCATGTAAGTGTTTCTGGAGGGCCTTAAGGTAGGAAGACGGTTAGTGTGA

Y  I  H  K  D  L  P  E  F  H  P  S  A  N  H  T

CCCTGTGTGGAGAATATTAATGGCTTGACCTCAGCTTTTCTGTTTTCTCT
558 --+---------+---------+---------+---------+-------
     GGGACACACCTCTTATAATTACCGAACTGGAGTCGAAAAGACAAAAGAGA

P  C  V  E  N  I  N  G  L  T  S  A  F  L  F  S  L

GGAGACTCAAGTGACCATTGGATATGGATTCAGGTGTGTGACAGAACAGT
    --+---------+---------+---------+---------+-------657
     CCTCTGAGTTCACTGGTAACCTATACCTAAGTCCACACACTGTCTTGTCA

```
     GTGCCACTGCCATTTTTCTGCTTATCTTTCAGTCTATACTTGGAGTTATA
658--+---------+---------+---------+---------+-------
     CACGGTGACGGTAAAAGACGAATAGAAAGTCAGATATGAACCTCAATAT

A  T  A  I  F  L  L  I  F  Q  S  I  L  G  V  I

ATCAATTCTTTCATGTGTGGGGCCATCTTAGCCAAGATCTCCAGGCCCAA
   --+---------+---------+---------+---------+-------757
     TAGTTAAGAAAGTACACACCCCGGTAGAATCGGTTCTAGAGGTCCGGGTT

I  N  S  F  M  C  G  A  I  L  A  K  I  S  R  P  K

AAAACGTGCCAAGACCATTACGTTCAGCAAGAACGCAGTGATCAGCAAAC
758--+---------+---------+---------+---------+-------
     TTTTGCACGGTTCTGGTAATGCAAGTCGTTCTTGCGTCACTAGTCGTTTG

K  R  A  K  T  I  T  F  S  K  N  A  V  I  S  K  R

GGGGAGGGAAGCTTTGCCTCCTAATCCGAGTGGCTAATCTCAGGAAGAGC
   --+---------+---------+---------+---------+-------857
     CCCCTCCCTTCGAAACGGAGGATTAGGCTCACCGATTAGAGTCCTTCTCG

G  G  K  L  C  L  L  I  R  V  A  N  L  R  K  S

CTTCTTATTGGCAGTCACATTTATGGAAAGCTTCTGAAGACCACAGTCAC
858--+---------+---------+---------+---------+-------
     GAAGAATAACCGTCAGTGTAAATACCTTTCGAAGACTTCTGGTGTCAGTG

L  L  I  G  S  H  I  Y  G  K  L  L  K  T  T  V  T

TCCTGAAGGAGAGACCATTATTTTGGACCAGATCAATATCAACTTTGTAG
   --+---------+---------+---------+---------+-------957
     AGGACTTCCTCTCTGGTAATAAAACCTGGTCTAGTTATAGTTGAAACATC

P  E  G  E  T  I  I  L  D  Q  I  N  I  N  F  V  V

TTGACGCTGGGAATGAAAATTTATTCTTCATCTCCCCATTGACAATTTAC
958--+---------+---------+---------+---------+-------
     AACTGCGACCCTTACTTTTAAATAAGAAGTAGAGGGGTAACTGTTAAATG

D  A  G  N  E  N  L  F  F  I  S  P  L  T  I  Y

CATGTCATTGATCACAACAGCCCTTTCTTCCACATGGCAGCGGAGACCCT
   --+---------+---------+---------+---------+-------1057
     GTACAGTAACTAGTGTTGTCGGGAAAGAAGGTGTACCGTCGCCTCTGGGA

```
     TCTCCAGCAGGACTTTGAATTAGTGGTGTTTTTAGATGGCACAGTGGAGT
1058 --+---------+---------+---------+---------+-------
     AGAGGTCGTCCTGAAACTTAATCACCACAAAAATCTACCGTGTCACCTCA

L   Q   Q   D   F   E   L   V   V   F   L   D   G   T   V   E   S

CCACCAGTGCTACCTGCCAAGTCCGGACATCCTATGTCCCAGAGGAGGTG
     --+---------+---------+---------+---------+-------
     GGTGGTCACGATGGACGGTTCAGGCCTGTAGGATACAGGGTCTCCTCCAC

T   S   A   T   C   Q   V   R   T   S   Y   V   P   E   E   V

CTTTGGGGCTACCGTTTTGCTCCCATAGTATCCAAGACAAAGGAAGGGAA
1158 --+---------+---------+---------+---------+-------
     GAAACCCCGATGGCAAAACGAGGGTATCATAGGTTCTGTTTCCTTCCCTT

L   W   G   Y   R   F   A   P   I   V   S   K   T   K   E   G   K

ATACCGAGTGGATTTCCATAACTTTAGCAAGACAGTGGAAGTGGAGACCC
     --+---------+---------+---------+---------+-------
     TATGGCTCACCTAAAGGTATTGAAATCGTTCTGTCACCTTCACCTCTGGG

Y   R   V   D   F   H   N   F   S   K   T   V   E   V   E   T   P

CTCACTGTGCCATGTGCCTTTATAATGAGAAAGATGTTAGAGCCAGGATG
1258 --+---------+---------+---------+---------+-------
     GAGTGACACGGTACACGGAAATATTACTCTTTCTACAATCTCGGTCCTAC

H   C   A   M   C   L   Y   N   E   K   D   V   R   A   R   M

AAGAGAGGCTATGACAACCCCAACTTCATCTTGTCAGAAGTCAATGAAAC
     --+---------+---------+---------+---------+-------
     TTCTCTCCGATACTGTTGGGGTTGAAGTAGAACAGTCTTCAGTTACTTTG

K   R   G   Y   D   N   P   N   F   I   L   S   E   V   N   E   T

AGATGACACCAAAATGTAA
1358 --+---------+------1376
     TCTACTGTGGTTTTACATT

```
    ATGAATGCTTCCAGTCGGAATGTGTTTGACACGTTGATCAGGGTGTTGAC
31  --+---------+---------+---------+---------+-------
    TACTTACGAAGGTCAGCCTTACACAAACTGTGCAACTAGTCCCACAACTG

M  N  A  S  S  R  N  V  F  D  T  L  I  R  V  L  T

AGAAAGTATGTTCAAACATCTTCGGAAATGGGTCGTCACTCGCTTTTTTG
    --+---------+---------+---------+---------+-------130
    TCTTTCATACAAGTTTGTAGAAGCCTTTACCCAGCAGTGAGCGAAAAAAC

E  S  M  F  K  H  L  R  K  W  V  V  T  R  F  F  G

GGCATTCTCGGCAAAGAGCAAGGCTAGTCTCCAAAGATGGAAGGTGCAAC
131 --+---------+---------+---------+---------+-------
    CCGTAAGAGCCGTTTCTCGTTCCGATCAGAGGTTTCTACCTTCCACGTTG

H  S  R  Q  R  A  R  L  V  S  K  D  G  R  C  N

ATAGAATTTGGCAATGTGGAGGCACAGTCAAGGTTTATATTCTTTGTGGA
    --+---------+---------+---------+---------+-------230
    TATCTTAAACCGTTACACCTCCGTGTCAGTTCCAAATATAAGAAACACCT

I  E  F  G  N  V  E  A  Q  S  R  F  I  F  F  V  D

CATCTGGACAACGGTACTTGACCTCAAGTGGAGATACAAAATGACCATTT
231 --+---------+---------+---------+---------+-------
    GTAGACCTGTTGCCATGAACTGGAGTTCACCTCTATGTTTTACTGGTAAA

I  W  T  T  V  L  D  L  K  W  R  Y  K  M  T  I  F

TCATCACAGCCTTCTTGGGGAGTTGGTTTTTCTTTGGTCTCCTGTGGTAT
    --+---------+---------+---------+---------+-------330
    AGTAGTGTCGGAAGAACCCCTCAACCAAAAAGAAACCAGAGGACACCATA
         I  T  A  F  L  G  S  W  F  F  F  G  L  L  W  Y

GCAGTAGCGTACATTCACAAAGACCTCCCGGAATTCCATCCTTCTGCCAA
331 --+---------+---------+---------+---------+-------
    CGTCATCGCATGTAAGTGTTTCTGGAGGGCCTTAAGGTAGGAAGACGGTT

A  V  A  Y  I  H  K  D  L  P  E  F  H  P  S  A  N

TCACACTCCCTGTGTGGAGAATATTAATGGCTTGACCTCAGCTTTTCTGT
    --+---------+---------+---------+---------+-------430
    AGTGTGAGGGACACACCTCTTATAATTACCGAACTGGAGTCGAAAAGACA

```
     TTTCTCTGGAGACTCAAGTGACCATTGGATATGGATTCAGGTGTGTGACA
431--+---------+---------+---------+---------+-------
     AAAGAGACCTCTGAGTTCACTGGTAACCTATACCTAAGTCCACACACTGT

S   L   E   T   Q   V   T   I   G   Y   G   F   R   C   V   T

GAACAGTGTGCCACTGCCATTTTTCTGCTTATCTTTCAGTCTATACTTGG
   --+---------+---------+---------+---------+-------530
     CTTGTCACACGGTGACGGTAAAAAGACGAATAGAAAGTCAGATATGAACC

E   Q   C   A   T   A   I   F   L   L   I   F   Q   S   I   L   G

AGTTATAATCAATTCTTTCATGTGTGGGGCCATCTTAGCCAAGATCTCCA
531--+---------+---------+---------+---------+-------
     TCAATATTAGTTAAGAAAGTACACACCCCGGTAGAATCGGTTCTAGAGGT

V   I   I   N   S   F   M   C   G   A   I   L   A   K   I   S   R

GGCCCAAAAAACGTGCCAAGACCATTACGTTCAGCAAGAACGCAGTGATC
   --+---------+---------+---------+---------+-------630
     CCGGGTTTTTTGCACGGTTCTGGTAATGCAAGTCGTTCTTGCGTCACTAG

P   K   K   R   A   K   T   I   T   F   S   K   N   A   V   I

AGCAAACGGGGAGGGAAGCTTTGCCTCCTAATCCGAGTGGCTAATCTCAG
631--+---------+---------+---------+---------+-------
     TCGTTTGCCCCTCCCTTCGAAACGGAGGATTAGGCTCACCGATTAGAGTC

S   K   R   G   G   K   L   C   L   L   I   R   V   A   N   L   R

GAAGAGCCTTCTTATTGGCAGTCACATTTATGGAAAGCTTCTGAAGACCA
   --+---------+---------+---------+---------+-------730
     CTTCTCGGAAGAATAACCGTCAGTGTAAATACCTTTCGAAGACTTCTGGT

K   S   L   L   I   G   S   H   I   Y   G   K   L   L   K   T   T

CAGTCACTCCTGAAGGAGAGACCATTATTTTGGACCAGATCAATATCAAC
731--+---------+---------+---------+---------+-------
     GTCAGTGAGGACTTCCTCTCTGGTAATAAAACCTGGTCTAGTTATAGTTG

V   T   P   E   G   E   T   I   I   L   D   Q   I   N   I   N

TTTGTAGTTGACGCTGGGAATGAAAATTTATTCTTCATCTCCCCATTGAC
   --+---------+---------+---------+---------+-------830
     AAACATCAACTGCGACCCTTACTTTTAAATAAGAAGTAGAGGGGTAACTG

```
    AATTTACCATGTCATTGATCACAACAGCCCTTTCTTCCACATGGCAGCGG
831 --+---------+---------+---------+---------+-------
    TTAAATGGTACAGTAACTAGTGTTGTCGGGAAAGAAGGTGTACCGTCGCC

I  Y  H  V  I  D  H  N  S  P  F  F  H  M  A  A  E

AGACCCTTCTCCAGCAGGACTTTGAATTAGTGGTGTTTTTAGATGGCACA
    --+---------+---------+---------+---------+-------930
    TCTGGGAAGAGGTCGTCCTGAAACTTAATCACCACAAAAATCTACCGTGT

T  L  L  Q  Q  D  F  E  L  V  V  F  L  D  G  T

GTGGAGTCCACCAGTGCTACCTGCCAAGTCCGGACATCCTATGTCCCAGA
931 --+---------+---------+---------+---------+-------
    CACCTCAGGTGGTCACGATGGACGGTTCAGGCCTGTAGGATACAGGGTCT

V  E  S  T  S  A  T  C  Q  V  R  T  S  Y  V  P  E

GGAGGTGCTTTGGGGCTACCGTTTTGCTCCCATAGTATCCAAGACAAAGG
    --+---------+---------+---------+---------+-------
    CCTCCACGAAACCCCGATGGCAAAACGAGGGTATCATAGGTTCTGTTTCC

E  V  L  W  G  Y  R  F  A  P  I  V  S  K  T  K  E

AAGGGAAATACCGAGTGGATTTCCATAACTTTAGCAAGACAGTGGAAGTG
    --+---------+---------+---------+---------+-------
    TTCCCTTTATGGCTCACCTAAAGGTATTGAAATCGTTCTGTCACCTTCAC

G  K  Y  R  V  D  F  H  N  F  S  K  T  V  E  V

GAGACCCCTCACTGTGCCATGTGCCTTTATAATGAGAAAGATGTTAGAGC
    --+---------+---------+---------+---------+-------
    CTCTGGGGAGTGACACGGTACACGGAAATATTACTCTTTCTACAATCTCG

E  T  P  H  C  A  M  C  L  Y  N  E  K  D  V  R  A

CAGGATGAAGAGAGGCTATGACAACCCCAACTTCATCTTGTCAGAAGTCA
    --+---------+---------+---------+---------+-------
    GTCCTACTTCTCTCCGATACTGTTGGGGTTGAAGTAGAACAGTCTTCAGT

R  M  K  R  G  Y  D  N  P  N  F  I  L  S  E  V  N

ATGAAACAGATGACACCAAAATGTAA
    --+---------+---------+---1206
    TACTTTGTCTACTGTGGTTTTACATT

```
Romk1       MGASERSVFR  VLIRALTERM  FKHLRRWFIT  HIFGRSRQRA  RLVSKEGRCN
cDNA K8     MNASSRNVFD  TLIRVLTESM  FKHLRKWVVT  RFFGHSRQRA  RLVSKDGRCN
cDNA K11                         M  FKHLRKWVVT  RFFGHSRQRA  RLVSKDGRCN
cDNA K11p1                       M  FKHLRKWVVT  RFFGHSRQRA  RLVSKDGRCN
cDNA K26       MPTVYLCS  EQIRVLTESM  FKHLRKWVVT  RFFGHSRQRA  RLVSKDGRCN
cDNA K26p1                       M  FKHLRKWVVT  RFFGHSRQRA  RLVSKDGRCN Romk1       IEFGNVDAQS  RFIFFVDIWT  TVLDLKWRYK  MTVFITAFLG  SWFLFGLLWY
cDNA K8     IEFGNVEAQS  RFIFFVDIWT  TVLDLKWRYK  MTIFITAFLG  SWFFFGLLWY
cDNA K11    IEFGNVEAQS  RFIFFVDIWT  TVLDLKWRYK  MTIFITAFLG  SWFFFGLLWY
cDNA K11p1  IEFGNVEAQS  RFIFFVDIWT  TVLDLKWRYK  MTIFITAFLG  SWFFFGLLWY
cDNA K26    IEFGNVEAQS  RFIFFVDIWT  TVLDLKWRYK  MTIFITAFLG  SWFFFGLLWY
cDNAK26p1   IEFGNVEAQS  RFIFFVDIWT  TVLDLKWRYK  MTIFITAFLG  SWFFFGLLWY Romk1       VVAYVHKDLP  EFYPPDNRTP  CVENINGMTS  AFLFSLETQV  TIGYGFRFVT
cDNA K8     AVAYIHKDLP  EFHPSANHTP  CVENINGLTS  AFLFSLETQV  TIGYGFRCVT
cDNA K11    AVAYIHKDLP  EFHPSANHTP  CVENINGLTS  AFLFSLETQV  TIGYGFRCVT
cDNA K11p1  AVAYIHKDLP  EFHPSANHTP  CVENINGLTS  AFLFSLETQV  TIGYGFRCVT
cDNA K26    AVAYIHKDLP  EFHPSANHTP  CVENINGLTS  AFLFSLETQV  TIGYGFRCVT
cDNA K26p1  AVAYIHKDLP  EFHPSANHTP  CVENINGLTS  AFLFSLETQV  TIGYGFRCVT Romk1       EQCATAIFLL  IFQSILGVII  NSFMCGAILA  KISRPKKRAK  TITFSKNAVI
cDNA K8     EQCATAIFLL  IFQSILGVII  NSFMCGAILA  KISRPKKRAK  TITFSKNAVI
cDNA K11    EQCATAIFLL  IFQSILGVII  NSFMCGAILA  KISRPKKRAK  TITFSKNAVI
cDNA K11p1  EQCATAIFLL  IFQSILGVII  NSFMCGAILA  KISRPKKRAK  TITFSKNAVI
cDNA K26    EQCATAIFLL  IFQSILGVII  NSFMCGAILA  KISRPKKRAK  TITFSKNAVI
cDNA K26p1  EQCATAIFLL  IFQSILGVII  NSFMCGAILA  KISRPKKRAK  TITFSKNAVI Romk1       SKRGGKLCLL  IRVANLRKSL  LIGSHIYGKL  LKTTITPEGE  TIILDQTNIN
cDNAK8      SKRGGKLCLL  IRVANLRKSL  LIGSHIYGKL  LKTTITPEGE  TIILDQININ
cDNA K11    SKRGGKLCLL  IRVANLRKSL  LIGSHIYGKL  LKTTITPEGE  TIILDQININ
cDNA K11p1  SKRGGKLCLL  IRVANLRKSL  LIGSHIYGKL  LKTTITPEGE  TIILDQININ
cDNA K26    SKRGGKLCLL  IRVANLRKSL  LIGSHIYGKL  LKTTITPEGE  TIILDQININ
cDNA K26p1  SKRGGKLCLL  IRVANLRKSL  LIGSHIYGKL  LKTTITPEGE  TIILDQININ
```

FIG. 6B

```
Romk1      FVVDAGNENL  FFISPLTIYH  IIDHNSPFFH  MAAETLSQQD  FELVVFLDGT
cDNA K8    FVVDAGNENL  FFISPLTIYH  VIDHNSPFFH  MAAETLLQQD  FELVVFLDGT
cDNA K11   FVVDAGNENL  FFISPLTIYH  VIDHNSPFFH  MAAETLLQQD  FELVVFLDGT
cDNA K11p1 FVVDAGNENL  FFISPLTIYH  VIDHNSPFFH  MAAETLLQQD  FELVVFLDGT
cDNA K26   FVVDAGNENL  FFISPLTIYH  VIDHNSPFFH  MAAETLLQQD  FELVVFLDGT
cDNA K26p1 FVVDAGNENL  FFISPLTIYH  VIDHNSPFFH  MAAETLLQQD  FELVVFLDGT Romk1      VESTSATCQV  RTSYVPEEVL  WGYRFVPIVS  KTKEGKYRVD  FHNFGKTVEV
cDNA K8    VESTSATCQV  RTSYVPEEVL  WGYRFAPIVS  KTKEGKYRVD  FHNFGKTVEV
cDNA K11   VESTSATCQV  RTSYVPEEVL  WGYRFAPIVS  KTKEGKYRVD  FHNFGKTVEV
cDNA K11p1 VESTSATCQV  RTSYVPEEVL  WGYRFAPIVS  KTKEGKYRVD  FHNFGKTVEV
cDNA K26   VESTSATCQV  RTSYVPEEVL  WGYRFAPIVS  KTKEGKYRVD  FHNFGKTVEV
cDNA K26p1 VESTSATCQV  RTSYVPEEVL  WGYRFAPIVS  KTKEGKYRVD  FHNFGKTVEV
```

Romk1       ETPHCAMCLY NEKDARARMK RGYDNPNFVL SEVDETDDTQ M* (Seq.ID No.16)
cDNA K8     ETPHCAMCLY NEKDVRARMK RGYDNPNFIL SEVNETDDTK M* (Seq.ID No.13)
cDNA K11    ETPHCAMCLY NEKDVRARMK RGYDNPNFIL SEVNETDDTK M* (Seq.ID No.12)
cDNA K11p1  ETPHCAMCLY NEKDVRARMK RGYDNPNFIL SEVNETDDTK M* (Seq.ID No.12)
cDNA K26    ETPHCAMCLY NEKDVRARMK RGYDNPNFIL SEVNETDDTK M* (Seq.ID No.11)
cDNA K26p1  ETPHCAMCLY NEKDVRARMK RGYDNPNFIL SEVNETDDTK M* (Seq.ID No.12)

FIG.7A(1)
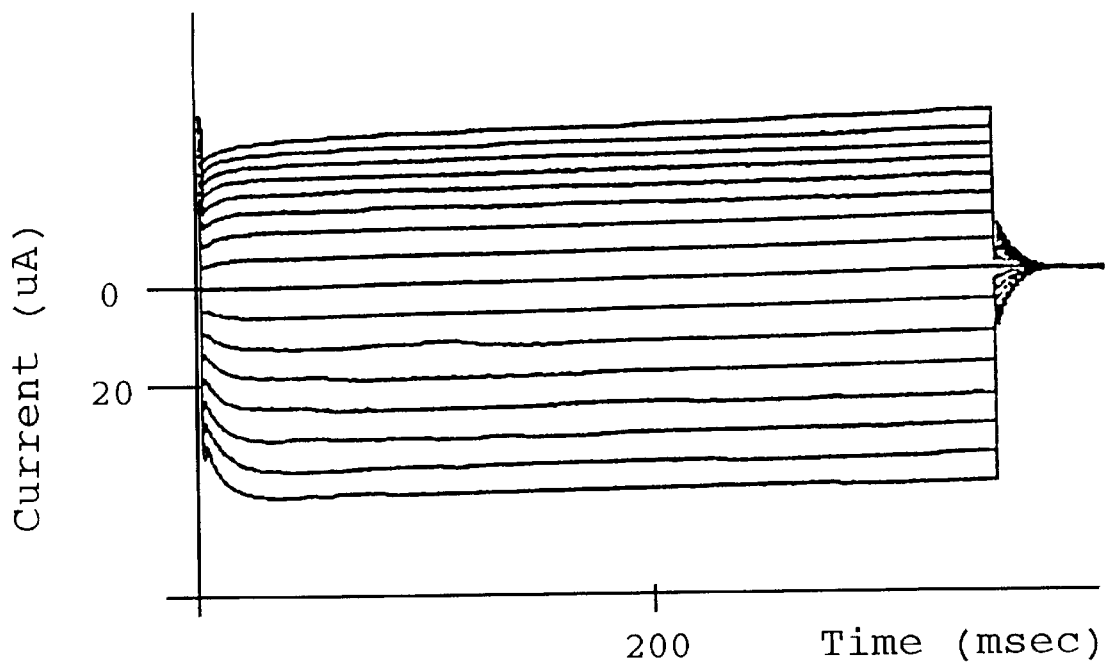
FIG.7A(2)
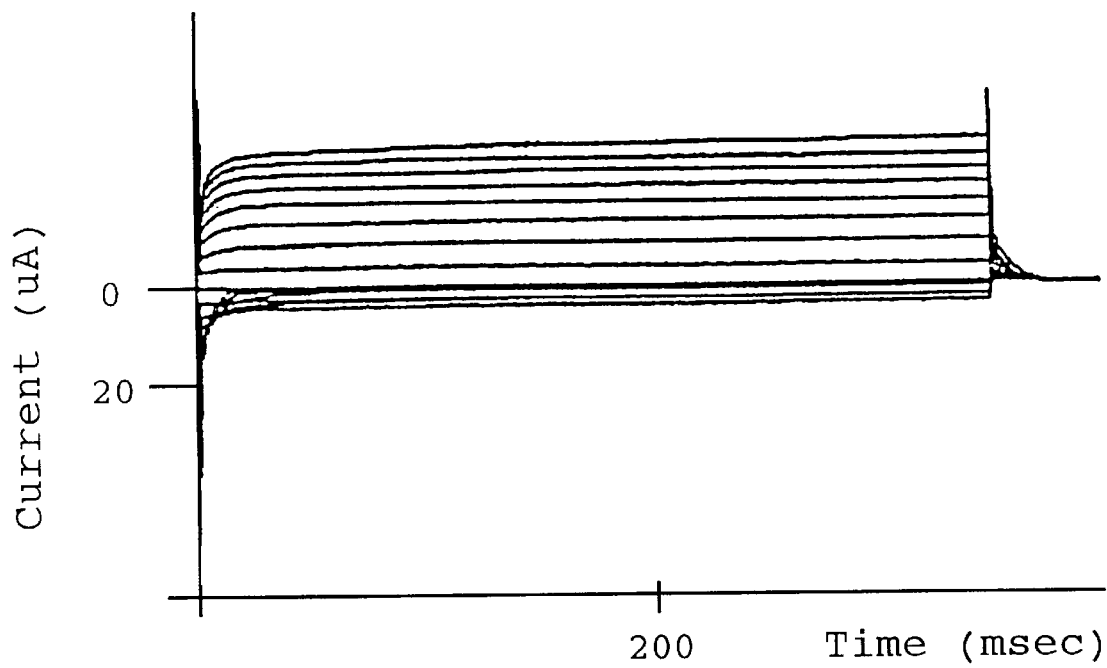

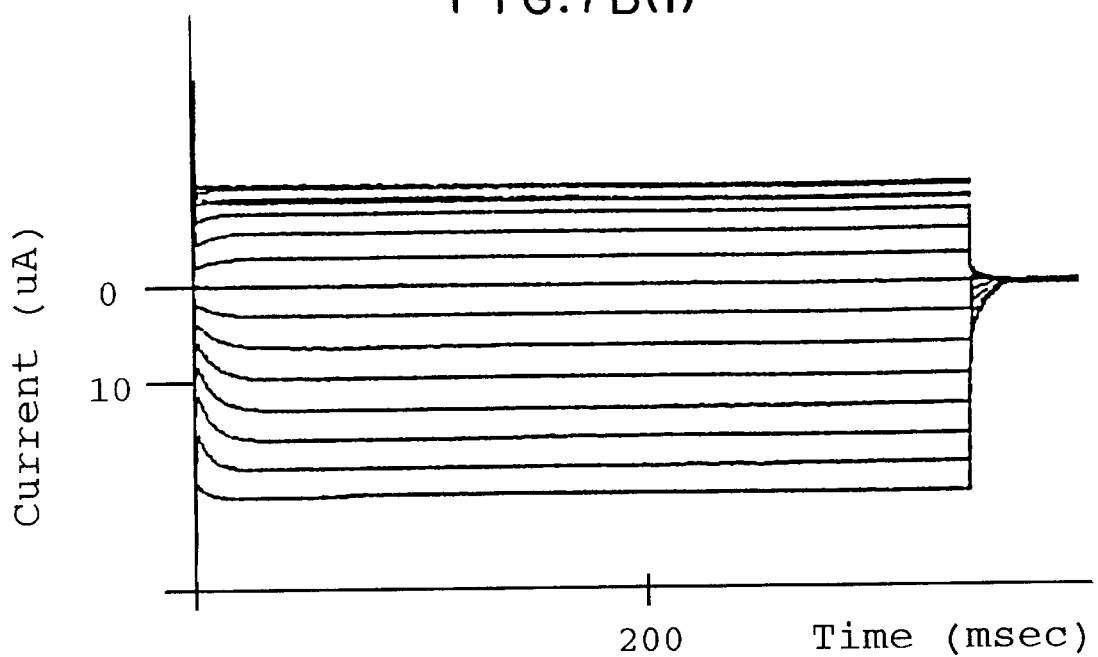
FIG.7B(1)
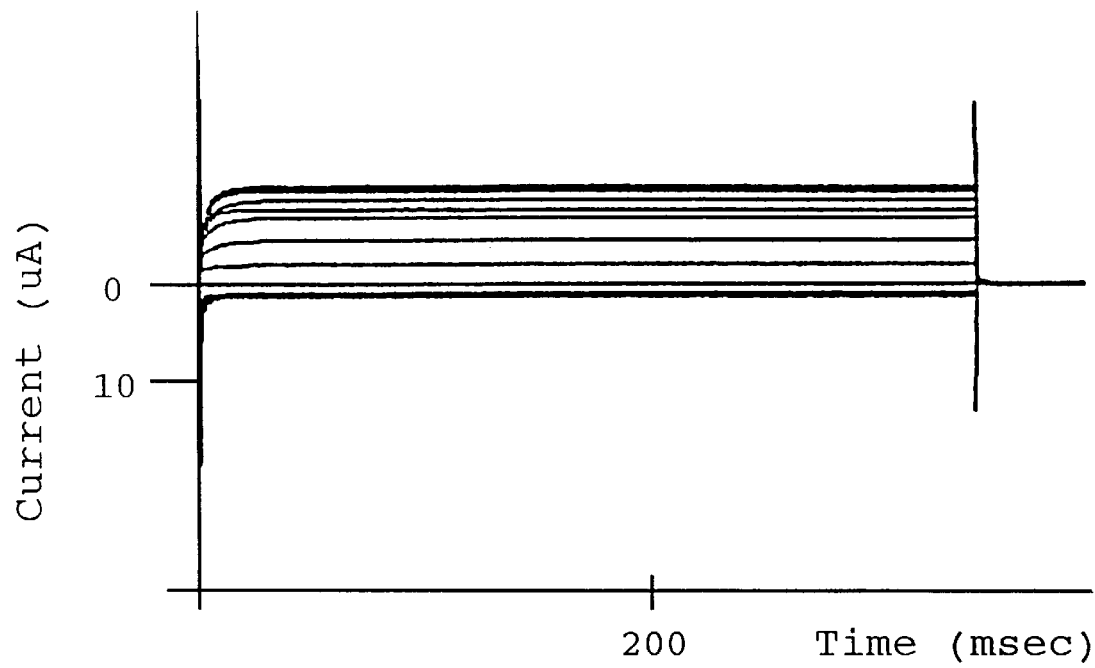
FIG.7B(2)

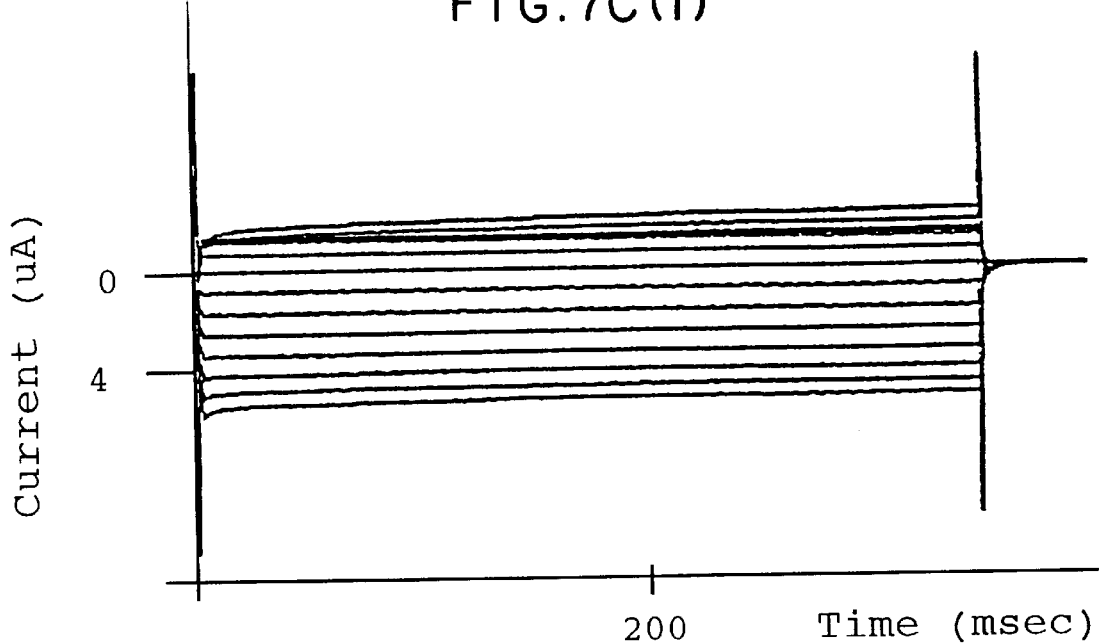
FIG.7C(1)
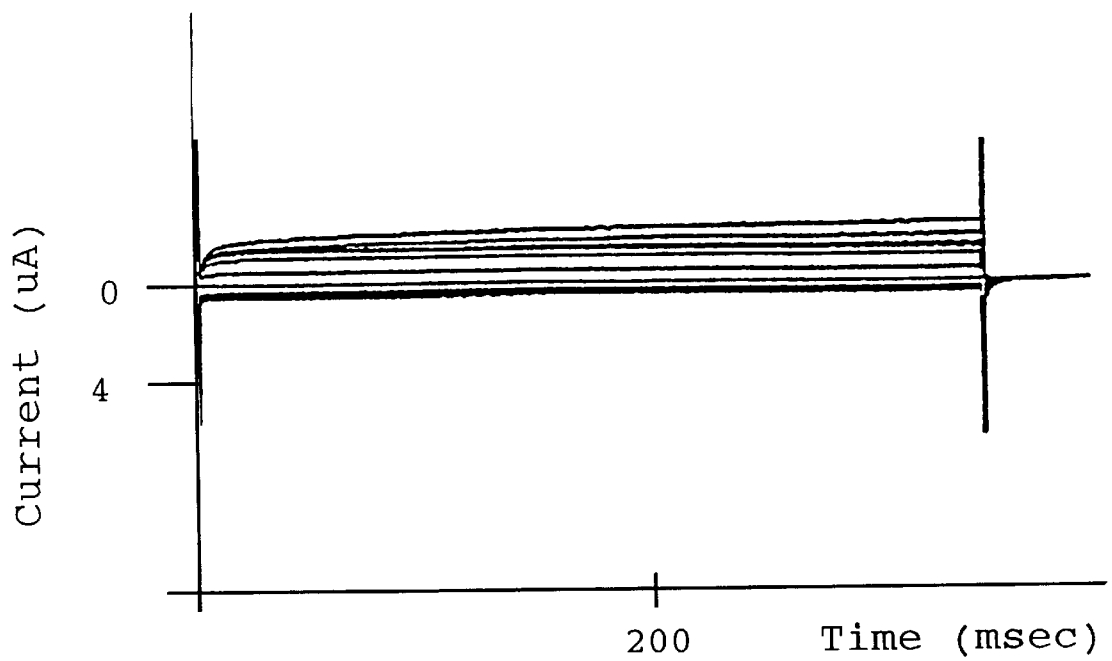
FIG.7C(2)

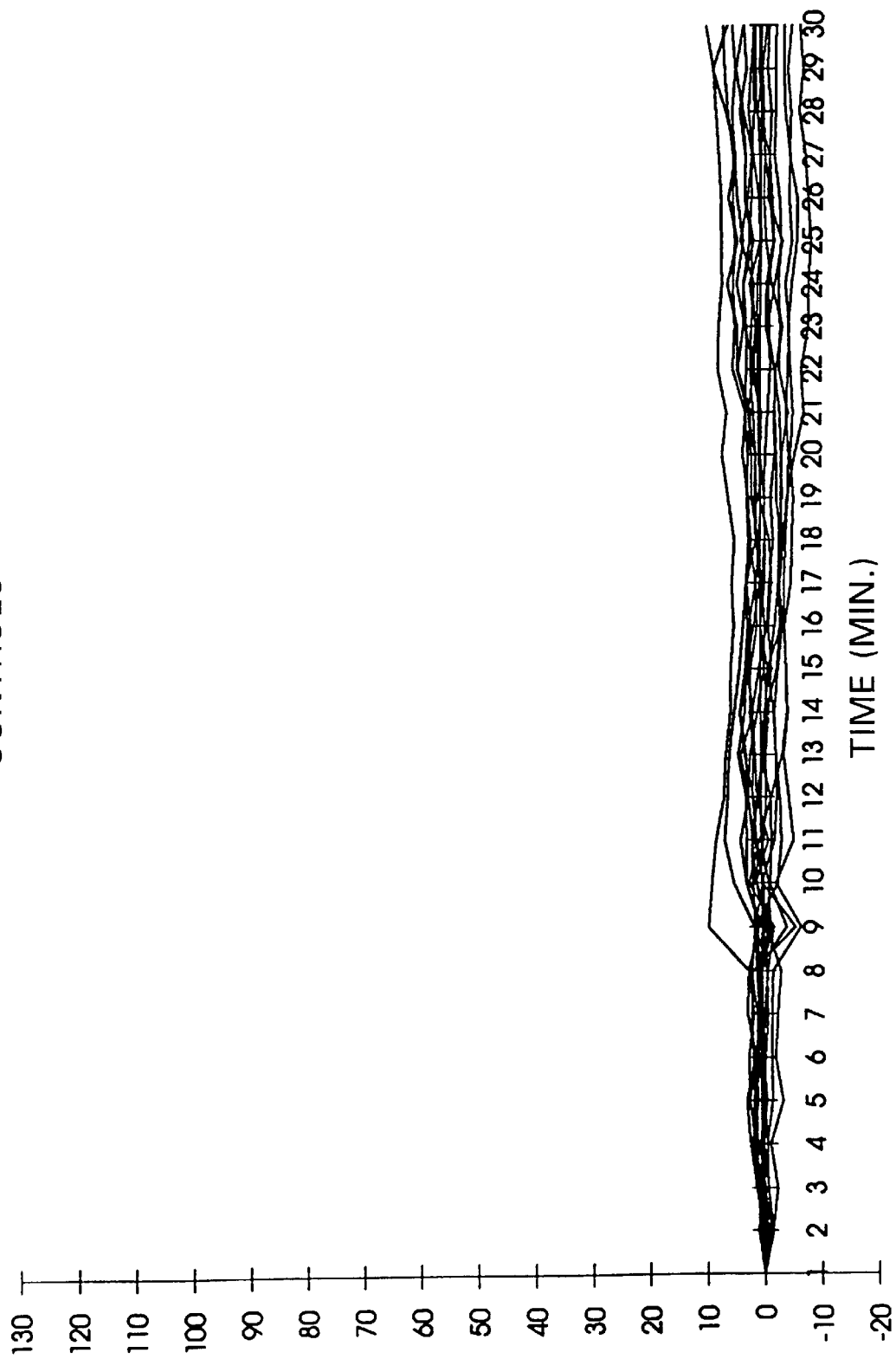

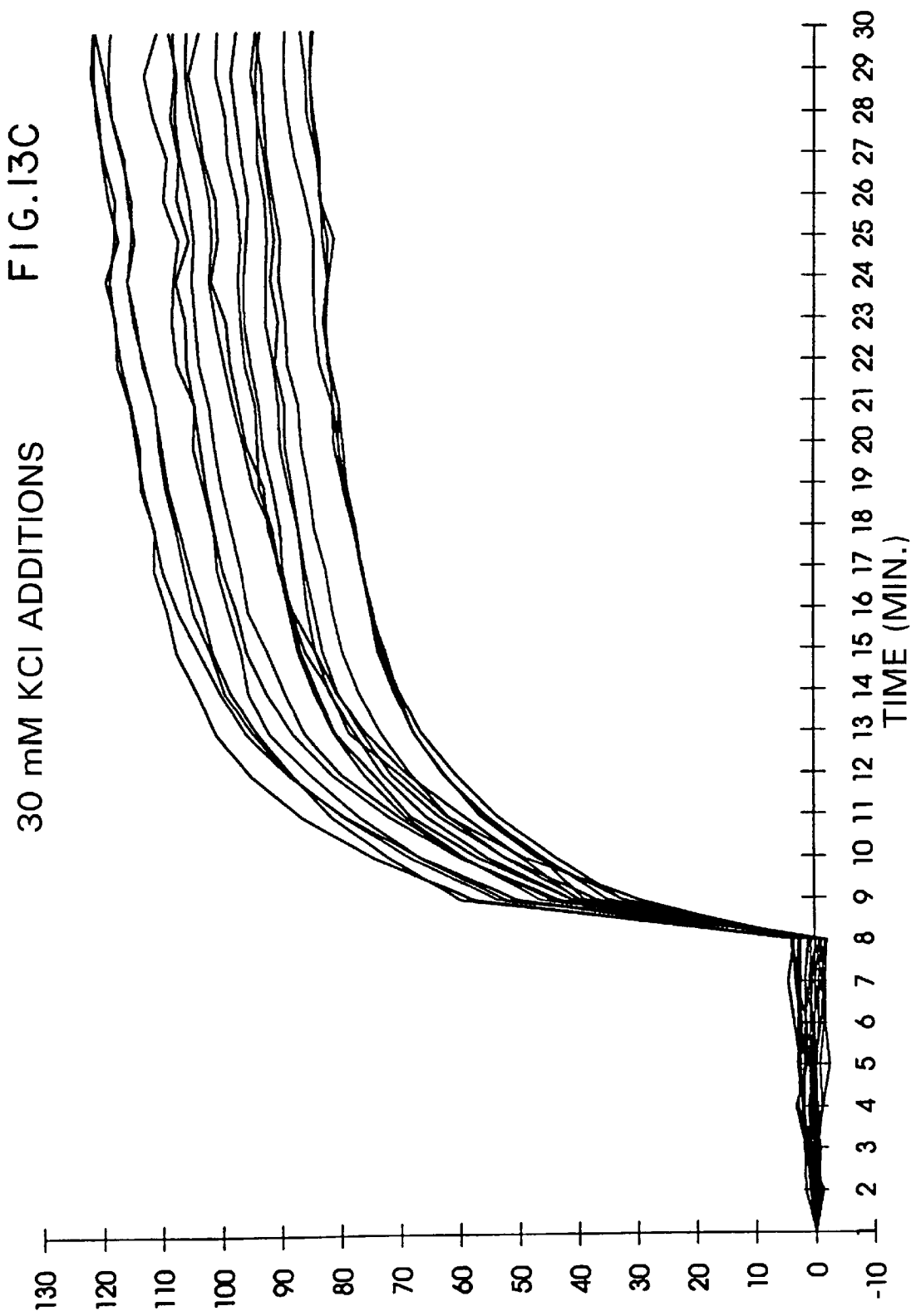

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 1740 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo sapiens ( v i i ) IMMEDIATE SOURCE:
    ( A ) LIBRARY: Human Kidney cDNA
    ( B ) CLONE: k26

( x i ) SEQUENCE DESCRIPTION: SEQ ID NO:1:

| | | | | | | |
|---|---|---|---|---|---|---|
| CGGGGGCCTC | GGGTACCCTC | ACCCAGCATA | TCCAAACTCT | TGCATCAAAG | GTGCAGGGAC | 60 |
| TTGCTCACAT | CGAGAATCTG | GTTGCTTTCT | TGGAGACCAA | GAAAATGAGT | TTTTGTTTCT | 120 |
| ACATTTACTC | CAGCAATCCA | TGAGGACTTT | ATAGGAATTT | TGCACCATTC | TGAATGGATA | 180 |
| CATTTGGATT | TCTCAACATT | TGTTCAGCTT | CCTAATGACT | GTTGTGACAA | TTGCTCTATA | 240 |
| CCAGTGAATG | CCAACTGTTT | ATCTCTGCTC | TGAACAGATC | AGGGTGTTGA | CAGAAAGTAT | 300 |
| GTTCAAACAT | CTTCGGAAAT | GGGTCGTCAC | TCGCTTTTTT | GGGCATTCTC | GGCAAAGAGC | 360 |
| AAGGCTAGTC | TCCAAAGATG | GAAGGTGCAA | CATAGAATTT | GGCAATGTGG | AGGCACAGTC | 420 |
| AAGGTTTATA | TTCTTTGTGG | ACATCTGGAC | AACGGTACTT | GACCTCAAGT | GGAGATACAA | 480 |
| AATGACCATT | TTCATCACAG | CCTTCTTGGG | GAGTTGGTTT | TTCTTTGGTC | TCCTGTGGTA | 540 |
| TGCAGTAGCG | TACATTCACA | AAGACCTCCC | GGAATTCCAT | CCTTCTGCCA | ATCACACTCC | 600 |
| CTGTGTGGAG | AATATTAATG | GCTTGACCTC | AGCTTTTCTG | TTTTCTCTGG | AGACTCAAGT | 660 |
| GACCATTGGA | TATGGATTCA | GGTGTGTGAC | AGAACAGTGT | GCCACTGCCA | TTTTCTGCT | 720 |
| TATCTTTCAG | TCTATACTTG | GAGTTATAAT | CAATTCTTTC | ATGTGTGGGG | CCATCTTAGC | 780 |
| CAAGATCTCC | AGGCCCAAAA | AACGAGCCAA | GACCATTACG | TTCAGCAAGA | ACGCAGTGAT | 840 |
| CAGCAAACGG | GGAGGGAAGC | TTTGCCTCCT | AATCCGAGTG | GCTAATCTCA | GGAAGAGCCT | 900 |
| TCTTATTGGC | AGTCACATTT | ATGGAAAGCT | TCTGAAGACC | ACAGTCACTC | CTGAAGGAGA | 960 |
| GACCATTATT | TTGGACCAGA | TCAATATCAA | CTTTGTAGTT | GACGCTGGGA | ATGAAAATTT | 1020 |
| ATTCTTCATC | TCCCCATTGA | CAATTTACCA | TGTCATTGAT | CACAACAGCC | CTTTCTTCCA | 1080 |
| CATGGCAGCG | GAGACCCTTC | TCCAGCAGGA | CTTTGAATTA | GTGGTGTTTT | TAGATGGCAC | 1140 |
| AGTGGAGTCC | ACCAGTGCTA | CCTGCCAAGT | CCGGACATCC | TATGTCCCAG | AGGAGGTGCT | 1200 |
| TTGGGGCTAC | CGTTTTGCTC | CCATAGTATC | CAAGACAAAG | GAAGGGAAAT | ACCGAGTGGA | 1260 |
| TTTCCATAAC | TTTAGCAAGA | CAGTGGAAGT | GGAGACCCCT | CACTGTGCCA | TGTGCCTTTA | 1320 |
| TAATGAGAAA | GATGTTAGAG | CCAGGATGAA | GAGAGGCTAT | GACAACCCCA | ACTTCATCTT | 1380 |
| GTCAGAAGTC | AATGAAACAG | ATGACACCAA | AATGTAACAG | TGGCTTTTCA | ACAGGAGTAA | 1440 |
| AGAAAGTCTC | TAAAGCTCCT | AGTACCTAGA | AGCATTATGA | AGCAGTCAAC | AATTTAGGGG | 1500 |
| TACGAAAGTA | GGATGAGAGC | CTTCAAAGTC | TACCAGCACA | AAGACCCCTG | AGCCCCGCAA | 1560 |
| TTGTGATCCC | ACAAGACATG | CATCTCCACA | AGGCTACTGT | ATTAGAACGT | GCAATGCATT | 1620 |
| TATATGAAAC | TGGTGTATGG | AAGACATAGG | TGCTCTCTTG | AAATCTTAAA | TATGATTATT | 1680 |
| TGAGCTCATA | TAAGGTGGAT | TGGAGCAGAT | AAAATTACCA | AAAGTTTCAT | GAACAGGCG | 1740 |

( 2 ) INFORMATION FOR SEQ ID NO:2:

( i ) SEQUENCE CHARACTERISTICS:
        ( A ) LENGTH: 1832 base pairs
        ( B ) TYPE: nucleic acid
        ( C ) STRANDEDNESS: single
        ( D ) TOPOLOGY: linear (i i) MOLECULE TYPE: cDNA (i i i) HYPOTHETICAL: NO (i v) ANTI-SENSE: NO (v i) ORIGINAL SOURCE:
    (A) ORGANISM: Homo sapiens (v i i) IMMEDIATE SOURCE:
    (A) LIBRARY: Human Kidney cDNA
    (B) CLONE: K26p (x i) SEQUENCE DESCRIPTION: SEQ ID NO:2:

```
TGGTTGCTTT  CTTGGAGACC  AAGAAAATGA  GTTTTTGTTT  CTACATTTAC  TCCAGCAATC    60
CATGAGGACT  TTATAGGAAT  TTTGCACCAT  TCTGAATGGA  TACATTTGGA  TTTCTCAACA   120
TTTGTTCAGC  TTCCTAATGA  CTGTTGTGAC  AATTGCTCTA  TACCAGTGAA  TGCCAACTGT   180
TTATCCCTGC  TCTGAACAGG  TTTCTTCTCT  ACTGTGCCTT  CATCCCCATC  CTGGGCCCTG   240
ACAAAGACAG  TGTGACAAGT  TCTGAGCCCC  ACAGGTGGAA  TCCCAAACCA  AGCAGCTCTT   300
GCTGGTCACC  CCAAGATCTA  CTTATACATG  AAGTTTTGAA  AATCATCTCC  TGAACCTCTT   360
CTGACAGAGA  TCAGGGTGTT  GACAGAAAGT  ATGTTCAAAC  ATCTTCGGAA  ATGGGTCGTC   420
ACTCGCTTTT  TTGGGCATTC  TCGGCAAAGA  GCAAGGCTAG  TCTCCAAAGA  TGGAAGGTGC   480
AACATAGAAT  TTGGCAATGT  GGAGGCACAG  TCAAGGTTTA  TATTCTTTGT  GGACATCTGG   540
ACAACGGTAC  TTGACCTCAA  GTGGAGATAC  AAAATGACCA  TTTTCATCAC  AGCCTTCTTG   600
GGGAGTTGGT  TTTTCTTTGG  TCTCCTGTGG  TATGCAGTAG  CGTACATTCA  CAAAGACCTC   660
CCGGAATTCC  ATCCTTCTGC  CAATCACACT  CCCTGTGTGG  AGAATATTAA  TGGCTTGACC   720
TCAGCTTTTC  TGTTTTCTCT  GGAGACTCAA  GTGACCATTG  GATATGGATT  CAGGTGTGTG   780
ACAGAACAGT  GTGCCACTGC  CATTTTTCTG  CTTATCTTTC  AGTCTATACT  TGGAGTTATA   840
ATCAATTCTT  TCATGTGTGG  GGCCATCTTA  GCCAAGATCT  CCAGGCCCAA  AAAACGAGCC   900
AAGACCATTA  CGTTCAGCAA  GAACGCAGTG  ATCAGCAAAC  GGGGAGGGAA  GCTTTGCCTC   960
CTAATCCGAG  TGGCTAATCT  CAGGAAGAGC  CTTCTTATTG  GCAGTCACAT  TTATGGAAAG  1020
CTTCTGAAGA  CCACAGTCAC  TCCTGAAGGA  GAGACCATTA  TTTTGGACCA  GATCAATATC  1080
AACTTTGTAG  TTGACGCTGG  GAATGAAAAT  TTATTCTTCA  TCTCCCCATT  GACAATTTAC  1140
CATGTCATTG  ATCACAACAG  CCCTTTCTTC  CACATGGCAG  CGGAGACCCT  TCTCCAGCAG  1200
GACTTTGAAT  TAGTGGTGTT  TTTAGATGGC  ACAGTGGAGT  CCACCAGTGC  TACCTGCCAA  1260
GTCCGGACAT  CCTATGTCCC  AGAGGAGGTG  CTTTGGGGCT  ACCGTTTTGC  TCCCATAGTA  1320
TCCAAGACAA  AGGAAGGGAA  ATACCGAGTG  GATTTCCATA  ACTTTAGCAA  GACAGTGGAA  1380
GTGGAGACCC  CTCACTGTGC  CATGTGCCTT  TATAATGAGA  AAGATGTTAG  AGCCAGGATG  1440
AAGAGAGGCT  ATGACAACCC  CAACTTCATC  TTGTCAGAAG  TCAATGAAAC  AGATGACACC  1500
AAAATGTAAC  AGTGGCTTTT  CAACAGGAGT  AAAGAAAGTC  TCTAAAGCTC  CTAGTACCTA  1560
GAAGCATTAT  GAAGCAGTCA  ACAATTTAGG  GGTACGAAAG  TAGGATGAGA  GCCTTCAAAG  1620
TCTACCAGCA  CAAAGACCCC  TGAGCCCCGC  AATTGTGATC  CCACAAGACA  TGCATCTCCA  1680
CAAGGCTACT  GTATTAGAAC  GTGCAATGCA  TTTATATGAA  ACTGGTGTAT  GGAAGACATA  1740
GGTGCTCTCT  TGAAATCTTA  AATATGATTA  TTTGAGCTCA  TATAAGGTGG  ATTGGAGCAG  1800
ATAAAATTAC  CAAAAGTTTC  ATGAACAGGC  CG                                  1832
```

(2) INFORMATION FOR SEQ ID NO:3:

(i) SEQUENCE CHARACTERISTICS:
  (A) LENGTH: 1671 base pairs
  (B) TYPE: nucleic acid
  (C) STRANDEDNESS: single
  (D) TOPOLOGY: linear (ii) MOLECULE TYPE: cDNA (iii) HYPOTHETICAL: NO (iv) ANTI-SENSE: NO (vi) ORIGINAL SOURCE:
  (A) ORGANISM: Homo sapiens (vii) IMMEDIATE SOURCE:
  (A) LIBRARY: Human Kidney cDNA
  (B) CLONE: K11

(xi) SEQUENCE DESCRIPTION: SEQ ID NO:3:

```
CGGGTTGCAT ACAGATGAGT TGGCAGCCGG TCTGAGCTGG CCCACAGACT CATAAAATCA      60
ACAGGGCCTC GGGTACCCTC ACCCAGCATA TCCAAACTCT TGCATCAAAG GTGCAGGGAC     120
TTGCTCACAT CGAGAATCTG GTTGCTTTCT TGGAGACCAA GAAAATGAGT TTTTGTTTCT     180
ACATTTACTC CAGCAATCCA TGAGATCAGG GTGTTGACAG AAAGTATGTT CAAACATCTT     240
CGGAAATGGG TCGTCACTCG CTTTTTTGGG CATTCTCGGC AAAGAGCAAG GCTAGTCTCC     300
AAAGATGGAA GGTGCAACAT AGAATTTGGC AATGTGGAGG CACAGTCAAG GTTTATATTC     360
TTTGTGGACA TCTGGACAAC GGTACTTGAC CTCAAGTGGA GATACAAAAT GACCATTTTC     420
ATCACAGCCT TCTTGGGGAG TTGGTTTTTC TTTGGTCTCC TGTGGTATGC AGTAGCGTAC     480
ATTCACAAAG ACCTCCCGGA ATTCCATCCT TCTGCCAATC ACACTCCCTG TGTGGAGAAT     540
ATTAATGGCT TGACCTCAGC TTTTCTGTTT CTCTGGAGA CTCAAGTGAC CATTGGATAT      600
GGATTCAGGT GTGTGACAGA ACAGTGTGCC ACTGCCATTT TTCTGCTTAT CTTTCAGTCT     660
ATACTTGGAG TTATAATCAA TTCTTTCATG TGTGGGGCCA TCTTAGCCAA GATCTCCAGG     720
CCCAAAAAAC GTGCCAAGAC CATTACGTTC AGCAAGAACG CAGTGATCAG CAAACGGGGA     780
GGGAAGCTTT GCCTCCTAAT CCGAGTGGCT AATCTCAGGA AGAGCCTTCT TATTGGCAGT     840
CACATTTATG GAAAGCTTCT GAAGACCACA GTCACTCCTG AAGGAGAGAC CATTATTTTG     900
GACCAGATCA ATATCAACTT TGTAGTTGAC GCTGGGAATG AAAATTTATT CTTCATCTCC     960
CCATTGACAA TTTACCATGT CATTGATCAC AACAGCCCTT TCTTCCACAT GGCAGCGGAG    1020
ACCCTTCTCC AGCAGGACTT TGAATTAGTG GTGTTTTTAG ATGGCACAGT GGAGTCCACC    1080
AGTGCTACCT GCCAAGTCCG GACATCCTAT GTCCAGAGG AGGTGCTTTG GGGCTACCGT     1140
TTTGCTCCCA TAGTATCCAA GACAAAGGAA GGGAAATACC GAGTGGATTT CCATAACTTT    1200
AGCAAGACAG TGGAAGTGGA GACCCCTCAC TGTGCCATGT GCCTTTATAA TGAGAAAGAT    1260
GTTAGAGCCA GGATGAAGAG AGGCTATGAC AACCCCAACT TCATCTTGTC AGAAGTCAAT    1320
GAAACAGATG ACACCAAAAT GTAACAGTGG CTTTTCAACA GGAGTAAAGC AAAGTCTCTA    1380
AAGCTCCTAG TACCTAGAAG CATTATGAAG CAGTCAACAA TTTAGGGGTA CGAAAGTAGG    1440
ATGAGAGCCT TCAAAGTCTA CCAGCACAAA GACCCCTGAG CCCCGCAATT GTGATCCCAC    1500
AAGACATGCA TCTCCACAAG GCTACTGTAT TAGAACGTGC AATGCATTTA TATGAAACTG    1560
GTGTATGGAA GACATAGGTG CTCTCTTGAA ATCTTAAATA TGATTATTTG AGCTCATATA    1620
AGGTGGATTG GAGCAGATAA AATTATCAAA AGTTTCATGA ACAGGCCCCC G             1671
```

(2) INFORMATION FOR SEQ ID NO:4:

(i) SEQUENCE CHARACTERISTICS:
　　(A) LENGTH: 1703 base pairs
　　(B) TYPE: nucleic acid
　　(C) STRANDEDNESS: single
　　(D) TOPOLOGY: linear (ii) MOLECULE TYPE: cDNA (iii) HYPOTHETICAL: NO (iv) ANTI-SENSE: NO (vi) ORIGINAL SOURCE:
　　(A) ORGANISM: Homo sapiens (vii) IMMEDIATE SOURCE:
　　(A) LIBRARY: Human Kidney cDNA
　　(B) CLONE: K11P (xi) SEQUENCE DESCRIPTION: SEQ ID NO:4:

```
TGGTTGCTTT CTTGGAGACC AAGAAAATGA GTTTTGTTT  CTACATTTAC TCCAGCAATC    60
CATGAGGTTT CTTCTCTACT GTGCCTTCAT CCCCATCCTG GGCCCTGACA AAGACAGTGT   120
GACAAGTTCT GAGCCCCACA GGTGGAATCC CAAACCAAGC AGCTCTTGCT GGTCACCCCA   180
AGATCTACTT ATACATGAAG TTTTGAAAAT CATCTCCTGA ACCTCTTCTG ACAGAGATCA   240
GGGTGTTGAC AGAAAGTATG TTCAAACATC TTCAGAAATG GGTCGTCACT CGCTTTTTG   300
GGCATTCTCG GCAAAGAGCA AGGCTAGTCT CCAAAGATGG AAGGTGCAAC ATAGAATTTG   360
GCAATGTGGA GGCACAGTCA AGGTTTATAT TCTTTGTGGA CATCTGGACA ACGGTACTTG   420
ACCTCAAGTG GAGATACAAA ATGACCATTT TCATCACAGC CTTCTTGGGG AGTTGGTTTT   480
TCTTTGGTCT CCTGTGGTAT GCAGTAGCGT ACATTCACAA AGACCTCCCG GAATTCCATC   540
CTTCTGCCAA TCACACTCCC TGTGTGGAGA ATATTAATGG CTTGACCTCA GCTTTTCTGT   600
TTTCTCTGGA GACTCAAGTG ACCATTGGAT ATGGATTCAG GTGTGTGACA GAACAGTGTG   660
CCACTGCCAT TTTTCTGCTT ATCTTTCAGT CTATACTTGG AGTTATAATC AATTCTTTCA   720
TGTGTGGGGC CATCTTAGCC AAGATCTCCA GGCCCAAAAA ACGTGCCAAG ACCATTACGT   780
TCAGCAAGAA CGCAGTGATC AGCAAACGGG GAGGGAAGCT TTGCCTCCTA ATCCGAGTGG   840
CTAATCTCAG GAAGAGCCTT CTTATTGGCA GTCACATTTA TGGAAAGCTT CTGAAGACCA   900
CAGTCACTCC TGAAGGAGAG ACCATTATTT TGGACCAGAT CAATATCAAC TTTGTAGTTG   960
ACGCTGGGAA TGAAAATTTA TTCTTCATCT CCCCATTGAC AATTTACCAT GTCATTGATC  1020
ACAACAGCCC TTTCTTCCAC ATGGCAGCGG AGACCCTTCT CCAGCAGGAC TTTGAATTAG  1080
TGGTGTTTTT AGATGGCACA GTGGAGTCCA CCAGTGCTAC CTGCCAAGTC CGGACATCCT  1140
ATGTCCCAGA GGAGGTGCTT TGGGGCTACC GTTTTGCTCC CATAGTATCC AAGACAAAGG  1200
AAGGGAAATA CCGAGTGGAT TTCCATAACT TTAGCAAGAC AGTGGAAGTG GAGACCCCTC  1260
ACTGTGCCAT GTGCCTTTAT AATGAGAAAG ATGTTAGAGC CAGGATGAAG AGAGGCTATG  1320
ACAACCCCAA CTTCATCTTG TCAGAAGTCA ATGAAACAGA TGACACCAAA ATGTAACAGT  1380
GGCTTTTCAA CAGGAGTAAA GCAAAGTCTC TAAAGCTCCT AGTACCTAGA AGCATTATGA  1440
AGCAGTCAAC AATTTAGGGG TACGAAAGTA GGATGAGAGC CTTCAAAGTC TACCAGCACA  1500
AAGACCCCTG AGCCCCGCAA TTGTGATCCC ACAAGACATG CATCTCCACA AGGCTACTGT  1560
ATTAGAACGT GCAATGCATT TATATGAAAC TGGTGTATGG AAGACATAGG TGCTCTCTTG  1620
AAATCTTAAA TATGATTATT TGAGCTCATA TAAGGTGGAT TGGAGCAGAT AAAATTATCA  1680
AAAGTTTCAT GAACAGGCCC CCG                                           1703
```

( 2 ) INFORMATION FOR SEQ ID NO:5:

( i ) SEQUENCE CHARACTERISTICS:
        ( A ) LENGTH: 1591 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( v i i ) IMMEDIATE SOURCE:
        ( A ) LIBRARY: Human Kidney cDNA
        ( B ) CLONE: K8

( x i ) SEQUENCE DESCRIPTION: SEQ ID NO:5:

```
ACCAGCACCA  CTTCCTTGCT  TTTTCCAGCC  ATGAATGCTT  CCAGTCGGAA  TGTGTTTGAC      60
ACGTTGATCA  GGGTGTTGAC  AGAAAGTATG  TTCAAACATC  TTCGGAAATG  GGTCGTCACT     120
CGCTTTTTTG  GGCATTCTCG  GCAAAGAGCA  AGGCTAGTCT  CCAAAGATGG  AAGGTGCAAC     180
ATAGAATTTG  GCAATGTGGA  GGCACAGTCA  AGTTTATAT   TCTTTGTGGA  CATCTGGACA     240
ACGGTACTTG  ACCTCAAGTG  GAGATACAAA  ATGACCATTT  TCATCACAGC  CTTCTTGGGG     300
AGTTGGTTTT  TCTTTGGTCT  CCTGTGGTAT  GCAGTAGCGT  ACATTCACAA  AGACCTCCCG     360
GAATTCCATC  CTTCTGCCAA  TCACACTCCC  TGTGTGGAGA  ATATTAATGG  CTTGACCTCA     420
GCTTTTCTGT  TTTCTCTGGA  GACTCAAGTG  ACCATTGGAT  ATGGATTCAG  GTGTGTGACA     480
GAACAGTGTG  CCACTGCCAT  TTTTCTGCTT  ATCTTTCAGT  CTATACTTGG  AGTTATAATC     540
AATTCTTTCA  TGTGTGGGGC  CATCTTAGCC  AAGATCTCCA  GGCCCAAAAA  ACGTGCCAAG     600
ACCATTACGT  TCAGCAAGAA  CGCAGTGATC  AGCAAACGGG  GAGGGAAGCT  TTGCCTCCTA     660
ATCCGAGTGG  CTAATCTCAG  GAAGAGCCTT  CTTATTGGCA  GTCACATTTA  TGGAAAGCTT     720
CTGAAGACCA  CAGTCACTCC  TGAAGGAGAG  ACCATTATTT  TGGACCAGAT  CAATATCAAC     780
TTTGTAGTTG  ACGCTGGGAA  TGAAAATTTA  TTCTTCATCT  CCCCATTGAC  AATTTACCAT     840
GTCATTGATC  ACAACAGCCC  TTTCTTCCAC  ATGGCAGCGG  AGACCCTTCT  CCAGCAGGAC     900
TTTGAATTAG  TGGTGTTTTT  AGATGGCACA  GTGGAGTCCA  CCAGTGCTAC  CTGCCAAGTC     960
CGGACATCCT  ATGTCCCAGA  GGAGGTGCTT  TGGGGCTACC  GTTTTGCTCC  CATAGTATCC    1020
AAGACAAAGG  AAGGGAAATA  CCGAGTGGAT  TTCCATAACT  TTAGCAAGAC  AGTGGAAGTG    1080
GAGACCCCTC  ACTGTGCCAT  GTGCCTTTAT  AATGAGAAAG  ATGTTAGAGC  CAGGATGAAG    1140
AGAGGCTATG  ACAACCCCAA  CTTCATCTTG  TCAGAAGTCA  ATGAAACAGA  TGACACCAAA    1200
ATGTAACAGT  GGCTTTTCAA  CGGGAGTAAA  GCAAAGTCTC  TAAAGCTCCT  AGTACCTAGA    1260
AGCATTATGA  AGCAGTCAAC  AATTTAGGGG  TACGAAAGTA  GGATGAGAGC  CTTCAAAGTC    1320
TACCAGCACA  AAGACCCCTG  AGCCCCGCAA  TTGTGATCCC  ACAAGACATG  CATCTCCACA    1380
AGGCTACTGT  ATTAGAACGT  GCAATGCATT  TATATGAAAC  TGGTGTATGG  AAGACATAGG    1440
TGCTCTCTTG  AAATCTTAAA  TATGATTATT  TGAGCTCATA  TAAGGTGGAT  TGGAGCAGAT    1500
AAAATTATCA  AAAGTTTCAT  GAACAGGCCA  AACAAAATAT  TTTTTAAAGT  TTCCTTAAAG    1560
AAGTTATGAA  CTTTAGAAAG  GATCAGGGCC  G                                    1591
```

( 2 ) INFORMATION FOR SEQ ID NO:6:

( i ) SEQUENCE CHARACTERISTICS:
   ( A ) LENGTH: 1170 base pairs
   ( B ) TYPE: nucleic acid
   ( C ) STRANDEDNESS: single
   ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
   ( A ) ORGANISM: Homo sapiens ( v i i ) IMMEDIATE SOURCE:
   ( A ) LIBRARY: Human Kidney cDNA
   ( B ) CLONE: K26

( x i ) SEQUENCE DESCRIPTION: SEQ ID NO:6:

| | | | | | |
|---|---|---|---|---|---|
| ATGCCAACTG | TTTATCTCTG | CTCTGAACAG | ATCAGGGTGT | TGACAGAAAG | TATGTTCAAA | 60
| CATCTTCGGA | AATGGGTCGT | CACTCGCTTT | TTTGGGCATT | CTCGGCAAAG | AGCAAGGCTA | 120
| GTCTCCAAAG | ATGGAAGGTG | CAACATAGAA | TTTGGCAATG | TGGAGGCACA | GTCAAGGTTT | 180
| ATATTCTTTG | TGGACATCTG | GACAACGGTA | CTTGACCTCA | AGTGGAGATA | CAAAATGACC | 240
| ATTTTCATCA | CAGCCTTCTT | GGGGAGTTGG | TTTTTCTTTG | GTCTCCTGTG | GTATGCAGTA | 300
| GCGTACATTC | ACAAAGACCT | CCCGGAATTC | CATCCTTCTG | CCAATCACAC | TCCCTGTGTG | 360
| GAGAATATTA | ATGGCTTGAC | CTCAGCTTTT | CTGTTTTCTC | TGGAGACTCA | AGTGACCATT | 420
| GGATATGGAT | TCAGGTGTGT | GACAGAACAG | TGTGCCACTG | CCATTTTTCT | GCTTATCTTT | 480
| CAGTCTATAC | TTGGAGTTAT | AATCAATTCT | TTCATGTGTG | GGCCATCTT | AGCCAAGATC | 540
| TCCAGGCCCA | AAAAACGAGC | CAAGACCATT | ACGTTCAGCA | AGAACGCAGT | GATCAGCAAA | 600
| CGGGGAGGGA | AGCTTTGCCT | CCTAATCCGA | GTGGCTAATC | TCAGGAAGAG | CCTTCTTATT | 660
| GGCAGTCACA | TTTATGGAAA | GCTTCTGAAG | ACCACAGTCA | CTCCTGAAGG | AGAGACCATT | 720
| ATTTGGACC | AGATCAATAT | CAACTTTGTA | GTTGACGCTG | GGAATGAAAA | TTTATTCTTC | 780
| ATCTCCCCAT | TGACAATTTA | CCATGTCATT | GATCACAACA | GCCCTTTCTT | CCACATGGCA | 840
| GCGGAGACCC | TTCTCCAGCA | GGACTTTGAA | TTAGTGGTGT | TTTTAGATGG | CACAGTGGAG | 900
| TCCACCAGTG | CTACCTGCCA | AGTCCGGACA | TCCTATGTCC | CAGAGGAGGT | GCTTTGGGGC | 960
| TACCGTTTTG | CTCCCATAGT | ATCCAAGACA | AAGGAAGGGA | AATACCGAGT | GGATTTCCAT | 1020
| AACTTTAGCA | AGACAGTGGA | AGTGGAGACC | CCTCACTGTG | CCATGTGCCT | TTATAATGAG | 1080
| AAAGATGTTA | GAGCCAGGAT | GAAGAGAGGC | TATGACAACC | CCAACTTCAT | CTTGTCAGAA | 1140
| GTCAATGAAA | CAGATGACAC | CAAAATGTAA | | | | 1170

( 2 ) INFORMATION FOR SEQ ID NO:7:

( i ) SEQUENCE CHARACTERISTICS:
   ( A ) LENGTH: 1119 base pairs
   ( B ) TYPE: nucleic acid
   ( C ) STRANDEDNESS: single
   ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
   ( A ) ORGANISM: Homo sapiens (vii) IMMEDIATE SOURCE:
    (A) LIBRARY: Human Kidney cDNA
    (B) CLONE: K26P (xi) SEQUENCE DESCRIPTION: SEQ ID NO:7:

| | | | | | |
|---|---|---|---|---|---|
| ATGTTCAAAC | ATCTTCGGAA | ATGGGTCGTC | ACTCGCTTTT | TTGGGCATTC | TCGGCAAAGA | 60 |
| GCAAGGCTAG | TCTCCAAAGA | TGGAAGGTGC | AACATAGAAT | TTGGCAATGT | GGAGGCACAG | 120 |
| TCAAGGTTTA | TATTCTTTGT | GGACATCTGG | ACAACGGTAC | TTGACCTCAA | GTGGAGATAC | 180 |
| AAAATGACCA | TTTTCATCAC | AGCCTTCTTG | GGGAGTTGGT | TTTTCTTTGG | TCTCCTGTGG | 240 |
| TATGCAGTAG | CGTACATTCA | CAAAGACCTC | CCGGAATTCC | ATCCTTCTGC | CAATCACACT | 300 |
| CCCTGTGTGG | AGAATATTAA | TGGCTTGACC | TCAGCTTTTC | TGTTTTCTCT | GGAGACTCAA | 360 |
| GTGACCATTG | GATATGGATT | CAGGTGTGTG | ACAGAACAGT | GTGCCACTGC | CATTTTTCTG | 420 |
| CTTATCTTTC | AGTCTATACT | TGGAGTTATA | ATCAATTCTT | TCATGTGTGG | GGCCATCTTA | 480 |
| GCCAAGATCT | CCAGGCCCAA | AAAACGTGCC | AAGACCATTA | CGTTCAGCAA | GAACGCAGTG | 540 |
| ATCAGCAAAC | GGGGAGGGAA | GCTTTGCCTC | CTAATCCGAG | TGGCTAATCT | CAGGAAGAGC | 600 |
| CTTCTTATTG | GCAGTCACAT | TTATGGAAAG | CTTCTGAAGA | CCACAGTCAC | TCCTGAAGGA | 660 |
| GAGACCATTA | TTTTGGACCA | GATCAATATC | AACTTTGTAG | TTGACGCTGG | GAATGAAAAT | 720 |
| TTATTCTTCA | TCTCCCCATT | GACAATTTAC | CATGTCATTG | ATCACAACAG | CCCTTTCTTC | 780 |
| CACATGGCAG | CGGAGACCCT | TCTCCAGCAG | GACTTTGAAT | TAGTGGTGTT | TTTAGATGGC | 840 |
| ACAGTGGAGT | CCACCAGTGC | TACCTGCCAA | GTCCGGACAT | CCTATGTCCC | AGAGGAGGTG | 900 |
| CTTTGGGGCT | ACCGTTTTGC | TCCCATAGTA | TCCAAGACAA | AGGAAGGGAA | ATACCGAGTG | 960 |
| GATTCCATA | ACTTAGCAA | GACAGTGGAA | GTGGAGACCC | CTCACTGTGC | CATGTGCCTT | 1020 |
| TATAATGAGA | AAGATGTTAG | AGCCAGGATG | AAGAGAGGCT | ATGACAACCC | CAACTTCATC | 1080 |
| TTGTCAGAAG | TCAATGAAAC | AGATGACACC | AAAATGTAA | | | 1119 |

(2) INFORMATION FOR SEQ ID NO:8:

(i) SEQUENCE CHARACTERISTICS:
      (A) LENGTH: 1119 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Homo sapiens (vii) IMMEDIATE SOURCE:
      (A) LIBRARY: Human Kidney cDNA
      (B) CLONE: K11

(xi) SEQUENCE DESCRIPTION: SEQ ID NO:8:

| | | | | | |
|---|---|---|---|---|---|
| ATGTTCAAAC | ATCTTCGGAA | ATGGGTCGTC | ACTCGCTTTT | TTGGGCATTC | TCGGCAAAGA | 60 |
| GCAAGGCTAG | TCTCCAAAGA | TGGAAGGTGC | AACATAGAAT | TTGGCAATGT | GGAGGCACAG | 120 |
| TCAAGGTTTA | TATTCTTTGT | GGACATCTGG | ACAACGGTAC | TTGACCTCAA | GTGGAGATAC | 180 |
| AAAATGACCA | TTTTCATCAC | AGCCTTCTTG | GGGAGTTGGT | TTTTCTTTGG | TCTCCTGTGG | 240 |
| TATGCAGTAG | CGTACATTCA | CAAAGACCTC | CCGGAATTCC | ATCCTTCTGC | CAATCACACT | 300 |
| CCCTGTGTGG | AGAATATTAA | TGGCTTGACC | TCAGCTTTTC | TGTTTTCTCT | GGAGACTCAA | 360 |

-continued

| | | | | | |
|---|---|---|---|---|---|
| GTGACCATTG | GATATGGATT | CAGGTGTGTG | ACAGAACAGT | GTGCCACTGC | CATTTTTCTG | 420
| CTTATCTTTC | AGTCTATACT | TGGAGTTATA | ATCAATTCTT | TCATGTGTGG | GGCCATCTTA | 480
| GCCAAGATCT | CCAGGCCCAA | AAAACGTGCC | AAGACCATTA | CGTTCAGCAA | GAACGCAGTG | 540
| ATCAGCAAAC | GGGGAGGGAA | GCTTTGCCTC | CTAATCCGAG | TGGCTAATCT | CAGGAAGAGC | 600
| CTTCTTATTG | GCAGTCACAT | TTATGGAAAG | CTTCTGAAGA | CCACAGTCAC | TCCTGAAGGA | 660
| GAGACCATTA | TTTTGGACCA | GATCAATATC | AACTTTGTAG | TTGACGCTGG | GAATGAAAAT | 720
| TTATTCTTCA | TCTCCCCATT | GACAATTTAC | CATGTCATTG | ATCACAACAG | CCCTTTCTTC | 780
| CACATGGCAG | CGGAGACCCT | TCTCCAGCAG | GACTTTGAAT | TAGTGGTGTT | TTTAGATGGC | 840
| ACAGTGGAGT | CCACCAGTGC | TACCTGCCAA | GTCCGGACAT | CCTATGTCCC | AGAGGAGGTG | 900
| CTTTGGGGCT | ACCGTTTTGC | TCCCATAGTA | TCCAAGACAA | AGGAAGGGAA | ATACCGAGTG | 960
| GATTTCCATA | ACTTTAGCAA | GACAGTGGAA | GTGGAGACCC | CTCACTGTGC | CATGTGCCTT | 1020
| TATAATGAGA | AAGATGTTAG | AGCCAGGATG | AAGAGAGGCT | ATGACAACCC | CAACTTCATC | 1080
| TTGTCAGAAG | TCAATGAAAC | AGATGACACC | AAAATGTAA | | | 1119

( 2 ) INFORMATION FOR SEQ ID NO:9:

( i ) SEQUENCE CHARACTERISTICS:
        ( A ) LENGTH: 1119 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( v i i ) IMMEDIATE SOURCE:
        ( A ) LIBRARY: Human Kidney cDNA
        ( B ) CLONE: K11P ( x i ) SEQUENCE DESCRIPTION: SEQ ID NO:9:

| | | | | | |
|---|---|---|---|---|---|
| ATGTTCAAAC | ATCTTCAGAA | ATGGGTCGTC | ACTCGCTTTT | TTGGGCATTC | TCGGCAAAGA | 60
| GCAAGGCTAG | TCTCCAAAGA | TGGAAGGTGC | AACATAGAAT | TTGGCAATGT | GGAGGCACAG | 120
| TCAAGGTTTA | TATTCTTTGT | GGACATCTGG | ACAACGGTAC | TTGACCTCAA | GTGGAGATAC | 180
| AAAATGACCA | TTTTCATCAC | AGCCTTCTTG | GGGAGTTGGT | TTTTCTTTGG | TCTCCTGTGG | 240
| TATGCAGTAG | CGTACATTCA | CAAAGACCTC | CCGGAATTCC | ATCCTTCTGC | CAATCACACT | 300
| CCCTGTGTGG | AGAATATTAA | TGGCTTGACC | TCAGCTTTTC | TGTTTTCTCT | GGAGACTCAA | 360
| GTGACCATTG | GATATGGATT | CAGGTGTGTG | ACAGAACAGT | GTGCCACTGC | CATTTTTCTG | 420
| CTTATCTTTC | AGTCTATACT | TGGAGTTATA | ATCAATTCTT | TCATGTGTGG | GGCCATCTTA | 480
| GCCAAGATCT | CCAGGCCCAA | AAAACGTGCC | AAGACCATTA | CGTTCAGCAA | GAACGCAGTG | 540
| ATCAGCAAAC | GGGGAGGGAA | GCTTTGCCTC | CTAATCCGAG | TGGCTAATCT | CAGGAAGAGC | 600
| CTTCTTATTG | GCAGTCACAT | TTATGGAAAG | CTTCTGAAGA | CCACAGTCAC | TCCTGAAGGA | 660
| GAGACCATTA | TTTTGGACCA | GATCAATATC | AACTTTGTAG | TTGACGCTGG | GAATGAAAAT | 720
| TTATTCTTCA | TCTCCCCATT | GACAATTTAC | CATGTCATTG | ATCACAACAG | CCCTTTCTTC | 780
| CACATGGCAG | CGGAGACCCT | TCTCCAGCAG | GACTTTGAAT | TAGTGGTGTT | TTTAGATGGC | 840
| ACAGTGGAGT | CCACCAGTGC | TACCTGCCAA | GTCCGGACAT | CCTATGTCCC | AGAGGAGGTG | 900

| | | | | | |
|---|---|---|---|---|---|
| CTTTGGGGCT | ACCGTTTTGC | TCCCATAGTA | TCCAAGACAA | AGGAAGGGAA | ATACCGAGTG | 960 |
| GATTTCCATA | ACTTTAGCAA | GACAGTGGAA | GTGGAGACCC | CTCACTGTGC | CATGTGCCTT | 1020 |
| TATAATGAGA | AAGATGTTAG | AGCCAGGATG | AAGAGAGGCT | ATGACAACCC | CAACTTCATC | 1080 |
| TTGTCAGAAG | TCAATGAAAC | AGATGACACC | AAAATGTAA | | | 1119 |

( 2 ) INFORMATION FOR SEQ ID NO:10:

( i ) SEQUENCE CHARACTERISTICS:
        ( A ) LENGTH: 1176 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( v i i ) IMMEDIATE SOURCE:
        ( A ) LIBRARY: Human Kidney cDNA
        ( B ) CLONE: K8

( x i ) SEQUENCE DESCRIPTION: SEQ ID NO:10:

| | | | | | |
|---|---|---|---|---|---|
| ATGAATGCTT | CCAGTCGGAA | TGTGTTTGAC | ACGTTGATCA | GGGTGTTGAC | AGAAAGTATG | 60 |
| TTCAAACATC | TTCGGAAATG | GGTCGTCACT | CGCTTTTTTG | GGCATTCTCG | GCAAAGAGCA | 120 |
| AGGCTAGTCT | CCAAAGATGG | AAGGTGCAAC | ATAGAATTTG | GCAATGTGGA | GGCACAGTCA | 180 |
| AGGTTTATAT | TCTTTGTGGA | CATCTGGACA | ACGGTACTTG | ACCTCAAGTG | GAGATACAAA | 240 |
| ATGACCATTT | TCATCACAGC | CTTCTTGGGG | AGTTGGTTTT | TCTTTGGTCT | CCTGTGGTAT | 300 |
| GCAGTAGCGT | ACATTCACAA | AGACCTCCCG | GAATTCCATC | CTTCTGCCAA | TCACACTCCC | 360 |
| TGTGTGGAGA | ATATTAATGG | CTTGACCTCA | GCTTTTCTGT | TTTCTCTGGA | GACTCAAGTG | 420 |
| ACCATTGGAT | ATGGATTCAG | GTGTGTGACA | GAACAGTGTG | CCACTGCCAT | TTTTCTGCTT | 480 |
| ATCTTTCAGT | CTATACTTGG | AGTTATAATC | AATTCTTTCA | TGTGTGGGGC | CATCTTAGCC | 540 |
| AAGATCTCCA | GGCCCAAAAA | ACGTGCCAAG | ACCATTACGT | TCAGCAAGAA | CGCAGTGATC | 600 |
| AGCAAACGGG | GAGGGAAGCT | TTGCCTCCTA | ATCCGAGTGG | CTAATCTCAG | GAAGAGCCTT | 660 |
| CTTATTGGCA | GTCACATTTA | TGGAAAGCTT | CTGAAGACCA | CAGTCACTCC | TGAAGGAGAG | 720 |
| ACCATTATTT | TGGACCAGAT | CAATATCAAC | TTTGTAGTTG | ACGCTGGGAA | TGAAAATTTA | 780 |
| TTCTTCATCT | CCCCATTGAC | AATTTACCAT | GTCATTGATC | ACAACAGCCC | TTTCTTCCAC | 840 |
| ATGGCAGCGG | AGACCCTTCT | CCAGCAGGAC | TTTGAATTAG | TGGTGTTTTT | AGATGGCACA | 900 |
| GTGGAGTCCA | CCAGTGCTAC | CTGCCAAGTC | CGGACATCCT | ATGTCCCAGA | GGAGGTGCTT | 960 |
| TGGGGCTACC | GTTTTGCTCC | CATAGTATCC | AAGACAAAGG | AAGGGAAATA | CCGAGTGGAT | 1020 |
| TTCCATAACT | TTAGCAAGAC | AGTGGAAGTG | GAGACCCCTC | ACTGTGCCAT | GTGCCTTTAT | 1080 |
| AATGAGAAAG | ATGTTAGAGC | CAGGATGAAG | AGAGGCTATG | ACAACCCCAA | CTTCATCTTG | 1140 |
| TCAGAAGTCA | ATGAAACAGA | TGACACCAAA | ATGTAA | | | 1176 |

( 2 ) INFORMATION FOR SEQ ID NO:11:

( i ) SEQUENCE CHARACTERISTICS:
        ( A ) LENGTH: 389 amino acids
        ( B ) TYPE: amino acid
        ( C ) STRANDEDNESS: single
        ( D ) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
    (A) ORGANISM: Homo sapiens (vii) IMMEDIATE SOURCE:
    (B) CLONE: K26

(xi) SEQUENCE DESCRIPTION: SEQ ID NO:11:

```
Met Pro Thr Val Tyr Leu Cys Ser Glu Gln Ile Arg Val Leu Thr Glu
1               5                   10                  15

Ser Met Phe Lys His Leu Arg Lys Trp Val Val Thr Arg Phe Phe Gly
                20                  25                  30

His Ser Arg Gln Arg Ala Arg Leu Val Ser Lys Asp Gly Arg Cys Asn
            35                  40                  45

Ile Glu Phe Gly Asn Val Glu Ala Gln Ser Arg Phe Ile Phe Phe Val
        50                  55                  60

Asp Ile Trp Thr Thr Val Leu Asp Leu Lys Trp Arg Tyr Lys Met Thr
65                  70                  75                  80

Ile Phe Ile Thr Ala Phe Leu Gly Ser Trp Phe Phe Gly Leu Leu
                85                  90                  95

Trp Tyr Ala Val Ala Tyr Ile His Lys Asp Leu Pro Glu Phe His Pro
            100                 105                 110

Ser Ala Asn His Thr Pro Cys Val Glu Asn Ile Asn Gly Leu Thr Ser
            115                 120                 125

Ala Phe Leu Phe Ser Leu Glu Thr Gln Val Thr Ile Gly Tyr Gly Phe
    130                 135                 140

Arg Cys Val Thr Glu Gln Cys Ala Thr Ala Ile Phe Leu Leu Ile Phe
145                 150                 155                 160

Gln Ser Ile Leu Gly Val Ile Ile Asn Ser Phe Met Cys Gly Ala Ile
                165                 170                 175

Leu Ala Lys Ile Ser Arg Pro Lys Lys Arg Ala Lys Thr Ile Thr Phe
            180                 185                 190

Ser Lys Asn Ala Val Ile Ser Lys Arg Gly Gly Lys Leu Cys Leu Leu
        195                 200                 205

Ile Arg Val Ala Asn Leu Arg Lys Ser Leu Leu Ile Gly Ser His Ile
    210                 215                 220

Tyr Gly Lys Leu Leu Lys Thr Thr Val Thr Pro Glu Gly Glu Thr Ile
225                 230                 235                 240

Ile Leu Asp Gln Ile Asn Ile Asn Phe Val Val Asp Ala Gly Asn Glu
                245                 250                 255

Asn Leu Phe Phe Ile Ser Pro Leu Thr Ile Tyr His Val Ile Asp His
            260                 265                 270

Asn Ser Pro Phe Phe His Met Ala Ala Glu Thr Leu Leu Gln Gln Asp
        275                 280                 285

Phe Glu Leu Val Val Phe Leu Asp Gly Thr Val Glu Ser Thr Ser Ala
    290                 295                 300

Thr Cys Gln Val Arg Thr Ser Tyr Val Pro Glu Glu Val Leu Trp Gly
305                 310                 315                 320

Tyr Arg Phe Ala Pro Ile Val Ser Lys Thr Lys Glu Gly Lys Tyr Arg
                325                 330                 335
```

```
Val  Asp  Phe  His  Asn  Phe  Ser  Lys  Thr  Val  Glu  Val  Glu  Thr  Pro  His
               340                      345                      350

Cys  Ala  Met  Cys  Leu  Tyr  Asn  Glu  Lys  Asp  Val  Arg  Ala  Arg  Met  Lys
               355                      360                      365

Arg  Gly  Tyr  Asp  Asn  Pro  Asn  Phe  Ile  Leu  Ser  Glu  Val  Asn  Glu  Thr
     370                      375                      380

Asp  Asp  Thr  Lys  Met
385
```

(2) INFORMATION FOR SEQ ID NO:12:

(i) SEQUENCE CHARACTERISTICS:
        (A) LENGTH: 372 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Homo sapiens (vii) IMMEDIATE SOURCE:
        (B) CLONE: K26P, K11, K11P (xi) SEQUENCE DESCRIPTION: SEQ ID NO:12:

```
Met  Phe  Lys  His  Leu  Arg  Lys  Trp  Val  Val  Thr  Arg  Phe  Phe  Gly  His
1                   5                        10                      15

Ser  Arg  Gln  Arg  Ala  Arg  Leu  Val  Ser  Lys  Asp  Gly  Arg  Cys  Asn  Ile
               20                       25                      30

Glu  Phe  Gly  Asn  Val  Glu  Ala  Gln  Ser  Arg  Phe  Ile  Phe  Phe  Val  Asp
          35                       40                       45

Ile  Trp  Thr  Thr  Val  Leu  Asp  Leu  Lys  Trp  Arg  Tyr  Lys  Met  Thr  Ile
     50                       55                       60

Phe  Ile  Thr  Ala  Phe  Leu  Gly  Ser  Trp  Phe  Phe  Gly  Leu  Leu  Trp
65                       70                       75                      80

Tyr  Ala  Val  Ala  Tyr  Ile  His  Lys  Asp  Leu  Pro  Glu  Phe  His  Pro  Ser
                    85                       90                           95

Ala  Asn  His  Thr  Pro  Cys  Val  Glu  Asn  Ile  Asn  Gly  Leu  Thr  Ser  Ala
               100                      105                     110

Phe  Leu  Phe  Ser  Leu  Glu  Thr  Gln  Val  Thr  Ile  Gly  Tyr  Gly  Phe  Arg
          115                      120                      125

Cys  Val  Thr  Glu  Gln  Cys  Ala  Thr  Ala  Ile  Phe  Leu  Leu  Ile  Phe  Gln
     130                      135                      140

Ser  Ile  Leu  Gly  Val  Ile  Ile  Asn  Ser  Phe  Met  Cys  Gly  Ala  Ile  Leu
145                      150                      155                     160

Ala  Lys  Ile  Ser  Arg  Pro  Lys  Lys  Arg  Ala  Lys  Thr  Ile  Thr  Phe  Ser
                    165                      170                     175

Lys  Asn  Ala  Val  Ile  Ser  Lys  Arg  Gly  Gly  Lys  Leu  Cys  Leu  Leu  Ile
               180                      185                     190

Arg  Val  Ala  Asn  Leu  Arg  Lys  Ser  Leu  Leu  Ile  Gly  Ser  His  Ile  Tyr
          195                      200                      205

Gly  Lys  Leu  Leu  Lys  Thr  Thr  Val  Thr  Pro  Glu  Gly  Glu  Thr  Ile  Ile
     210                      215                      220

Leu  Asp  Gln  Ile  Asn  Ile  Asn  Phe  Val  Val  Asp  Ala  Gly  Asn  Glu  Asn
```

-continued

```
               225                          230                           235                          240
    Leu  Phe  Phe  Ile  Ser  Pro  Leu  Thr  Ile  Tyr  His  Val  Ile  Asp  His  Asn
                        245                           250                          255

Ser  Pro  Phe  Phe  His  Met  Ala  Ala  Glu  Thr  Leu  Leu  Gln  Gln  Asp  Phe
                   260                          265                      270

Glu  Leu  Val  Val  Phe  Leu  Asp  Gly  Thr  Val  Glu  Ser  Thr  Ser  Ala  Thr
              275                          280                     285

Cys  Gln  Val  Arg  Thr  Ser  Tyr  Val  Pro  Glu  Glu  Val  Leu  Trp  Gly  Tyr
         290                          295                     300

Arg  Phe  Ala  Pro  Ile  Val  Ser  Lys  Thr  Lys  Glu  Gly  Lys  Tyr  Arg  Val
    305                          310                     315                          320

Asp  Phe  His  Asn  Phe  Ser  Lys  Thr  Val  Glu  Val  Glu  Thr  Pro  His  Cys
                        325                     330                          335

Ala  Met  Cys  Leu  Tyr  Asn  Glu  Lys  Asp  Val  Arg  Ala  Arg  Met  Lys  Arg
                   340                     345                          350

Gly  Tyr  Asp  Asn  Pro  Asn  Phe  Ile  Leu  Ser  Glu  Val  Asn  Glu  Thr  Asp
              355                     360                          365

Asp  Thr  Lys  Met
              370
```

(2) INFORMATION FOR SEQ ID NO:13:

(i) SEQUENCE CHARACTERISTICS:
      (A) LENGTH: 391 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
      (A) ORGANISM: Homo sapiens (vii) IMMEDIATE SOURCE:
      (B) CLONE: K8

(xi) SEQUENCE DESCRIPTION: SEQ ID NO:13:

```
    Met  Asn  Ala  Ser  Ser  Arg  Asn  Val  Phe  Asp  Thr  Leu  Ile  Arg  Val  Leu
    1                   5                        10                           15

Thr  Glu  Ser  Met  Phe  Lys  His  Leu  Arg  Lys  Trp  Val  Val  Thr  Arg  Phe
                   20                       25                      30

Phe  Gly  His  Ser  Arg  Gln  Arg  Ala  Arg  Leu  Val  Ser  Lys  Asp  Gly  Arg
                   35                       40                      45

Cys  Asn  Ile  Glu  Phe  Gly  Asn  Val  Glu  Ala  Gln  Ser  Arg  Phe  Ile  Phe
         50                       55                      60

Phe  Val  Asp  Ile  Trp  Thr  Thr  Val  Leu  Asp  Leu  Lys  Trp  Arg  Tyr  Lys
    65                       70                      75                          80

Met  Thr  Ile  Phe  Ile  Thr  Ala  Phe  Leu  Gly  Ser  Trp  Phe  Phe  Phe  Gly
                        85                      90                           95

Leu  Leu  Trp  Tyr  Ala  Val  Ala  Tyr  Ile  His  Lys  Asp  Leu  Pro  Glu  Phe
                   100                     105                     110

His  Pro  Ser  Ala  Asn  His  Thr  Pro  Cys  Val  Glu  Asn  Ile  Asn  Gly  Leu
              115                     120                     125

Thr  Ser  Ala  Phe  Leu  Phe  Ser  Leu  Glu  Thr  Gln  Val  Thr  Ile  Gly  Tyr
         130                     135                140
```

| | | | | | | | | | | | | | | |
|---|---|---|---|---|---|---|---|---|---|---|---|---|---|---|
|Gly|Phe|Arg|Cys|Val|Thr|Glu|Gln|Cys|Ala|Thr|Ala|Ile|Phe|Leu|Leu|
|145| | | | |150| | | |155| | | | | |160|
|Ile|Phe|Gln|Ser|Ile|Leu|Gly|Val|Ile|Ile|Asn|Ser|Phe|Met|Cys|Gly|
| | | | |165| | | |170| | | | |175| | |
|Ala|Ile|Leu|Ala|Lys|Ile|Ser|Arg|Pro|Lys|Lys|Arg|Ala|Lys|Thr|Ile|
| | | |180| | | |185| | | | |190| | | |
|Thr|Phe|Ser|Lys|Asn|Ala|Val|Ile|Ser|Lys|Arg|Gly|Gly|Lys|Leu|Cys|
| | |195| | | | |200| | | | |205| | | |
|Leu|Leu|Ile|Arg|Val|Ala|Asn|Leu|Arg|Lys|Ser|Leu|Leu|Ile|Gly|Ser|
| |210| | | | |215| | | | |220| | | | |
|His|Ile|Tyr|Gly|Lys|Leu|Leu|Lys|Thr|Thr|Val|Thr|Pro|Glu|Gly|Glu|
|225| | | | |230| | | |235| | | | | |240|
|Thr|Ile|Ile|Leu|Asp|Gln|Ile|Asn|Ile|Asn|Phe|Val|Val|Asp|Ala|Gly|
| | | | |245| | | |250| | | | |255| | |
|Asn|Glu|Asn|Leu|Phe|Phe|Ile|Ser|Pro|Leu|Thr|Ile|Tyr|His|Val|Ile|
| | | |260| | | |265| | | | |270| | | |
|Asp|His|Asn|Ser|Pro|Phe|Phe|His|Met|Ala|Ala|Glu|Thr|Leu|Leu|Gln|
| | |275| | | | |280| | | | |285| | | |
|Gln|Asp|Phe|Glu|Leu|Val|Val|Phe|Leu|Asp|Gly|Thr|Val|Glu|Ser|Thr|
| |290| | | | |295| | | | |300| | | | |
|Ser|Ala|Thr|Cys|Gln|Val|Arg|Thr|Ser|Tyr|Val|Pro|Glu|Glu|Val|Leu|
|305| | | | |310| | | |315| | | | | |320|
|Trp|Gly|Tyr|Arg|Phe|Ala|Pro|Ile|Val|Ser|Lys|Thr|Lys|Glu|Gly|Lys|
| | | | |325| | | |330| | | | |335| | |
|Tyr|Arg|Val|Asp|Phe|His|Asn|Phe|Ser|Lys|Thr|Val|Glu|Val|Glu|Thr|
| | | |340| | | |345| | | | |350| | | |
|Pro|His|Cys|Ala|Met|Cys|Leu|Tyr|Asn|Glu|Lys|Asp|Val|Arg|Ala|Arg|
| | |355| | | | |360| | | | |365| | | |
|Met|Lys|Arg|Gly|Tyr|Asp|Asn|Pro|Asn|Phe|Ile|Leu|Ser|Glu|Val|Asn|
| |370| | | | |375| | | | |380| | | | |
|Glu|Thr|Asp|Asp|Thr|Lys|Met| | | | | | | | | |
|385| | | | |390| | | | | | | | | | |

( 2 ) INFORMATION FOR SEQ ID NO:14:

( i ) SEQUENCE CHARACTERISTICS:
        ( A ) LENGTH: 383 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Homo sapiens ( v i i ) IMMEDIATE SOURCE:
        ( B ) CLONE: K2

( x i ) SEQUENCE DESCRIPTION: SEQ ID NO:14:

| | | | | | | | | | | | | | | |
|---|---|---|---|---|---|---|---|---|---|---|---|---|---|---|
|Met|Cys|Phe|Gln|Ile|Arg|Val|Leu|Thr|Glu|Ser|Met|Phe|Lys|His|Leu|
|1| | | |5| | | |10| | | | |15| | |
|Arg|Lys|Trp|Val|Val|Thr|Arg|Phe|Phe|Gly|His|Ser|Arg|Gln|Arg|Ala|
| | |20| | | | |25| | | | |30| | | |

-continued

```
Arg  Leu  Val  Ser  Lys  Asp  Gly  Arg  Cys  Asn  Ile  Glu  Phe  Gly  Asn  Val
          35                  40                       45
Glu  Ala  Gln  Ser  Arg  Phe  Ile  Phe  Phe  Val  Asp  Ile  Trp  Thr  Thr  Val
     50                       55                       60
Leu  Asp  Leu  Lys  Trp  Arg  Tyr  Lys  Met  Thr  Ile  Phe  Ile  Thr  Ala  Phe
65                       70                  75                            80
Leu  Gly  Ser  Trp  Phe  Phe  Phe  Gly  Leu  Leu  Trp  Tyr  Ala  Val  Ala  Tyr
                    85                       90                       95
Ile  His  Lys  Asp  Leu  Pro  Glu  Phe  His  Pro  Ser  Ala  Asn  His  Thr  Pro
               100                      105                      110
Cys  Val  Glu  Asn  Ile  Asn  Gly  Leu  Thr  Ser  Ala  Phe  Leu  Phe  Ser  Leu
          115                      120                      125
Glu  Thr  Gln  Val  Thr  Ile  Gly  Tyr  Gly  Phe  Arg  Cys  Val  Thr  Glu  Gln
     130                      135                      140
Cys  Ala  Thr  Ala  Ile  Phe  Leu  Leu  Ile  Phe  Gln  Ser  Ile  Leu  Gly  Val
145                           150                      155                     160
Ile  Ile  Asn  Ser  Phe  Met  Cys  Gly  Ala  Ile  Leu  Ala  Lys  Ile  Ser  Arg
                    165                      170                      175
Pro  Lys  Lys  Arg  Ala  Lys  Thr  Ile  Thr  Phe  Ser  Lys  Asn  Ala  Val  Ile
               180                      185                      190
Ser  Lys  Arg  Gly  Gly  Lys  Leu  Cys  Leu  Leu  Ile  Arg  Val  Ala  Asn  Leu
          195                      200                      205
Arg  Lys  Ser  Leu  Leu  Ile  Gly  Ser  His  Ile  Tyr  Gly  Lys  Leu  Leu  Lys
     210                      215                      220
Thr  Thr  Val  Thr  Pro  Glu  Gly  Glu  Thr  Ile  Ile  Leu  Asp  Gln  Ile  Asn
225                           230                      235                     240
Ile  Asn  Phe  Val  Val  Asp  Ala  Gly  Asn  Glu  Asn  Leu  Phe  Phe  Ile  Ser
                    245                      250                      255
Pro  Leu  Thr  Ile  Tyr  His  Val  Ile  Asp  His  Asn  Ser  Pro  Phe  Phe  His
               260                      265                      270
Met  Ala  Ala  Glu  Thr  Leu  Leu  Gln  Gln  Asp  Phe  Glu  Leu  Val  Val  Phe
          275                      280                      285
Leu  Asp  Gly  Thr  Val  Glu  Ser  Thr  Ser  Ala  Thr  Cys  Gln  Val  Arg  Thr
     290                      295                      300
Ser  Tyr  Val  Pro  Glu  Glu  Val  Leu  Trp  Gly  Tyr  Arg  Phe  Ala  Pro  Ile
305                           310                      315                     320
Val  Ser  Lys  Thr  Lys  Glu  Gly  Lys  Tyr  Arg  Val  Asp  Phe  His  Asn  Phe
                    325                      330                      335
Ser  Lys  Thr  Val  Glu  Val  Glu  Thr  Pro  His  Cys  Ala  Met  Cys  Leu  Tyr
               340                      345                      350
Asn  Glu  Lys  Asp  Val  Arg  Ala  Arg  Met  Lys  Arg  Gly  Tyr  Asp  Asn  Pro
          355                      360                      365
Asn  Phe  Ile  Leu  Ser  Glu  Val  Asn  Glu  Thr  Asp  Asp  Thr  Lys  Met
     370                      375                      380
```

( 2 ) INFORMATION FOR SEQ ID NO:15:

( i ) SEQUENCE CHARACTERISTICS:
        ( A ) LENGTH: 398 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO (v) FRAGMENT TYPE: N-terminal (vi) ORIGINAL SOURCE:
(A) ORGANISM: Rattus rattus (vii) IMMEDIATE SOURCE:
(B) CLONE: K6

(xi) SEQUENCE DESCRIPTION: SEQ ID NO:15:

```
Met Val Ser Glu Leu Ser Ile Pro Ser Ile Pro Thr Gly Val Ala Gly
1               5                   10                  15
Leu Ser Lys Ile Arg Val Leu Thr Glu Ser Met Phe Lys His Leu Arg
                20                  25                  30
Lys Trp Val Val Thr Arg Phe Phe Gly His Ser Arg Gln Arg Ala Arg
                35                  40                  45
Leu Val Ser Lys Asp Gly Arg Cys Asn Ile Glu Phe Gly Asn Val Glu
        50                  55                  60
Ala Gln Ser Arg Phe Ile Phe Phe Val Asp Ile Trp Thr Thr Val Leu
65                      70                  75                  80
Asp Leu Lys Trp Arg Tyr Lys Met Thr Ile Phe Ile Thr Ala Phe Leu
                    85                  90                  95
Gly Ser Trp Phe Phe Phe Gly Leu Leu Trp Tyr Ala Val Ala Tyr Ile
                100                 105                 110
His Lys Asp Leu Pro Glu Phe His Pro Ser Ala Asn His Thr Pro Cys
            115                 120                 125
Val Glu Asn Ile Asn Gly Leu Thr Ser Ala Phe Leu Phe Ser Leu Glu
        130                 135                 140
Thr Gln Val Thr Ile Gly Tyr Gly Phe Arg Cys Val Thr Glu Gln Cys
145                 150                 155                 160
Ala Thr Ala Ile Phe Leu Leu Ile Phe Gln Ser Ile Leu Gly Val Ile
                165                 170                 175
Ile Asn Ser Phe Met Cys Gly Ala Ile Leu Ala Lys Ile Ser Arg Pro
            180                 185                 190
Lys Lys Arg Ala Lys Thr Ile Thr Phe Ser Lys Asn Ala Val Ile Ser
        195                 200                 205
Lys Arg Gly Gly Lys Leu Cys Leu Leu Ile Arg Val Ala Asn Leu Arg
210                 215                 220
Lys Ser Leu Leu Ile Gly Ser His Ile Tyr Gly Lys Leu Leu Lys Thr
225                 230                 235                 240
Thr Val Thr Pro Glu Gly Glu Thr Ile Ile Leu Asp Gln Ile Asn Ile
                245                 250                 255
Asn Phe Val Val Asp Ala Gly Asn Glu Asn Leu Phe Phe Ile Ser Pro
                260                 265                 270
Leu Thr Ile Tyr His Val Ile Asp His Asn Ser Pro Phe Phe His Met
            275                 280                 285
Ala Ala Glu Thr Leu Leu Gln Gln Asp Phe Glu Leu Val Val Phe Leu
        290                 295                 300
Asp Gly Thr Val Glu Ser Thr Ser Ala Thr Cys Gln Val Arg Thr Ser
305                 310                 315                 320
Tyr Val Pro Glu Glu Val Leu Trp Gly Tyr Arg Phe Ala Pro Ile Val
                325                 330                 335
Ser Lys Thr Lys Glu Gly Lys Tyr Arg Val Asp Phe His Asn Phe Ser
                340                 345                 350
Lys Thr Val Glu Val Glu Thr Pro His Cys Ala Met Cys Leu Tyr Asn
                355                 360                 365
```

Glu  Lys  Asp  Val  Arg  Ala  Arg  Met  Lys  Arg  Gly  Tyr  Asp  Asn  Pro  Asn
             370                 375                      380

Phe  Ile  Leu  Ser  Glu  Val  Asn  Glu  Thr  Asp  Asp  Thr  Lys  Met
        385                      390                      395

( 2 ) INFORMATION FOR SEQ ID NO:16:

( i ) SEQUENCE CHARACTERISTICS:
        ( A ) LENGTH: 391 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Rattus rattus ( v i i ) IMMEDIATE SOURCE:
        ( B ) CLONE: Romk1

( x i ) SEQUENCE DESCRIPTION: SEQ ID NO:16:

Met  Gly  Ala  Ser  Glu  Arg  Ser  Val  Phe  Arg  Val  Leu  Ile  Arg  Ala  Leu
        1                   5                        10                       15

Thr  Glu  Arg  Met  Phe  Lys  His  Leu  Arg  Arg  Trp  Phe  Ile  Thr  His  Ile
                           20                       25                       30

Phe  Gly  Arg  Ser  Arg  Gln  Arg  Ala  Arg  Leu  Val  Ser  Lys  Glu  Gly  Arg
                       35                       40                       45

Cys  Asn  Ile  Glu  Phe  Gly  Asn  Val  Asp  Ala  Gln  Ser  Arg  Phe  Ile  Phe
             50                       55                       60

Phe  Val  Asp  Ile  Trp  Thr  Thr  Val  Leu  Asp  Leu  Lys  Trp  Arg  Tyr  Lys
        65                       70                       75                       80

Met  Thr  Val  Phe  Ile  Thr  Ala  Phe  Leu  Gly  Ser  Trp  Phe  Leu  Phe  Gly
                            85                       90                       95

Leu  Leu  Trp  Tyr  Val  Val  Ala  Tyr  Val  His  Lys  Asp  Leu  Pro  Glu  Phe
                       100                      105                      110

Tyr  Pro  Pro  Asp  Asn  Arg  Thr  Pro  Cys  Val  Glu  Asn  Ile  Asn  Gly  Met
                       115                      120                      125

Thr  Ser  Ala  Phe  Leu  Phe  Ser  Leu  Glu  Thr  Gln  Val  Thr  Ile  Gly  Tyr
             130                      135                      140

Gly  Phe  Arg  Phe  Val  Thr  Glu  Gln  Cys  Ala  Thr  Ala  Ile  Phe  Leu  Leu
        145                      150                      155                      160

Ile  Phe  Gln  Ser  Ile  Leu  Gly  Val  Ile  Ile  Asn  Ser  Phe  Met  Cys  Gly
                            165                      170                      175

Ala  Ile  Leu  Ala  Lys  Ile  Ser  Arg  Pro  Lys  Lys  Arg  Ala  Lys  Thr  Ile
                       180                      185                      190

Thr  Phe  Ser  Lys  Asn  Ala  Val  Ile  Ser  Lys  Arg  Gly  Gly  Lys  Leu  Cys
                       195                      200                      205

Leu  Leu  Ile  Arg  Val  Ala  Asn  Leu  Arg  Lys  Ser  Leu  Leu  Ile  Gly  Ser
             210                      215                      220

His  Ile  Tyr  Gly  Lys  Leu  Leu  Lys  Thr  Thr  Ile  Thr  Pro  Glu  Gly  Glu
        225                      230                      235                      240

Thr  Ile  Ile  Leu  Asp  Gln  Ile  Asn  Ile  Asn  Phe  Val  Val  Asp  Ala  Gly
                            245                      250                      255

Asn  Glu  Asn  Leu  Phe  Phe  Ile  Ser  Pro  Leu  Thr  Ile  Tyr  His  Ile  Ile

-continued

| | | | | | | 260 | | | | | 265 | | | | 270 | | |
|---|---|---|---|---|---|---|---|---|---|---|---|---|---|---|---|---|---|
| Asp | His | Asn 275 | Ser | Pro | Phe | Phe | His 280 | Met | Ala | Ala | Glu | Thr 285 | Leu | Ser | Gln | | |
| Gln | Asp 290 | Phe | Glu | Leu | Val | Val 295 | Phe | Leu | Asp | Gly | Thr 300 | Val | Glu | Ser | Thr | | |
| Ser 305 | Ala | Thr | Cys | Gln | Val 310 | Arg | Thr | Ser | Tyr | Val 315 | Pro | Glu | Glu | Val | Leu 320 | | |
| Trp | Gly | Tyr | Arg | Phe 325 | Val | Pro | Ile | Val | Ser 330 | Lys | Thr | Lys | Glu | Gly 335 | Lys | | |
| Tyr | Arg | Val | Asp 340 | Phe | His | Asn | Phe | Gly 345 | Lys | Thr | Val | Glu | Val 350 | Glu | Thr | | |
| Pro | His | Cys 355 | Ala | Met | Cys | Leu | Tyr 360 | Asn | Glu | Lys | Asp | Ala 365 | Arg | Ala | Arg | | |
| Met | Lys 370 | Arg | Gly | Tyr | Asp | Asn 375 | Pro | Asn | Phe | Val | Leu 380 | Ser | Glu | Val | Asp | | |
| Glu 385 | Thr | Asp | Asp | Thr | Gln 390 | Met | | | | | | | | | | | |

HUMAN DNA SEQUENCE ENCODING A KIDNEY ATP-DEPENDENT POTASSIUM CHANNEL

The present patent application is a continuation (national phase) application of International Application No. PCT/US94/01210, International Filing Date, 15 Feb. 1994, which was a continuation-in-part application of U.S. patent application Ser. No. 08/122,797, filed 17 Sep. 1993 (now abandoned), which was a continuation-in-part application of U.S. patent application Ser. No. 08/021,616, filed 19 Feb. 1993, (now abandoned).

BACKGROUND OF THE INVENTION

1. Field of the Invention

The present invention comprises human DNA compositions encoding proteins that confer potassium channel activity to membranes or recipient cell lines. The DNA compositions include structural genes coding for the potassium channel proteins, expression and replication plasmids or vectors containing the structural genes and host cells expressing those genes. Methods of screening compounds for potassium channel modulating activity are also described.

2. Description of the Related Art

Ho, K., et al. "Cloning and expression of an inwardly rectifying ATP-regulated potassium channel." Nature (4 Mar. 1993) Vol. 362 pp. 31–38. Describes the gene that encodes an ATP-regulated potassium channel protein from the inner stripe of outer medulla of rat kidneys.

Chandy, K., et. al., WO 92/02634, PCT/US91/05168, published 20 Feb. 1992. Describes the gene product known as MK3, a voltage dependent, type n potassium channel protein in T lymphocytes.

Harpold, M., et. al., WO92/02639, PCT/US91/05625, published 20 Feb. 1992. Transcription assays that identify compounds that modulate the activity of cell surface proteins. Cells that contains DNA that encode reporter genes, transcriptional control elements and heterologous cell surface proteins that may be potassium ion channels.

Luzdunski, M., "Potassium Channels: Structure-Function Relationships, Diversity, and Pharmacology," Cardiovascular Drugs and Therapy, (1992) Vol. 6, pp. 312–319. General description and information concerning potassium channels.

3. Background

Ionic channels of cell membranes are the basic sites where ionic fluxes take place. The modem era of the study of drug-channel interactions began when voltage clamp techniques were used to demonstrate the block of Sodium, ($Na^+$), and potassium, ($K^+$), channels of squid axons caused by procaine and cocaine. Narahashi, Ann Neurology (1984); 16(suppl): S39–S51.

This invention concerns potassium channels. Pharmacological and biophysical studies have revealed multiple subtypes for membrane ion channels that form potassium selective pores in the plasma membrane of many mammalian cells. Comparison of the pharmacological and electrophysiological properties of these potassium channels has given rise to an operational definition for grouping the various subtypes based largely on their gating properties.

Voltage-gated potassium channels sense changes in membrane potential and pass potassium ions in response to this alteration in the cell membrane potential. Ligand-gated potassium channels are regulated by small molecular weight effectors which include calcium, sodium, ATP or fatty acids (particularly arachidonic acid). Lazdunski, Cardiovascular Drugs and Therapy (1992) Vol. 6 pp. 313–319. Although these channel proteins share the common property that they selectively move potassium ions, their distinct biophysical, biochemical and pharmacological properties suggests that they are different gene products encoded by distinct genes.

The ATP-Sensitive, or ATP-gated, potassium channel is an important class of channels that links the bioenergetic situation of the cell to its electrical excitability. The channel is blocked by high intracellular ATP concentrations and it opens when ATP decreases. Lazdunski (1992). Although ATP-gated potassium channels were originally described in cardiac tissue; Noma, A. Nature (1983) Vol. 305 pp. 147–148, they have subsequently been described in pancreatic β-cells; Cook et. al., Nature (1984) Vol. 311 pp. 271–273, vascular smooth muscle; Nelson, M. T. et. al., Am. J. Physiol. (1990) Vol. 259 pp. C3–C18 and in the thick ascending limb of the kidney; Wang, W. et. al. Am. J. Physiol. (1990) Vol. 258, pp. F244–F-253.

Molecular cloning studies on potassium channel proteins has yielded some information, but only for members of the voltage-gated family of potassium channels. Various genes encoding these voltage-gated family of potassium channel proteins have been cloned using Drosophila genes derived from both the Shaker, Shaw and Shab loci; Wei, A. et. al., Science (1990) Vol. 248 pp. 599–603.

All known attempts to clone members of the ligand-gated family of potassium channel proteins using probes based on the known sequences of voltage-gated potassium channels have been unsuccessful. Taken together with the electrophysiological and pharmacological properties of these potassium channels, these results further confirm that the ATP-gated channel proteins are encoded by genes that are distinct from the genes that encode for voltage-gated potassium channels. These results indicate that there is little or no homology between the genes encoding voltage-sensitive potassium channels and the ATP-gated potassium channels.

A cDNA encoding a rat kidney potassium channel has been isolated by expression cloning, using a size-fractionated mRNA from the rat kidney thick ascending limb. When expressed in oocytes, the protein encoded by this gene displays many but not all of the hallmarks of a ATP-gated potassium channel. Ho, K., et al., Nature, Vol. 362 pp. 31–38 (4 Mar. 1993).

This invention describes the first successfully cloned human kidney ATP-gated and related potassium channel genes. Cloning these important genes will allow the production of important channel proteins into systems that will permit the identification, characterization and cloning of potential drug targets. This invention includes the development of a high volume mechanistic screen and it will allow the production of appropriate systems for the production of material for biochemical study.

The discovery of the highly selective and potent sodium channel blocking action of tetrodotoxin ignited a widespread interest in using specific chemicals as probes for the study of ionic channels. Narahashi (1984). The present invention provides an important potassium channel that may allow the discovery of other important physiological compounds.

SUMMARY OF THE INVENTION

This invention comprises the first isolation of functional cDNA clones encoding human potassium ATP-gated channel proteins, and derivatives thereof. This invention describes the following. Isolated DNA molecules encoding a human kidney ATP-gated and related potassium channel having the sequences shown in FIGS. 1–5 and selected derivatives thereof. Various vectors comprising the DNA molecules of FIGS. 1–5 and selected derivatives thereof. Various plasmids comprising the DNA molecules of FIGS. 1–5 and selected derivatives thereof. Vectors and plasmids adapted for expression in a bacterial cell, yeast cell, or a mammalian cell. Use of the bacterial, yeast, or mammalian cell containing the vector or plasmid of FIGS. 1–5 or selected derivatives thereof, to screen for compounds that modulate human kidney ATP-gated and related potassium channel activity.

The invention also comprises an isolated DNA molecule encoding a human kidney potassium channel protein, the isolated protein, and isolated mammalian cells comprising the protein, having the sequences shown in FIGS. 1, 2, 3, 4, or 5; from the clones named K-8, K-11 or K-12, or derivatives selected from obvious variations thereof, or having the DNA coding for the N-terminal protein sequences as shown in Table 1; from the clones named K-2, K-6, K-8, K-11, or K-26 and having the remaining DNA not shown in Table 1 but as shown in FIGS. 1–5, or having the DNA coding any of about the first 26N terminal amino acids, including any deletions, of the protein coded for by the DNA shown in FIGS. 1–5, or the protein shown in FIG. 6 or Table 1, or a DNA molecule 90 percent homologous to any of the above described DNA molecules thereof.

Also claimed is a method of using a mammalian cell as described above, to screen for compounds that modulate human kidney potassium channel activity. The method may be comprised of the following steps: a) growing cells expressing a cloned $K^+$ channel to confluence, b) equilibrating the cells of a) with a balanced salt solution, c) making baseline measurements of the equilibrated cells, d) adding one test compound or a cocktail of test compounds to the cells and recording changes in membrane potential, e) testing compounds that depolarize cells expressing the $K^+$ channel on wild type or mock transfected controls to identify compounds that exhibit selective K+ channel blocking behavior, f) selecting the compounds that are shown to selectively block $K^+$.

BRIEF DESCRIPTION OF THE DRAWINGS

FIGS. 1(A–C). Translation of the open-reading frame encoded by cDNA clone K26 (coding cDNA is SEQ. ID. NO. 6, amino acid sequence is SEQ. ID. NO. 11).

FIGS. 2(A–C). Translation of the open-reading frame encoded by cDNA clone K26-plus (coding cDNA is SEQ. ID. NO. 7, amino acid sequence is SEQ. ID. NO. 12).

FIGS. 3(A–C). Translation of the open-reading frame encoded by cDNA clone K11 coding cDNA is SEQ. ID. NO. 8, amino acid sequence is SEQ. ID. NO. 12).

FIGS. 4(A–C). Translation of the open-reading frame encoded by cDNA clone K11-plus (coding cDNA is SEQ. ID. NO. 9, amino acid sequence is SEQ. ID. NO. 12).

FIGS. 5(A–C). Translation of the open-reading frame encoded by cDNA clone K-8 (coding cDNA is SEQ. ID. NO. 10, amino acid sequence is SEQ. ID. NO. 13).

FIGS. 6(A–B). Amino acid sequence alignment of human kidney K-ATP channel proteins (Romk1 is SEQ. ID. NO. 16; K8 is SEQ. ID. NO. 13; K11, K11+, K26+ are all SEQ. ID. NO. 12; and K26 is SEQ. ID. NO. 11).

FIGS. 7A–7F. Whole cell recordings of K-8, K11 and K26 channels expressed in Xenopus oocytes.

FIGS. 13A–13C. KCl-dependent depolarization of A10 cells analyzed on FLIPR.

BRIEF DESCRIPTION OF THE SEQUENCE LISTINGS

Figure 7D:
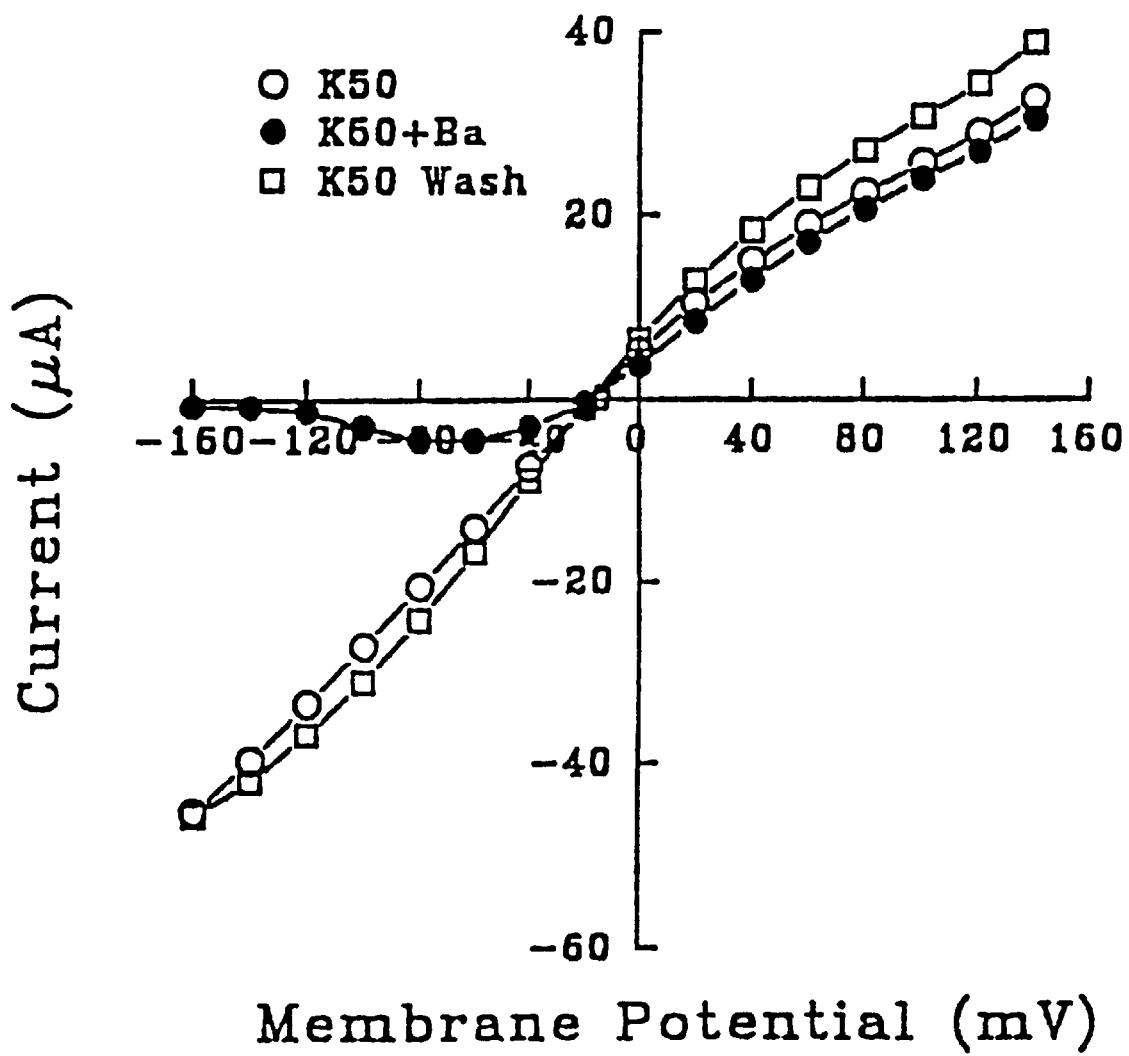

SEQ. ID. NO. 1. cDNA of clone K26, includes the 5' and 3' untranslated region.

SEQ. ID. NO. 2. cDNA of clone K26-plus, includes the 5' and 3' untranslated region.

SEQ. ID. NO. 3. cDNA of clone K11, includes the 5' and 3' untranslated region.

SEQ. ID. NO. 4. cDNA of clone K11-plus, includes the 5' and 3' untranslated region.

SEQ. ID. NO. 5. cDNA of clone K8, includes the 5' and 3' untranslated region.

SEQ. ID. NO. 6. cDNA of clone K26, coding region. See also FIG. 1.

SEQ. ID. NO. 7. cDNA of clone K26-plus, coding region. See also FIGS. 2, 3, and 4.

SEQ. ID. NO. 8. cDNA of clone K11, coding region. See also FIGS. 2, 3, and 4.

SEQ. ID. NO. 9. cDNA of clone K11-plus, coding region. See also FIGS. 2, 3, and 4.

SEQ. ID. NO. 10. cDNA of clone K8, coding region. See also FIG. 5.

SEQ. ID. NO. 11. Amino acid sequence of K26. See also the amino acids in FIG. 1 and the amino acids lited as "cDNA K26" in FIG. 6.

SEQ. ID. NO. 12. Amino acid sequence of K26-plus, K-11, K11-plus. See also the amino acids in FIGS. 2, 3, and 4, and the amino acids listed as "cDNA K11, cDNA K11p1 and cDNA K26p1" in FIG. 6.

SEQ. ID. NO. 13. Amino acid sequence of K8. See also, the amino acids in FIG. 5, and the amino acids listed as "cDNA K8" in FIG. 6.

SEQ. ID. NO. 14. Amino acid sequence of K2.

SEQ. ID. NO. 15. Amino acid sequence of K6.

SEQ. ID. NO. 16. Amino acid sequence from Romk1 from FIG. 6.

DESCRIPTION OF THE PREFERRED EMBODIMENTS

This invention relates to the cloning and isolation of human DNAs encoding a functional potassium ATP-gated channel proteins. In one embodiment this invention comprises the first isolation of functional cDNA clones encoding human potassium ATP-gated channel proteins as verified by using *Xenopus laevis* oocytes as an expression system for studying ion channels. Mammalian and a bacterial cell lines expressing functional human potassium ATP-gated channels at the cell surface are described, as determined by pharmacologic and physiologic methods, thus establishing the first well-defined cell lines with which to study this particular member of a family of ATP-gated channel proteins. In another embodiment those human potassium ATP-gated channels are shown operating in a high volumn screen.

Definitions. This document uses abbreviations and terms that should be well known to those skilled in the art. Some terms are more fully described in the sections below.

I. Isolation of a Functional Human Potassium Channel DNA Clone

1. Isolation of rat kidney cDNA PvuII/BamHI fragment.

A rat kidney ATP-potassium channel cDNA termed ROM-K1 incorporated into the plasmid pSPORT is obtained using the procedures described in Ho, K., et. al. "Cloning and expression of an inwardly rectifying ATP-regulated potassium channel." Nature, Vol. 362 pp. 31–38 (4 Mar. 1993), incorporated by reference. This rat kidney ATP-potassium channel cDNA from the plasmid pSPORT is digested to completion with the restriction endonucleases PvuII and BamHI. The resulting 1.3 kilobase insert DNA containing the entire open-reading frame of ROM-K1 is purified by preparative agarose gel electrophoresis.

2. Radiolabeling of rat fragment.

The isolated rat kidney cDNA PvuII/BamHI fragment is radiolabeled using $\alpha$-$^{32}$P-dATP and random hexamers in the presence of the Klenow fragment of DNA polymerase I.

3. Isolation of recombinant bacteriophage containing human K-channel cDNAs.

A human kidney cDNA library in the bacteriophage vector lambda gt10 is titered on E. coli C600 hfl$^-$ and 400,000 independent recombinants are plated on agar plates. Replicate lifts of the agar plates are prepared on nylon membranes and the denatured phage DNA immobilized on the filters by baking. The replicate nylon lifts are prehybridized in buffer to block non-specific binding sites and then hybridized with the $^{32}$P random-prime labeled PvuII/BamHI fragment of ROM-K1. The filters are then washed with 0.3M NaCl/0.1% SDS at 65° C. The coordinates of radioactivity on the filters are determined by autoradiography at –70° C. with intensifying screens. Replicate positive bacteriophage are isolated from the agar plates and cloned by dilution plating and rescreening as described in the Nature article by Ho, above.

4. Preparation of bacteriotphage DNA from the clonal phage stocks.

Clonal bacteriophage stocks of the hybridization-positive clones, from step 3, above, are used to prepare bacteriophage DNA by infection of E. coli followed by DNA isolation. E. coli cultures are infected with clonal phage and bacteriophage DNA isolated from the infected culture using a combination of polyethylene glycol precipitation of the bacteriophage particles followed by destruction of the bacteriophage protein coat. Bacteriophage DNAs prepared in this manner were digested with EcoRI to produce the cDNA inserts. The size of the liberated insert cDNAs is determined by size fractionation on agarose gels. The fractionated cDNAs are then transferred to a nylon membrane by capillary action and homologous sequences are detected by hybridization to the $^{32}$P-PvuII/BamHI fragment of ROM-K1 and autoradiography as described above.

5. Sequencing of selected bacteriophage DNAs.

Bacteriophage DNAs prepared from clones with distinct EcoRI restriction patterns are selected and then sequenced by cycle sequencing dideoxy-chain termination reactions. The dideoxy chain termination method may utilize the SEQUENASE(™) methods and products, available from United States Biochemicals, Cleveland, Ohio. This is followed by denaturing gel separation of the reaction products, autoradiographic detection of the fractionated DNA bands and manual reading of the gels.

6. Cloning of alternate human K-ATP channel DNAs.

The DNA sequence analysis revealed a common core-exon, shared by all of the cDNAs, flanked by alternate 5' sequences. These alternate 5' sequences were further characterized by mapping the transcriptional start-sites for each transcript using a combination of reverse transcriptase/polymerase chain reaction (RT/PCR) amplification and 5' rapid amplification of cDNA ends (RACE) analysis. A synthetic oligonucleotide primer complementary to the shared core exon sequence (HROM 4) was used to reverse transcribe human kidney total RNA using the MMLV reverse transcriptase. The cDNA products were then PCR amplified using either an anchor primer (5' RACE) or a primer specific for the 5' untranslated sequence of the K26 cDNA (HROM-10). This led to the isolation of five distinct cDNAs referred to as: K-8, K11, K11$^+$, K26 and K26$^+$ The PCR products were subcloned into plasmid vectors and completely sequenced on both strands as described above. The complete sequences of the K-8, K11, K11$^+$, K26, and K26$^+$ cDNAs was assigned using a combination of the bacteriophage cDNA sequences and the sequences of both the RT-PCR and 5' RACE products (FIGS. 1–5).

7. Selection of the clones and selected derivates of the clones.

The DNA sequence of clone K26 contains a single open-reading frame that encodes a 389 amino acid residue protein that displays close sequence identity to the rat kidney ROM-K1 potassium channel with one important difference. The actual amino acid residues found in the N-terminal domain, the first 26 amino acids, and especially the first 10 amino acids, show surprising and unexpected differences from what one would ordinarily predict from an analysis of the rat sequence. The N-terminal amino acid residues, which are present in the intracellular space prior to protein's insertion into the plasma membrane, show a greater than expected divergence from the rat sequence, greater than one would expect given the high homology found in species homologs of the same and similar channel proteins.

Note that the K-8 cDNA encodes a human species homolog that is the same length as the rat kidney ROM-K1 channel. When comparing ROM-K1 with K-8, there are important amino acid differences, and the corresponding DNA, is different, yet both the rat and the human have a similar distinct amino acid terminus. Significantly, the K11, K-11$^+$, K26 K26$^+$, and two other K$^+$ channel proteins, we call K2 and K-6, have different lengths as well as types of amino acids in this important region. The differences were unexpected, given only the rat sequence.

The different human (K11, K2, K26, K8) and rat (K6) amino acid terminals are shown in Table 1, below:

TABLE 1

| | |
|---|---|
| K11 plus and K26 plus | (deletion)-MFKHLR . . . (FIG. 2 and SEQ ID NO.12) |
| K2 | MCFQ-IRVLTES-MFKHLR . . . (SEQ ID NO.14) |
| K26 | MPTVYLCSEQ-IRVLTES-MFKHLR . . . (FIG. 1 and SEQ ID NO.11) |
| K/8 | MNASSRNVFDTL-IRVLTES-MFKHLR . . . (FIG. 5 and SEQ ID NO.13) |
| K/6 | MVSELSIPSIPTGVAGLSK-IRVLTES-MFKHLR . . . (SEQ ID NO.15) |

Thus K2 has 8 fewer sequences than ROM-K1, while K-6 has 7 sequences more than ROM-K1. These initial 26 or so N-terminal amino acids are the most important variable region of the protein, the remaining portion of the protein being highly homologous. Investigations show that differences in this N-terminal region may can result in functional differences in the protein. The rat ROM-K1, and the K8 disclosed here, show little or no inhibition to ATP. The endogenous $K^+$ channel is inhibited by ATP, therefore; it is likely that one of the other variants would show inhibition to ATP. It appears that K11 is the most abundant protein in the thick ascending limb of the kidney. In the kidney the functional $K^+$ channel is inhibited by ATP, therefore it would be logical to test the protein variants for inhibition by ATP and to use proteins that would are inhibited by ATP to screen for $K^+$ blocking agents. Other functional differences may be associated with the other N-terminal sequences.

All of these human protein sequences, the DNA that codes for them, obvious variants thereof, homologous sequences thereof, allowing for conservative substitutions but expecting at least 90 percent homology are included as the invention described herein. The first 26 or so N-terminal sequences, or their absence or deletions, are very important but it is also observed that conservative substitutions are to be expected anywhere in the sequence and all are included here.

II. Preparation of Suitable Vectors Incorporating Human Potassium Channel DNA

1. The pGEM7 vector.
    a. Preparation of clone coding sequence. The open-reading frames of the K-8, K11 and K26 clones are obtained by restriction endonuclease digestion of the lambda DNAs with KpnI/AccI, XhoI/AccI or MunI, respectively. The DNA fragments are purified by preparative agarose gel electrophoresis.
    b. Introduction of the clones into a plasmid vectors. Tee K-8, K11 and K26 cDNA fragments were subcloned into the multiple cloning site of either pSP64poly A (K-8 and K11) or pGEM7 (K26) to yield K-8/pSP64, K11/pSP64 or pGEM7/K26, respectively.
2. The pSVL/K26 vector.
    a. The pGEM7/K26 plasmid is double-digested with the restriction endonucleases XhoI and BamHI and the resulting fragment is purified by preparative agarose gel electrophoresis.
    b. The isolated XhoI/BamHI fragment of K26 is subcloned into the transient expression vector pSVL to yield expression plasmid pSVL/K26.
3. The pCEP4 vector.
    a. The XhoI/BamHI fragment containing the entire coding sequence of K26 is subcloned into the expression vector pCEP4 to yield the expression vector pCEP/K26.
4. The pMEP vector.
    a. The XhoI/BamHI fragment containing the entire coding sequence of K26 is subcloned into the expression vector pMEP to yield the expression vector pMEP/K26.
5. The pMAL2c/K26 vector.
    a. The entire coding sequence of K26 is adapted for expression using the polymerase chain reaction (PCR) using primers containing the appropriate restriction endonuclease recognition sites.
    b. The engineered PvuII/BamHI PCR fragment is subcloned into the bacterial expression vector pMAL2c.
    c. The integrity of the PCR product is verified by DNA sequencing using the dideoxy-chain termination method.
6. The pYESI vector.
    a. The entire coding sequence of K26 is adapted for expression using the polymerase chain reaction (PCR) using primers containing the appropriate restriction endonuclease recognition sites (Not I).
    b. The engineered NOT I PCR fragment is subcloned into the bacterial expression vector pYESI.
    c. The integrity of the PCR product is verified by DNA sequencing using the dideoxy-chain termination method.

III. Expression of the Protein Encoded by the Human Potassium Channel DNA Clone

1. Transient expression of K26 clone in COS 7 cells.
    a. The pSVL/K26 expression plasmid is used to transfect COS 7 cells using the cationic liposome DOTAP. This cationic liposome is available from Boehringer Mannheim, Indianapolis, Ind. Functional expression is determined by transcript analysis and functional expression is monitored optically by measuring the effect of $Ba^{2+}$ on the resting membrane potential of the transfected cells. See Experimental Details, below.
2. Transient expression of K26 clone in oocytes
    a. Oocyte expression of K-8, K11 and K26 clone.
        i. The pSP64poly A system in Oocytes.
    1. The pSP64poly A vector is digested to completion with EcoRI and the product filled-in using Klenow polymerase. The blunt-end product of the fill-in reaction is linkered with Not I linkers and the Not I sites generated by digestion with Not I.
    2. The K-8, K11 and K26 pSP64poly A plasmid DNAs are linearized by digestion with Not I and purified by preparative gel electrophoresis.
    3. Sense cRNA is synthesized off of the BamHI-digested pGEM7/K26 template using SP6 RNA polymerase and 5' capped in the same reaction.
    4. Capped cRNA is microinjected into Xenopus oocytes and allowed to express for 72 hours.
    5. Potassium channel activity is monitored 72 hours after microinjection by electrophysiological measurements in both the whole cell and detached patch recording modes. See Experimental Details, below.
    3. Stable expression of the K26 DNA clone in mammalian cells.
    a. Chinese hamster ovary (CHO), African Green Monkey Kidney Cells (COS), human embryonic kidney and mouse L-cell expression of K26.

i. The pCEP/K26 and pMEP/K26 vector expression systems.
1. The pMEP/K26 and pCEP/K26 expression plasmid are used to transfect chinese hamster ovary, COS, human embryonic kidney and mouse L-cells using the cationic liposome DOTAP.
2. Stable transfectants are selected by culturing of the cells in the presence of Hygromycin B. Stable clonal cell lines are subcloned several times to insure clonal lineage. The expression of K26 in the transfected cells is determined by analyzing for K26 transcripts (Northern blot analysis and RT-PCR) and using a functional assay. The latter is performed by optically measuring changes in membrane potential using the reporter dye DiBAC after the addition of $Ba^{2+}$. The expression of K26 is also determined by electrophysiological procedures. See Experimental Details, below.
4. Stable expression of the K26 DNA clone in bacterial cells.
    a. The pMAL2c/K26 system.
        i. Induction of expression of the pMAL2c/K26 plasmid containing $DH_{5\alpha}$ is induced by addition of IPTG to exponentially growing cultures.
        ii. Expression of the desired protein product is verified by SDS-PAGE analysis of bacterial cells isolated from the induced cultures.

IV. Bioassays Using Expression Systems Based on the Protein Encoded by the Human Potassium Channel DNA Clone This section describes methods and procedures for using the bacterial cells, yeast cells and or mammalian cells expressing the human kidney ATP-gated and related potassium channel to screen for compounds that modulate human kidney ATP-potassium channel activity.

Mammalian cells that are stably transfected with K26 are grown in multiwell tissue culture dishes. The tissue culture dish of choice is one that contains 96 wells. Other tissue culture dishes could also be used. The membrane potential of the mammalian cells expressing K26 is optically measured using a voltage-sensitive fluorescent dye. The dye of choice is bis(1,3-dibutylbarbituric acid)trimethine oxonol ($DiBAC_4(3)$). Other voltage sensitive dyes could also be used. Changes in membrane potential are detected by measuring changes in cellular fluorescence against a high background of noncellular fluorescence. The cell associated fluorescence is measured, not just the total well fluorescence. A better system for measuring changes in membrane potential is to use a 96 well plate reader that can measure changes in cellular fluorescence against a high background of noncellular fluorescence for all 96 wells at once. FLIPR a laser system manufactured and available from NovelTech, Ann Arbor, Mich., is one such system. The screen consists of adding agents to cells that express K26. Agents that block K26 cause the cells to depolarize. Agents that activate K26 cause the cells to hyperpolarize. Specificity is determined in several ways. The first test of specificity is to determine if agents of interest modulate the membrane potential of mock transfected cells. These cells contain the vector that K26 is cloned into but do not express the K26 gene product. Other tests of specificity include determining if agents of interest modulate the activity of other $K^+$ channels.

The invention should be readily appreciated and understood by those skilled in the art from the descriptions above. The following Experimental Details are supplied to provide details of the best mode of the invention and to illustrate the completed invention more fully. They should not be considered limitations on the invention.

EXPERIMENTAL DETAILS

I. Isolation of a Functional Human Potassium Channel DNA Clone

1. Isolation of rat kidney cDNA PvuII/BamHI fragment.

A rat kidney ATP-potassium channel cDNA termed ROM-K1 is obtained using the procedures described in Ho, K., et. al. "Cloning and expression of an inwardly rectifying ATP-regulated potassium channel." Nature, Vol. 362 pp. 31–38 (4 Mar. 1993). The ROM-K1 cDNA in the plasmid vector pSPORT was passaged in *E. coli* strain $DH_{5\alpha}$ under ampicillin selection (Maniatis, et al., Molecular Cloning, Cold Spring Harbor Laboratory, 1982). Purified plasmid DNA was double-digested with the restriction endonucleases PvuII and BamHI and the resulting 1.3 kilobase fragment containing the entire open-reading frame of ROM-K1 was purified by preparative agarose gel electrophoresis followed by electroelution of the isolated fragment.

2. Radiolabeling of rat fragment.

The isolated rat kidney cDNA PvuII/BamHI, 1.3 kilobase restriction fragment was radiolabeled using $\alpha$-$^{32}P$-dATP and random hexamers in the presence of the Klenow fragment of DNA polymerase I (A. P. Feinberg and B. Vogelstein, Anal. Biochem. 137, 266 (1984)).

3. Preparation of human positive bacteriophage.

A human kidney cDNA library in the bacteriophage vector lambda gt10, purchased from Clonetech, Palo Alto, Calif. is titered on *E. coli* C600 hfl⁻ and 400,000 independent recombinants are plated on agar plates. Replicate lifts of the agar plates are prepared on nylon membranes and the phage DNA immobilized on the filters by baking. The replicate nylon lifts are prehybridized in buffer to block non-specific binding sites and then hybridized with the $^{32}P$-labeled PvuII/BamHI fragment, labeled as described above. The filters are then washed with 0.3M NaCl/0.1% SDS at 65° C. The coordinates of radioactivity on the filters is determined by autoradiography at −70° C. with intensifying screens. Sixty two replicate positives were identified from the primary screen and each of these replicate positives is cloned by limiting dilution followed by reiterative plating on agar plates and rescreening with the $^{32}P$-labeled ROM-K1 probe and autoradiography as described above.

4. Preparation Bacteriophage DNA from the Clonal phage stocks.

Bacteriophage DNA is prepared from the clonal phage stocks of positive clones, from step 3, above, by infection of *E. coli* followed by DNA isolation. *E. coli* cultures infected with bacteriophage from clonal stocks are used to prepare bacteriophage DNA by lysis followed by polyethylene glycol precipitation and destruction of the bacteriophage protein coat (Maniatis, et al., Molecular Cloning, Cold Spring Harbor, 1982). Purified bacteriophage lambda DNAs were digested with EcoRI to produce fractionated cDNAs. The size of the liberated insert cDNAs is determined by size fractionation on agarose gels. The fractionated cDNAs are then transferred to a nylon membrane by capillary action and homologous sequences are detected by hybridization to the $^{32}P$-PvuII/BamHI fragment and autoradiography as described above (Southern, E. Mol. Biol. 98, 503 (1975)). Homologous DNA sequences are detected by hybridization with $^{32}P$-labeled DNA fragments derived from various portions of the ROM-K1 coding sequence followed by low stringency washes as described above. Phage DNAs displaying unique hybridization patterns were then subjected to DNA sequence analysis.

5. Sequencing of selected bacteriophage DNAs.

Bacteriophage DNAs from clones with distinct EcoRI restriction patterns are selected and then the DNA sequence of each bacteriophage is determined directly from the bacteriophage DNAs using cycle sequencing dideoxy-chain termination reactions. (AmpliTaq kit, Perkin Elmer-Cetus, Norwalk, Conn.). The reaction products are resolved on 1 meter denaturing polyacrylamide gels followed by autoradiographic detection of the fractionated DNAs. Manual reading of the DNA sequence is then performed.

6. Mapping of the human kidney transcript 5' ends

Sequence analysis of the bacteriophage cDNAs isolated from the human kidney library revealed a common core exon fused to variable 5' sequences. The transcripts that give rise to these cDNAs were further analyzed by reverse transcriptase cDNA synthesis coupled to the polymerase chain reaction amplification of the K-channel transcripts (RT-PCR). First strand cDNA synthesis was primed using oligo dT and MMLV reverse transcriptase (Bethesda Research Laboratories, Gaitherburg, Md.) on a human kidney total RNA template. A portion of the first strand cDNA product was PCR amplified using a common 3' oligonucleotide primer that is specific for the core-exon (HROM4) combined with a 5' oligonucleotide primer that is specific for either the K-8 or K11/K26 cDNAs. These products of the PCR amplification reactions were fractionated according to size on an agarose gel and recovered by electroelution. Each individual fragment was blunt-ended using Klenow fragment of DNA polymerase I, phosphorylated using T4 polynucleotide kinase and subcloned into SmaI digested pUC19. The sequence of each subcloned PCR product was determined by the dideoxy chain termination method using SEQUENASE™ (United States Biochemicals, Cleveland, Ohio). Composite cDNA sequences were constructed using a combination of the cDNA sequences and the sequences obtained from the RT-PCR products and are shown in FIG. 2. Our analysis revealed 5 distinct transcripts in the human kidney.

7. Selection of the clone.

Translation of the open reading frames encoded by the 5 distinct transcripts isolated from human kidney RNA showed that they had the potential to encode 3 distinct amino terminal variants of human the kidney $K_{ATP}$ channel protein. Each transcript encoded a protein that had all of the hallmarks of a $K_{ATP}$ channel protein including the presence of two predicted membrane spanning domains, a region that showed remarkable homology to the Shaker K-channel H5 domain and a single predicted ATP-binding site. Clone K-8 contained a 1173 base-pair open reading frame that encoded a 391 amino acid protein that was >92% identical to rat kidney ROM-K1. Clone K26 contained a single open-reading frame (1167 base-pair) that encoded a 389 amino acid residue protein that was identical to K-8 except that the amino terminus (10 amino acid residues) was completely distinct. Finally, clones K11, K11+ and K26+ all encoded the same 372 residue channel protein, that was an amino terminal truncated version of either K-8 or K26 that is lacking either the amino terminal 19 or 17 residues from K-8 and K26, respectively.

Each DNA sequence was engineered for expression in the vectors for mammalian cell expression (pCEP and pMEP), for oocyte expression (pSP64-poly A), for bacterial expression (pMAL2c) or yeast expression (pYES) and these constructs used to express the various human kidney $K_{ATP}$ channels in the appropriate host.

8. Clone purification.

The K26 lambda DNA is digested with the restriction endonuclease MunI and the 1.3 kilobase fragment is purified by preparative agarose gel electrophoresis.

II. Preparation of Suitable Vectors Incorporating Human Potassium Channel DNA

1. The pGEM7 vector.

The 1.3 kilobase MunI restriction fragment is subcloned into the EcoRI site of the plasmid vector pGEM7.

cRNA capping. The pGEM7/K26 plasmid is linearized with BamHI. The linearized plasmid is then transcribed and capped with 7MeGppp5'G using T7 RNA polymerase.

2. The pSVL/K26 vector. The pGEM7/K26 plasmid is double digested with XhoI and BamHI and the resulting fragment subcloned into pSVL to yield pSVL/K26.

3. The pCEP4 vector.

The XhoI/BamHI fragment of K26 is subcloned into the plasmid vector pCEP to yield pCEP/K26.

4. The pMEP vector.

The XhoI/BamHI fragment of K26 is subcloned into the plasmid vector pMEP to yield pMEP/K26.

III. Expression of the Protein Endcoded by the Human Potassium Channel DNA Clone 1. Transient expression of K26 clone in COS 7 cells.

The plasmid pGEM7/K26 is digested to completion with the restriction endonucleases XhoI and BamHI and the 1.3 kb fragment containing the K26 coding sequence is isolated by preparative agarose gel electrophoresis. This fragment is ligated to the plasmid vector pSVL and the ligation products used to transform competent E. coli DH5$_\alpha$ cells. pSVL/K26 expression plasmid DNA is prepared from the appropriate clone and purified pSVL/K26 plasmid DNA is used to transfect COS 7 cells using the cationic liposome DOTAP (Boehringer Mannheim, Indianapolis, Ind.). Channel activity is detected 48–72 hours post transfection.

2. Stable expression of the K26 DNA clone in mammalian cells.
   a. Chinese hamster ovary (CHO), African Green Monkey Kidney Cells (COS), human embryonic kidney and mouse L-cell expression of K26.
      i. The pCEP/K26 or the pMEP/K26 expression plasmids are used to transfect COS 7 cells or human embryonic kidney cells (293 cells) using the cationic liposome DOTAP. 20 hour post-transfection, the cells are treated with 0.15–0.5 mg/ml hygromycin B to kill non-transfected cells. Individual cell lines are isolated by single cell cloning.

3. Functional Expression of K-8, K11 and K26 cRNAs in Xenopus oocytes.

We examined the electrophysiological properties of the K-8, K11 and K26 polypeptides by expression in Xenopus oocytes. Polyadenylated cRNAs (45 nl of a 100 ng/ul) were injected into oocytes and allowed to express for 48–72 hr. Forty eight hour post injection with K-8, K11 and K26, the oocytes had resting membrane potentials of −90.08±1.90 mV (n=9), −97.2±0 mV (n=1) and −88.75±0.45 mV (n=2) respectively, and these remained relatively unchanged at −87.89±1.57 mV (n=7), −93±0.79 mV (n=7) and −88.4±2.11 mV (n=4) on day 3. The water injected control oocytes had average resting potentials of about −40 mV. The significantly more negative potential of oocytes injected with ROM-K cRNAs is due to functional expression of these channels and the values are close to the K equilibrium potential calculated for the estimated K gradient (2 mM extracellular/100 mM intracellular).

Figure 7E:
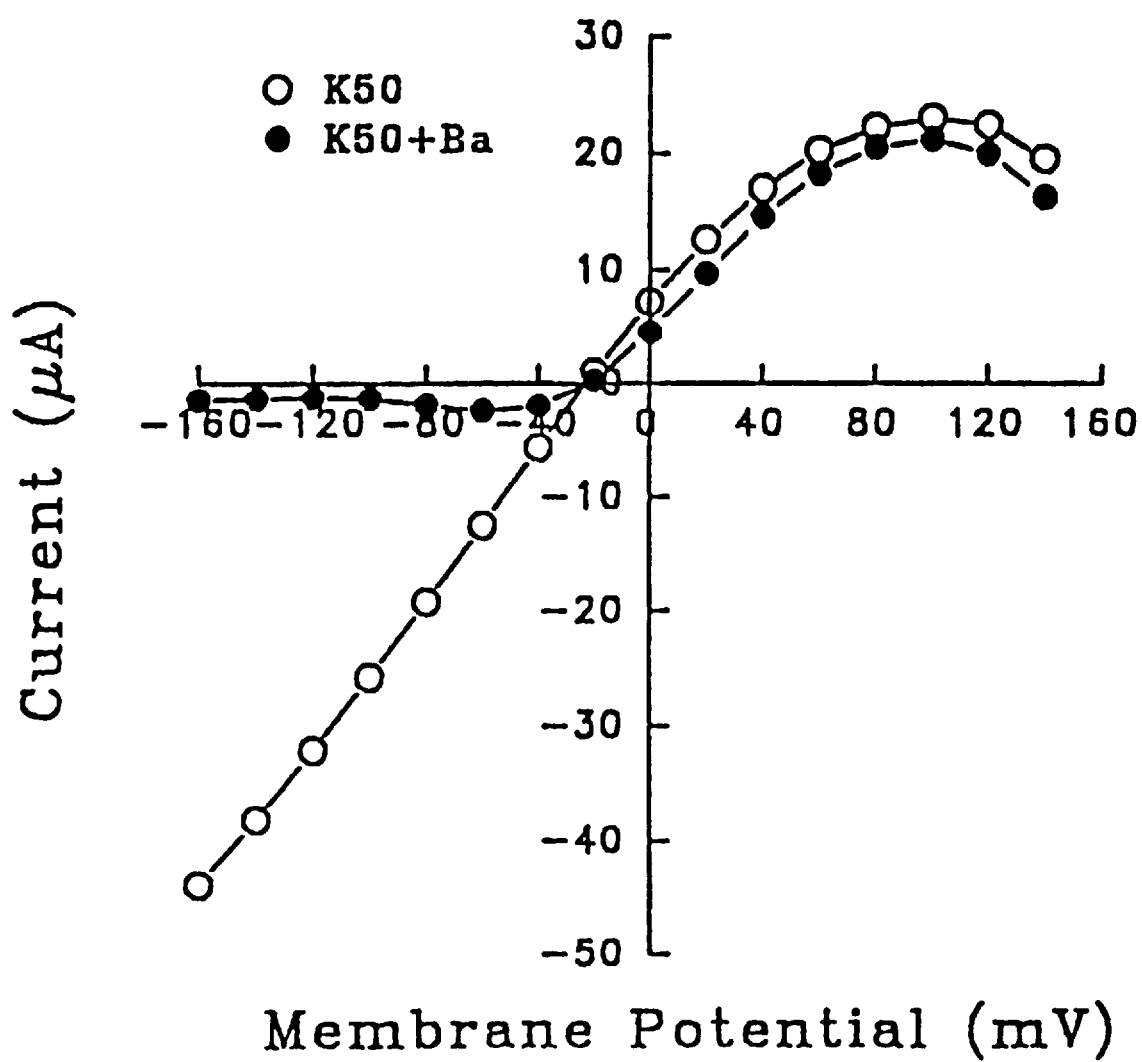
Figure 7F:
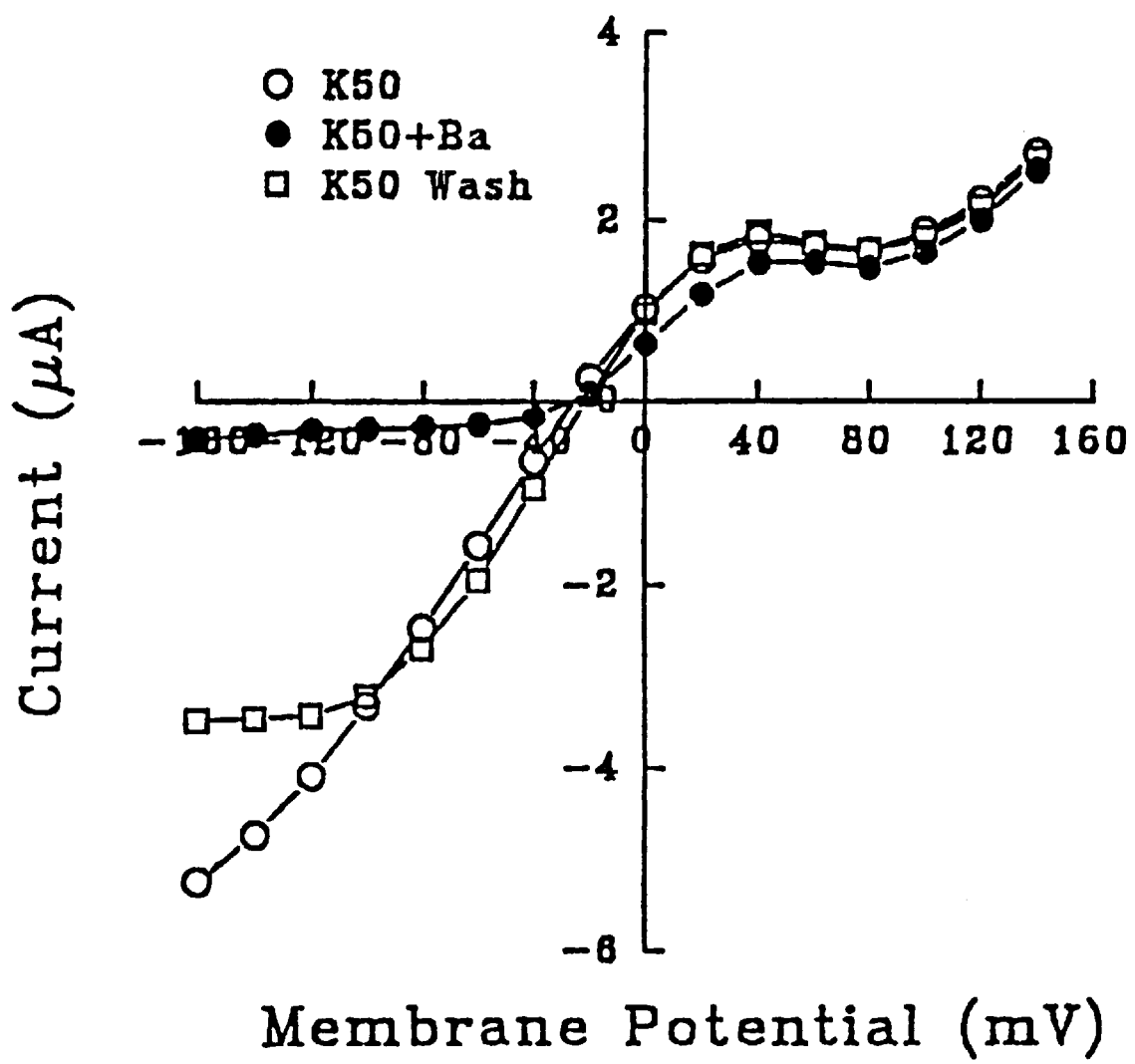

Currents were recorded by the two microelectrode voltage clamp technique using oocytes expressing K-8, K11 or K26 cRNAs and the results are shown in FIGS. 7A–F. FIGS. 7A, 7B and 7C show typical current traces recorded in 50 mM external K$^+$ from oocytes injected with K-8, K11 or K26, respectively. In FIGS. 7D, 7E and 7F the Y axis is current in micro amperes, the X axis is membrane potential in milli-Volts. The corresponding I–V relationships are depicted as open circles (○) in FIGS. 7D, 7E and 7F. In all cases, currents at potentials positive to the holding potential of −20 were directed outward and those at potentials negative to −20 mV were directed inward. The amplitude of the inward currents are consistently greater than that of the outward current, thus creating inward rectification.

The current activation time course of these cloned channels are similar, with two distinct phases: a rapid, almost instantaneous phase followed by a slower, time dependent phase. Once activated, the current does not decline or inactivate in either direction. Application of 1 mM Ba$^{2+}$ selectively blocks the inward current, in a time and voltage dependent manner that is most prominent on K-8 (FIGS. 7D, 7E and 7F, filled circles (●)). The Ba$^{2+}$ block was reversed following washout (FIGS. 7D, 7E and 7F, open squares (□). The lack of effect of Ba$^{2+}$ on the outward current may suggest a "knock-off" effect of the Ba$^{2+}$ from its channel binding site by the competing K$^+$ ions that are moving outward.

Figure 8A:
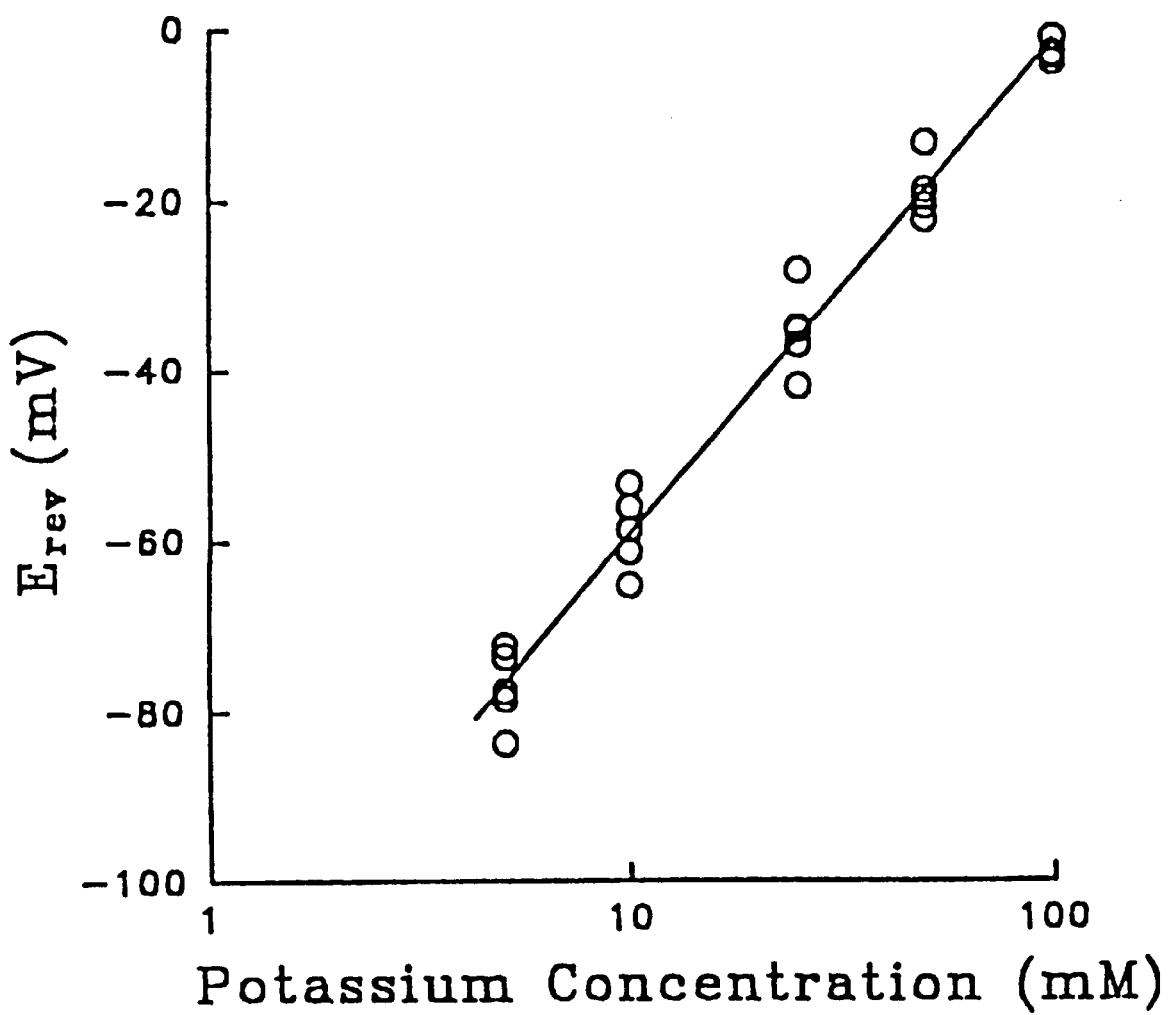
FIGS. 8A–8F. Potassium selectivity of the K-8, K11 and K26 channels expressed in Xenopus oocytes.
Figure 8B:
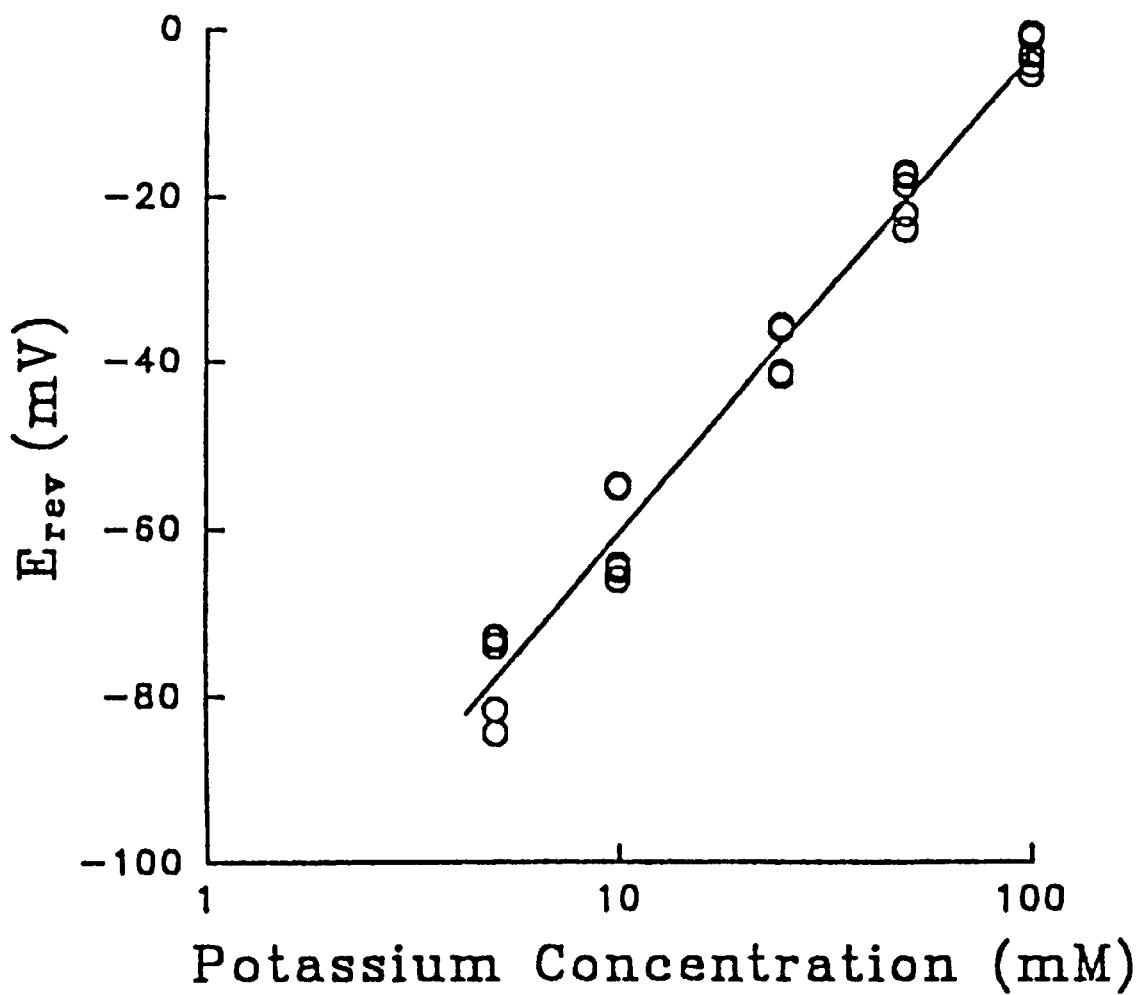
Figure 8C:
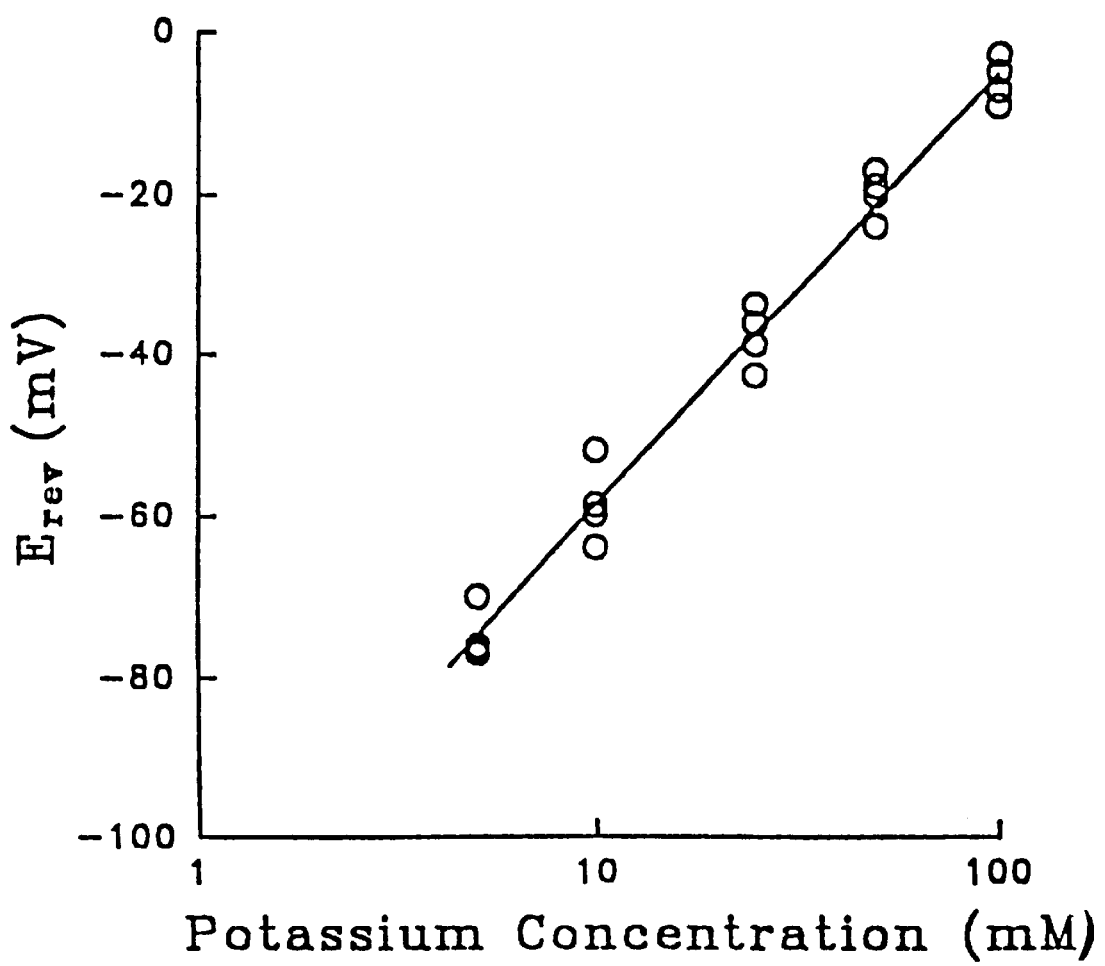

To examine the K$^+$ selectivity of the channels, external KCl concentrations were increased from 5 mM to 100 mM and choline Cl was substituted to maintain the osmolarity. The results shown in FIGS. 8A–8F illustrate the relationship between reversal potential ($E_{rev}$) and external K$^+$ concentrations for K-8, K11 or K26 (FIGS. 8A, 8B and 8C, respectively). In FIGS. 8A–8C the Y axis is reversal potential ($E_{rev}$) in milliVolts and the X axis is Potassium Concentration in milliMolar. The data were fitted to the Nernst relationship and yielded a slope per decade change of K$^+$ concentrations of 57.87 mV for K-8, 57.45 mV for K11 and 53.53 mV for K26, all within the theoretical value of the 58 mV for K$^+$ selective electrodes at room temperature.

Figure 8D:
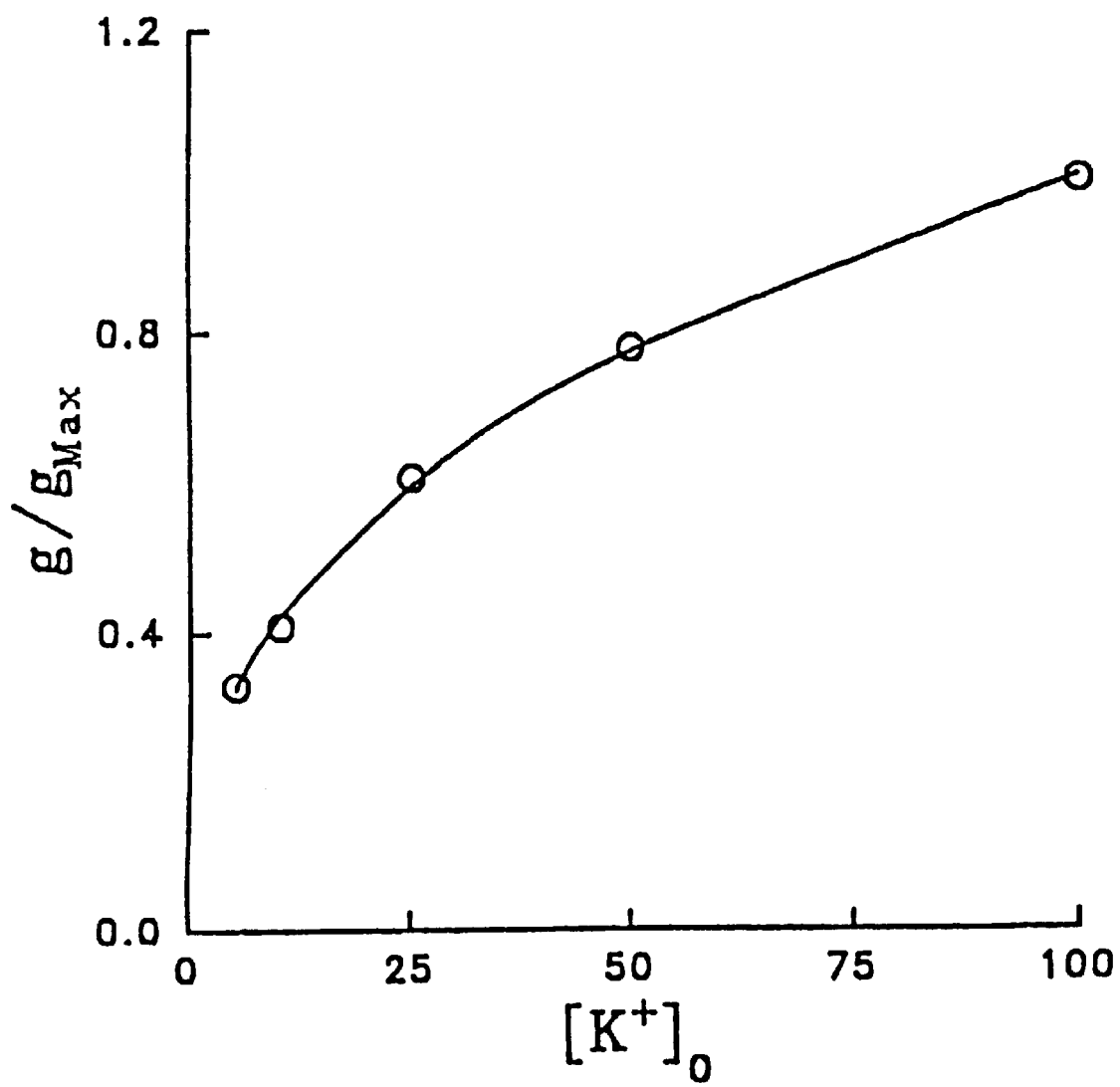
Figure 8E:
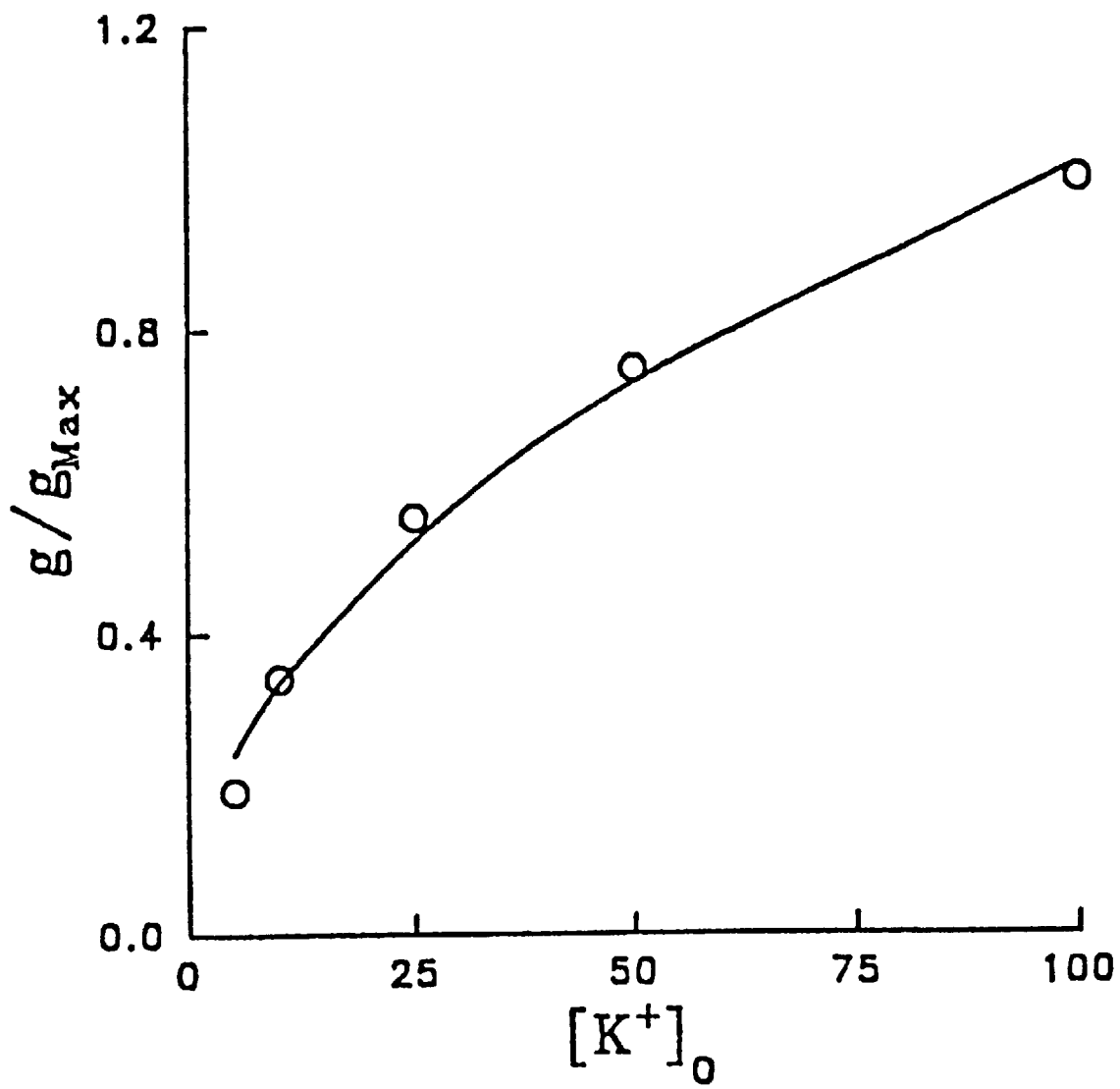
Figure 8F:
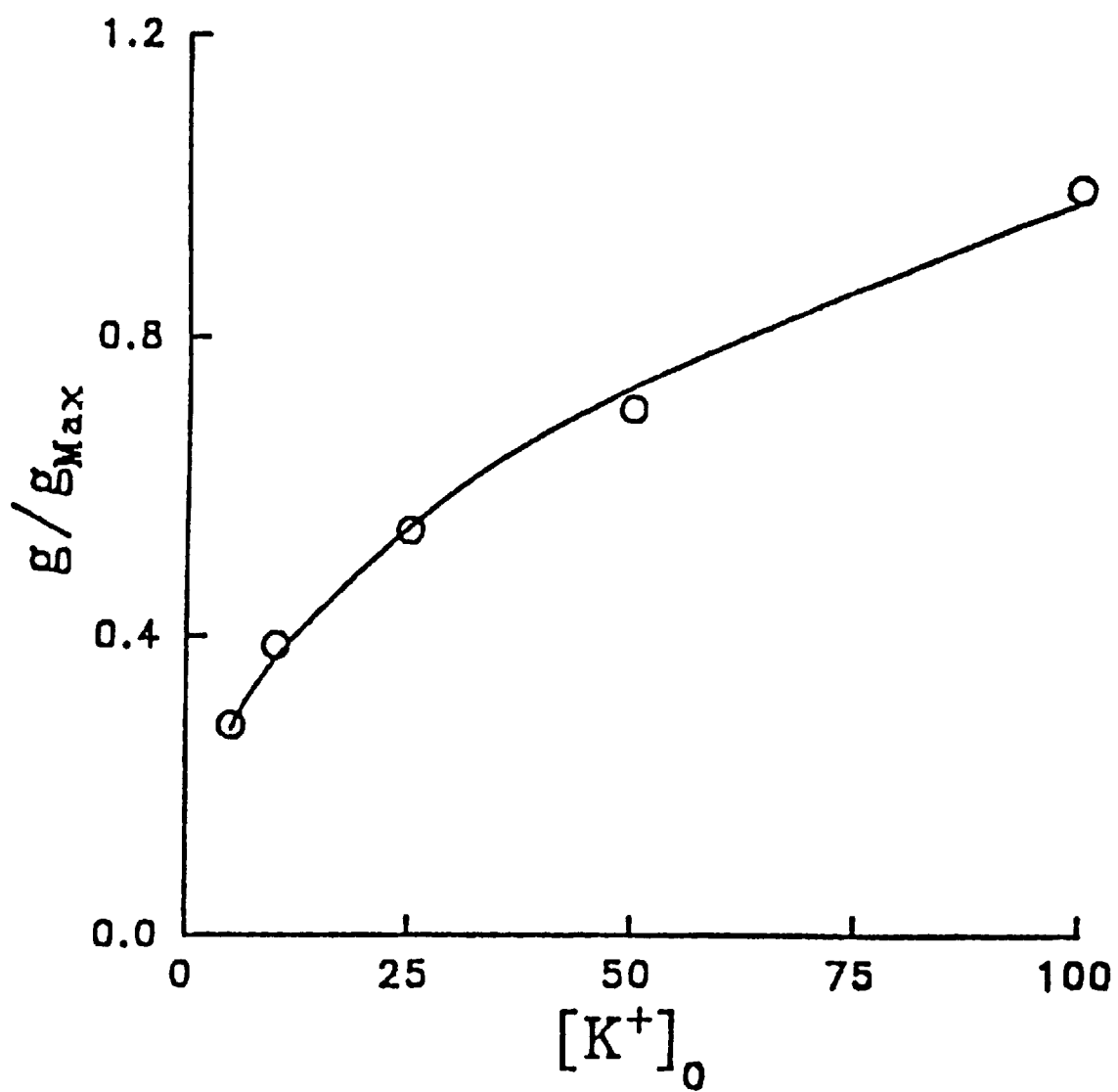

The membrane conductance, $g_k$, of the inward rectifying potassium channel increases as [K$^+$]$_o$ is raised. The relationship between membrane conductance, $g_k$, and [K$^+$]$_o$ is given by $$g_k = C[K^{30}]_o^Z$$

where C is a proportion factor, [K$^+$]$_o$ is external K$^+$ concentration in mM and Z, the exponent factor. We measured the slope conductance of these channels in solutions containing (in mM) 5, 10, 25, 50 and 100 KCl and the results are shown in FIGS. 8D, 8E and 8F, respectively for K-8, K11 and K26. In FIGS. 8D, 8E and 8F, the Y axis is $g/g_{max}$, the X axis is [K$^+$]$_o$. The relationship of channel conductance with external [K$^+$] is non-linear, declining at higher [K$^+$]. The average values of Z for K-8, K11 and K26 are 0.39±0.05 (n=5), 0.383±0.097 (n=5) and 0.488–0.01 (n=4) respectively. These results further support the conclusion that the K$^+$ ion permeations through the inward rectifying channels deviate from the independence principle and this means that ion-ion interactions in the channel are taking place.

4. Optical measurement of channel activity in mammalian cells.

We also examined the functional expression K26 by both transient and stable transfection of mammalian cell. Initially, functional expression of K26 K$^+$ channel expression was determined using a voltage-sensitive dye and an instrument to record changes in cellular fluorescence. The dye of choice is bis(1,3-dibutylbarbituric acic)trimenthine oxonol) DiBAC$_4$(3). Other voltage sensitive dyes could also be used. To optically measure changes in membrane potential, cells were subcultured onto coverglass chambers and grown to confluence. Immediately prior to analysis, cells were washed several times with Earle's balanced salt solutions that was buffered to pH 7.4 with 20 mM Hepes (EBSS-H) and then placed in the same buffer containing 5 µM Dibac$_4$(3). Fluorescent imaging of membrane potential was carried out after the cells were equilibrated with 5 µM Dibac$_4$(3) for 15 min at 37° C. and then placed in a 35° C. temperature-regulated mini-incubator that was mounted on the stage of a laser-based imaging cytometer (ACAS 570, Meridian Instruments). The ACAS 570 was configured to excite the cells at 488 nm using an argon ion laser. The fluorescent emission was collected at 535 nm using a 495 nm LP dichroic mirror and a 10 nm band pass filter centered at 525 nm. In all cases, data was collected every 60 seconds for at least 25 minutes using the Kinetic program within the ACAS software. Changes in fluorescence were computed using a logistical model developed at Upjohn Laboratories. Control experiments established that the addition of solvents such as dimethylsulfoxide and ethanol had no effect at concentration up to 0.8% (v/v). Previous studies by Epps et. al. (Chemistry and Physics of Lipids, in press 1994) and Holevinsky et al. (J. Membrane Biology, in press 1994) established that there is a linear relation between changes in fluorescence and changes in membrane potential indicating that the optical membrane potential assay is quantitative. Other imaging instruments and/or spectrofluorometers could also be used to optically measure changes in membrane potential.

Figure 9:
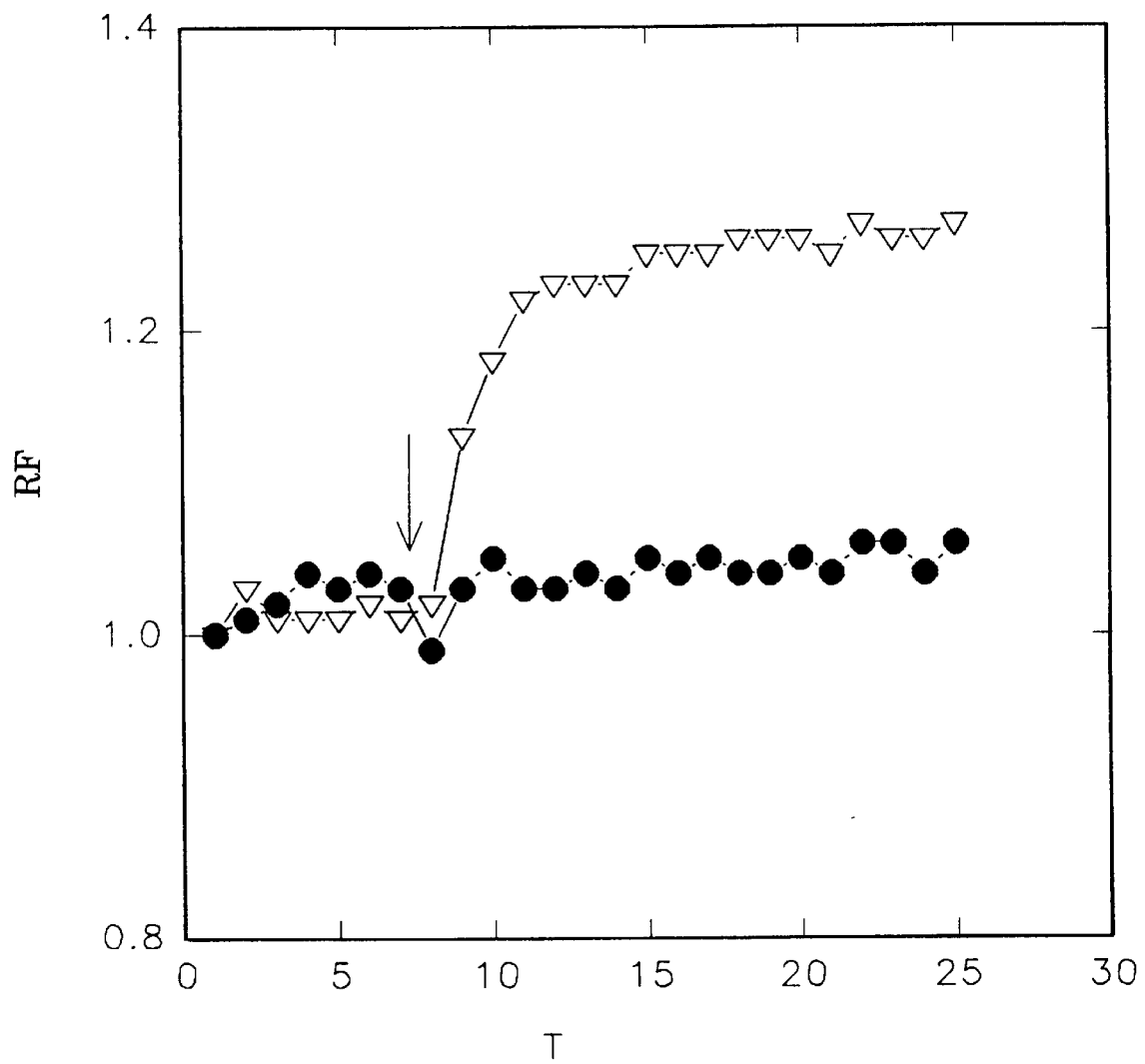
FIG. 9. $BaCl_2$-induced depolarization of COS 7 cells that are transiently expressing the K26 $K^X$ channel analyzed on the ACAS cytometer.
Figure 10:
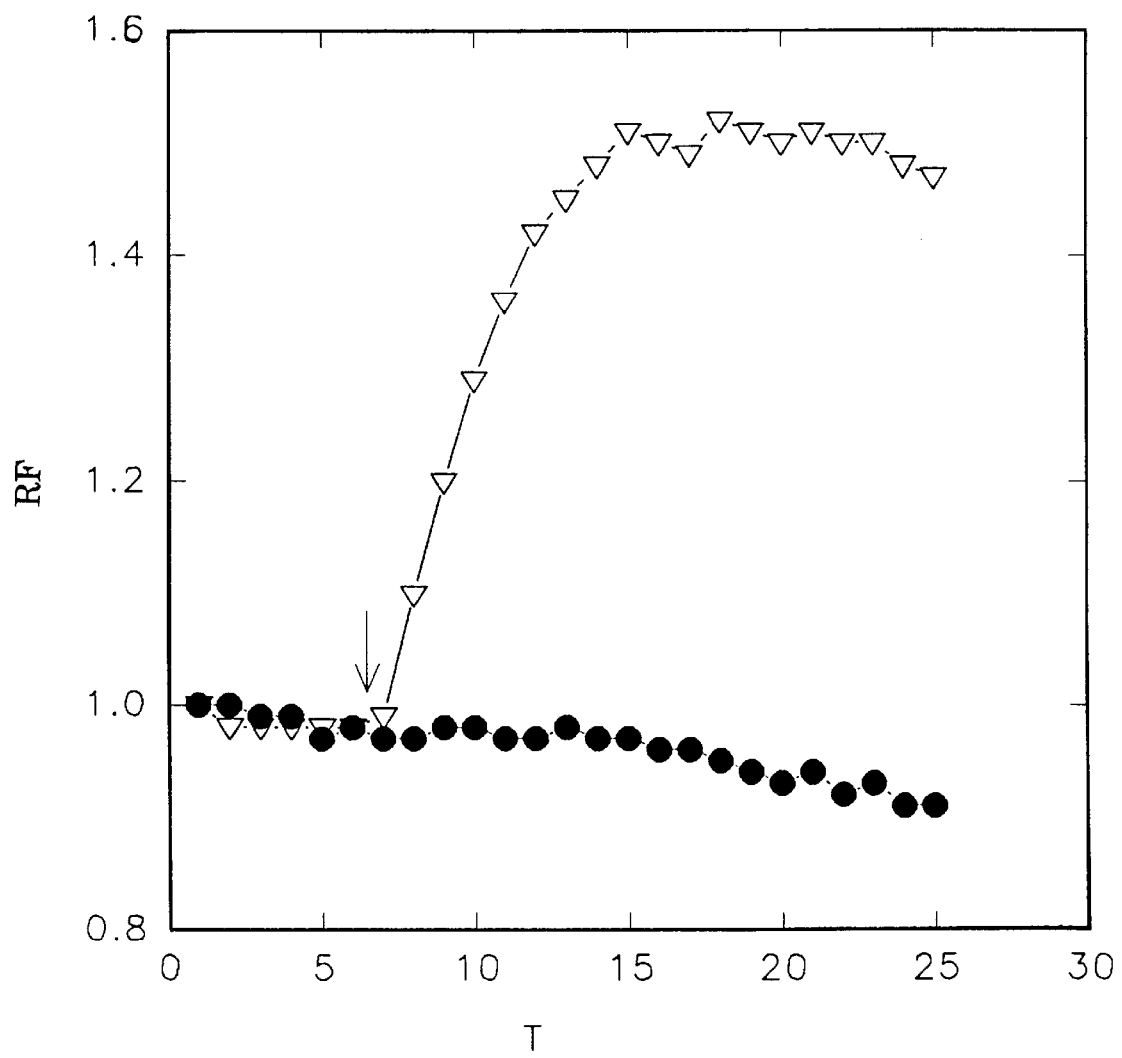
FIG. 10. $BaCl_2$-induced depolarization of human embryonic kidney (HEK 293) cells that are stably expressing the K26 $K^X$ channel analyzed on the ACAS cytometer.

In the case of K26, the data in Section III (3), indicated that the heterologously expressed K26 K$^+$ channel has a very high open probability. These data predicted that if K$^+$ channel blocker is added to cells that express the K26 K$^+$ channel, then the membrane potential of the cells expressing the channel should be depolarized. The data in FIG. 9 confirmed this prediction. In FIGS. 9–12B the Y axis, labeled RF, is Relative Fluorescence and the X axis, labeled T, is Time, in minutes (min). When compounds, such as glyburide or glipizide (e.g. FIGS. 12A and 12B) are added to the cell solutions, the additions are always made at Time equals seven (7) minutes. The data in FIG. 9 establish that when 1 mM Ba$^{++}$ is added to COS 7 cells (arrow; FIG. 9) that are transiently expressing the K26 K$^+$ channel (open triangles; FIG. 9), the membrane potential is depolarized. Previous studies by Ho et. al. established that Ba$^{++}$ blocks the K26 class of inwardly rectifying K$^+$ channels. When 1 mM BaCl$_2$ is added to wild type COS 7 cells (arrow; FIG. 9), there is little effect on the membrane potential (solid circles; FIG. 9). These data indicate that wild type COS 7 cells do not express Ba$^{++}$-sensitive ion channels, thus making them good recipients cells for K$^+$ channel expression studies. The K26 K$^+$ channel can also be stably expressed in mammalian cells. As indicated by the data in FIG. 10 when 3 mM BaCl$_2$ (arrow; FIG. 10) was added to HEK 293 cells that were transfected with K26 cDNA (open triangles; FIG. 10) the membrane potential was depolarized. In this experiment, the HEK 293 cells expressing K26 were passaged 16 times, indicating that K26 stably expressed. When 3 mM BaCl$_2$ (arrow; FIG. 10) to wild type HEK 293 cells (solid circles; FIG. 10) there was no effect on the membrane potential. Electrophysiological studies confirm the conclusions from the optical membrane potential assay. Taken together, these data indicate that the optical membrane potential assay can be used to find new chemical entities that block K26 K$^+$ channel activity when this channel is expressed in mammalian cells.

5. Development of a high volume screen for agents that block K26 K$^+$ channel activity.

We have developed a high volume screen to find new chemical entities that block the K26 K$^+$ channel activity. The key features of the screen are to use the optical membrane potential assay described in Section III (4), to find new chemical entities that depolarizes COS 7 or HEK 293 cells that express K26 or related potassium channel proteins. Note that it might be that the BEST K$^+$ channel protein to use in a screen would be the K11 protein because of its sensitivity to ATP, see Experimental Details, Section I, Part 7. Selection of the clone and selected derivatives. It is anticipated that all of the disclosed clones and obvious variants of the initial 30 or so amino acids or so would be used to screen for K$^+$ channel blockers. To be selective, the agents that depolarize cells expressing the K26 (or K11 etc.) K$^+$ channel should have little to no effect on wild type cells or mock transfected control cells. Conversely, if a new chemical entity is found that depolarizes both COS 7 and HEK 293 cells whether or not they express the K26 (or K11 etc.) K$^+$ channel, then it will be concluded that this new chemical entity has no selectivity for K26 (or K11 etc.). Thus, selectivity of K$^+$blockade will be judged by a pairwise comparison of the same cell type that is either expressing or not expressing K26 (or K11 etc.). In this way, a nonspecific measure of a change in membrane potential can be used to find new chemical entities that selectively block K26 (or K11 etc.) K$^+$ activity.

Figure 11:
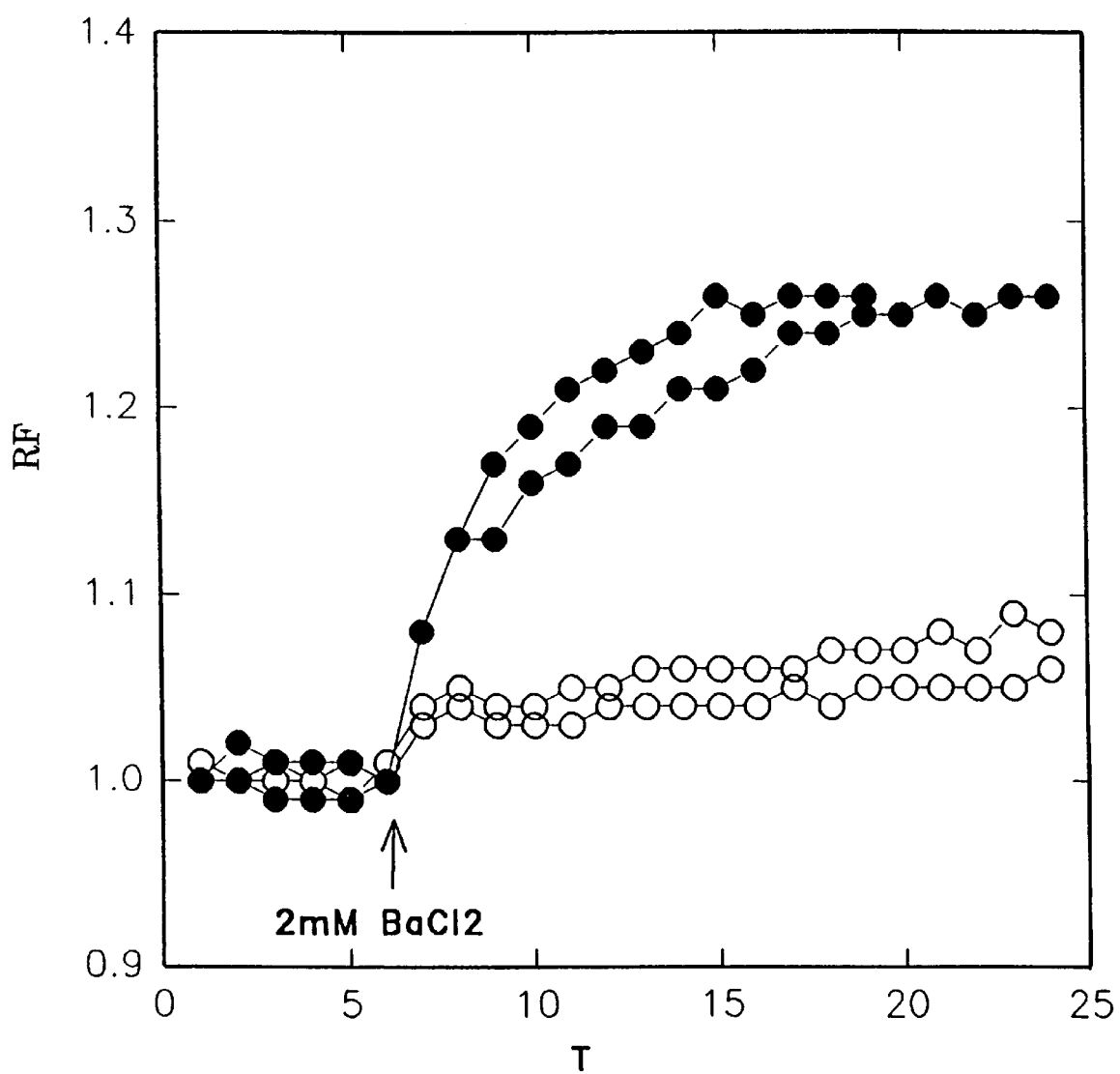
FIG. 11. $BaCl_2$-induced depolarization of COS 7 cells that are transiently expressing the ROMK1 $K^X$ channel analyzed on the ACAS cytometer.
Figure 12A:
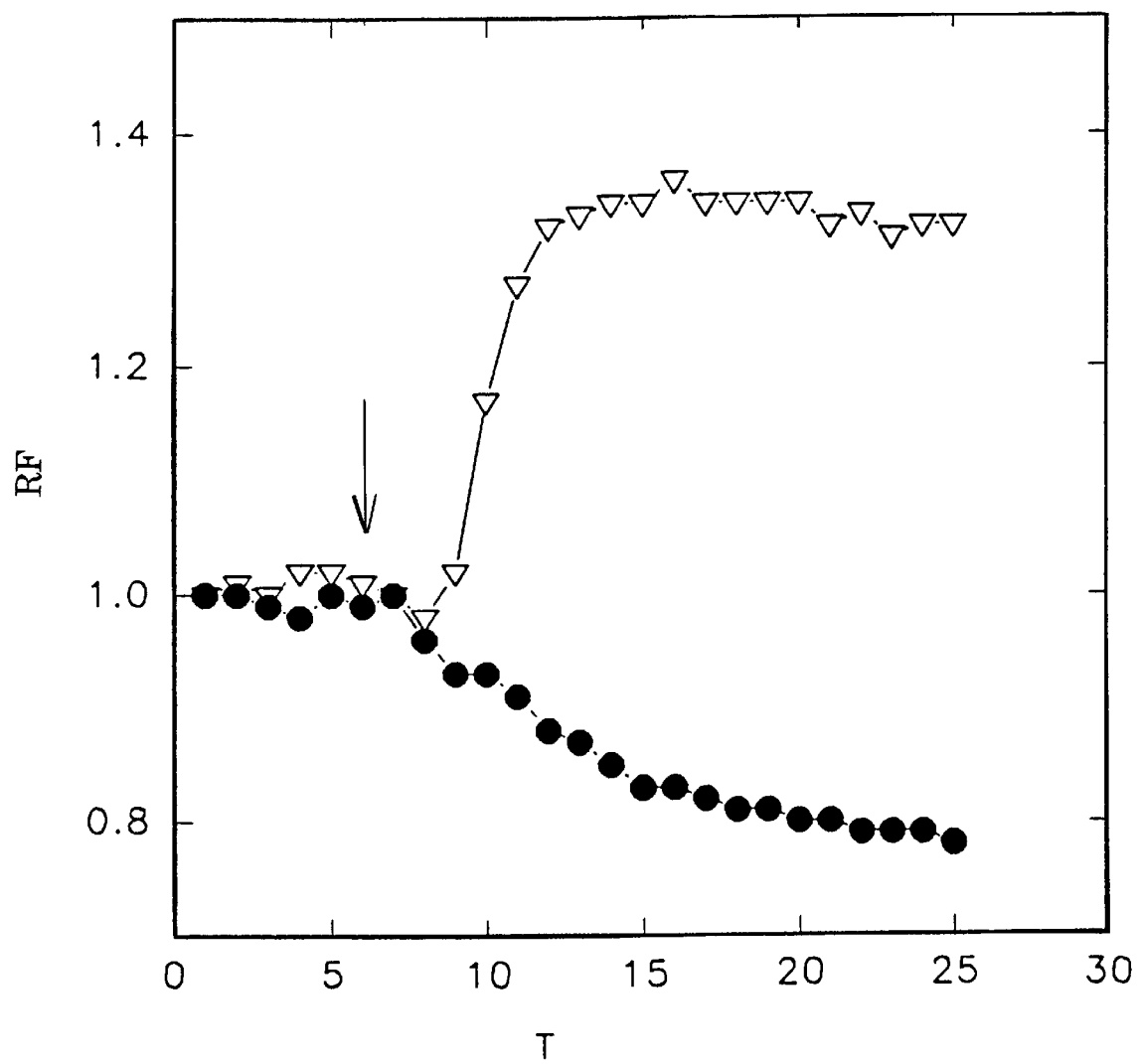
FIGS. 12(A–B). Glyburide-induced depolarization of COS 7 cells that are stably expressing the ROMK1 $K^X$ channel analyzed on the ACAS cytometer.
Figure 12B:
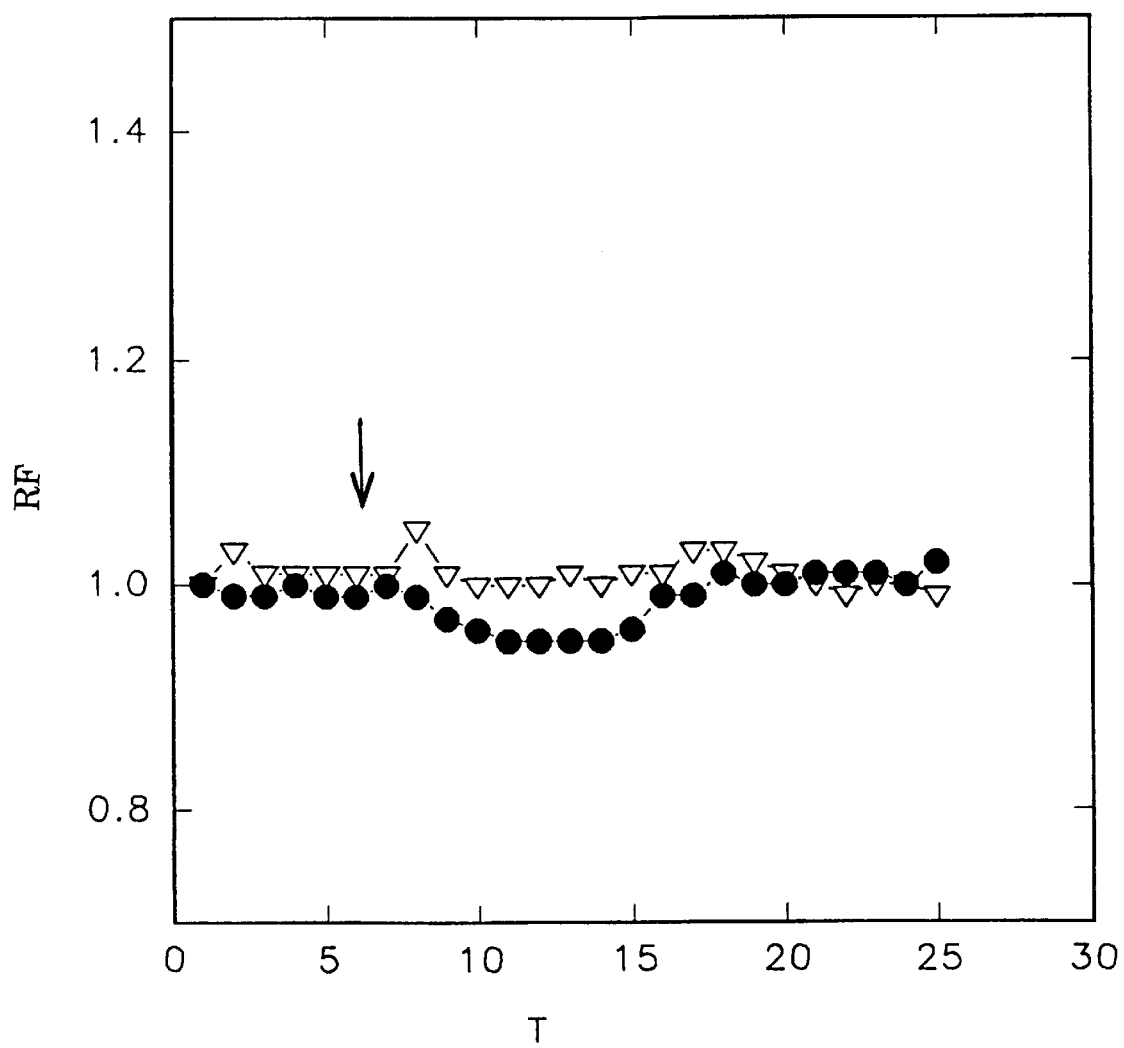

Operation of the screen. The data in FIG. 11 shows that when the ROMK1 K$^+$ channel is transiently expressed in COS cells (solid circles; FIG. 11) the addition of 2 mM BaCl$_2$ (arrow; FIG. 11) causes the membrane potential to depolarize. The addition of 2 mM BaCl$_2$ (arrow; FIG. 11) has little effect on wild type COS 7 cells (open circles; FIG. 11). These data indicate that both the ROMK1 and the K26 K$^+$ channel are sensitive to Ba$^{++}$. Furthermore, we have found that the addition of 100 μM glyburide (arrow; FIG. 12A), a sulfonylurea that is known to block K$_{ATP}$ channels, causes COS 7 cells that are stably expressing the ROMK1 K$^+$ (open triangles, FIG. 12A) to be depolarized. The addition of 100, μM glyburide to wild type COS 7 (solid circles; FIG. 12A) produced a hyperpolarization. These data indicate that glyburide is blocking the ROMK1 channel expressed in COS 7 cells. To determine pharmacological selectivity we also examined the effect of other sulfonylureas that are closely related to glyburide. The data in FIG. 12B indicate that the addition of 100 μM glipizide (arrow; FIG. 12B) had no effect on the membrane potential of COS 7 cells expressing the ROMK1 K$^+$ channel (solid circles; FIG. 12B). In addition, 100 μM glipizide (arrow; FIG. 12B) had no effect on the membrane potential of wild type COS 7 cells (open triangle: FIG. 12B). Taken together these data illustrate that the optical membrane potential assay can find compounds in a chemical series that specifically interact with heterologously expressed K$^+$ channels.

Figure 13B:
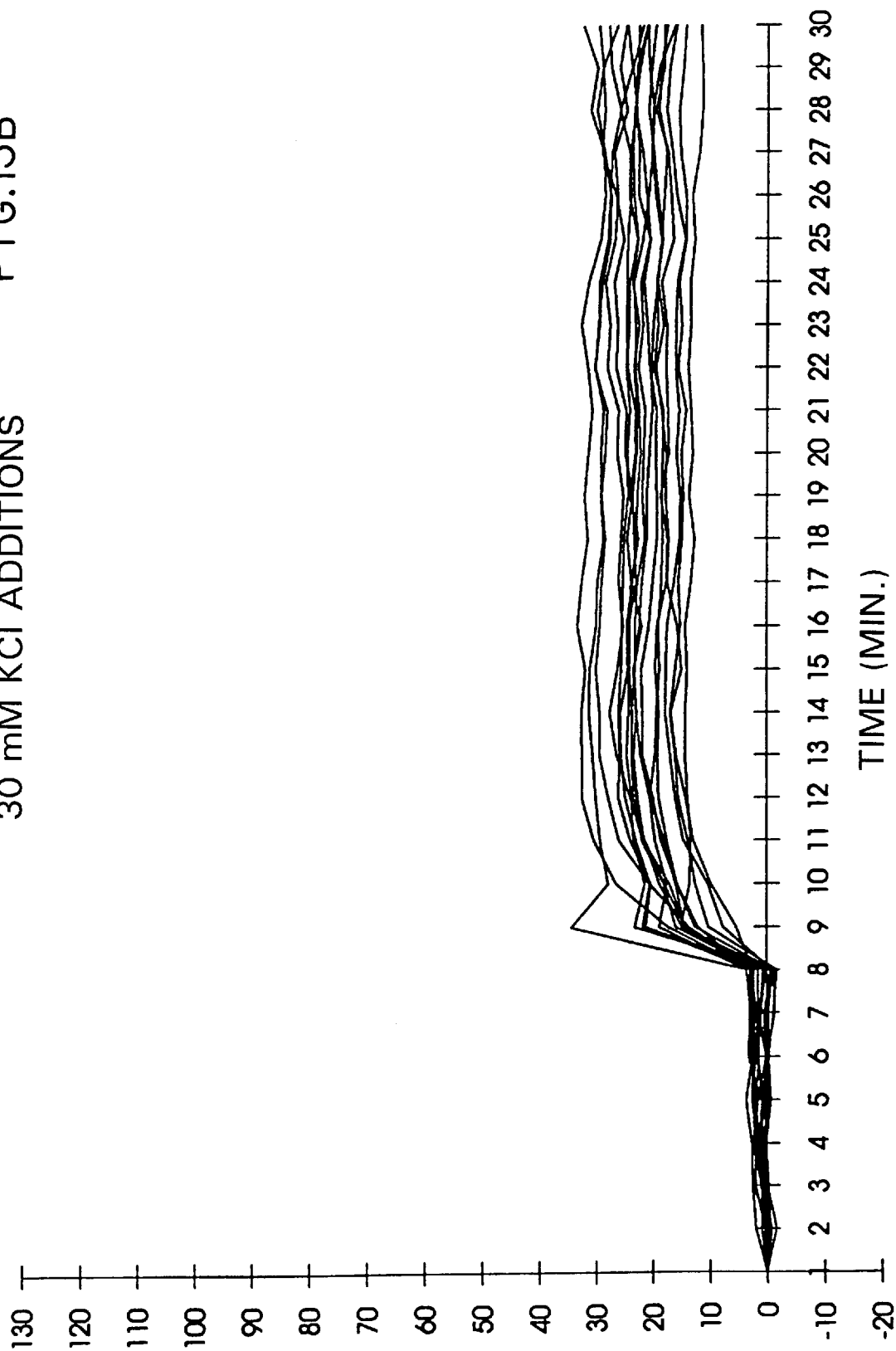

To rapidly screen for new chemical entities that selectivity block K26 or (K11) K$^+$ activity we utilized a newly developed 96 well fluorescent imaging plate reader called FLIPR (NovelTech, Ann Arbor, Mich.). This instrument can simultaneously, optically, measure changes in the membrane potential of cells in each well of a 96 well microtest plate. See FIG. 13A. When a solvent control is added to A10 smooth muscle cells (min 7; FIG. 13A) there is little effect on the membrane potential (all lines in FIG. 13A). (A10 smooth muscle cells are available from the American Type Tissue Collection, ATCC number CRL-1476.) The Y axis of FIGS. 13A, 13B, and 13C, not labeled in the Figure, shows the Percent of Maximal Response, the X axis shows the Time (T) in minutes (min). When 3 mM KCl is added to A10 smooth muscle cells (min 7; FIG. 13B) that are grown in 5 mM KCl, there is a small but statistically significant change in the membrane potential (all lines in FIG. 13B). When 30 mM KCl is added to A10 smooth muscle cells (min 7; FIG. 13C) there is large change in the membrane potential (all lines FIG. 13C).

The data clearly shows that the optical membrane potential assay can be used to detect agents that alter the membrane potential of cells. The optimal screening strategy is to use the optical membrane potential assay and FLIPR to find new chemical entities that block the activity of the K26 (or K11) K$^+$ channel expressed in COS and HEK 293. In summary, the screen may operate according to the following steps:

1) Cells expressing the cloned K26 (or K11) K$^+$ channel are grown to confluence in a 96 well microtest plate. 2) Cells are equilibrated with 5 μM DiBAC$_4$(3) in Earle's balanced salt solution containing 20 mM HEPES. 3) Baseline measurements of each well are recorded. 4) One test compound or a cocktail of test compounds are added to each well and changes in membrane potential are recorded. 5) Compounds that depolarize cells expressing K26 are then tested on wild type or mock transfected controls to establish selectivity. 6) Compounds that are shown to selectively block K26 will be tested for diuretic efficacy in animal models.

Over 5000 compounds per month can be analyzed with this screening protocol.

We claim:

1. An isolated nucleic acid molecule encoding a human kidney potassium channel protein where the DNA molecule comprises a sequence of SEQ. ID. NO. 6, SEQ. ID. NO. 7, SEQ. ID. NO. 8, SEQ. ID. NO. 9, or SEQ. ID. NO. 10.

2. The nucleic acid molecule of claim 1, comprising the DNA of SEQ. ID. NO. 6.

3. The nucleic acid molecule of claim 1, comprising the DNA of SEQ. ID. NO. 7.

4. The nucleic acid molecule of claim 1, comprising the DNA of SEQ. ID. NO. 8.

5. The nucleic acid molecule of claim 1, comprising the DNA of SEQ. ID. NO.9.

6. The nucleic acid molecule of claim 1, comprising the DNA of SEQ. ID. NO. 10.

7. An isolate cDNA sequence comprising the sequence of SEQ. ID. No. 1.

8. An isolated cDNA sequence comprising the sequence of SEQ. ID. No. 2.

9. An isolated cDNA sequence comprising the sequence of SEQ. ID. No. 3.

10. An isolated cDNA sequence comprising the sequence of SEQ. ID. No. 4.

11. An isolated cDNA sequence comprising the sequence of SEQ. ID. No. 5.

12. An isolated cDNA sequence consisting of the sequence of SEQ. ID. No. 6.

13. An isolated cDNA sequence consisting of the sequence of SEQ. ID. No. 7.

14. An isolated cDNA sequence consisting of the sequence of SEQ. ID. No. 8.

15. An isolated cDNA sequence consisting of the sequence of SEQ. ID. No. 9.

16. An isolated cDNA sequence consisting of the sequence of SEQ. ID. No. 10.

17. A plasmid comprising the nucleic acid molecule of claim 1, wherein said nucleic acid molecule is a cDNA molecule, adapted for expression in a mammalian cell.

18. A plasmid of claim 17, where the DNA molecule comprises SEQ. ID. NO. 6.

19. A plasmid of claim 17, where the DNA molecule comprises SEQ. ID. NO. 7.

20. A plasmid of claim 17, where the DNA molecule comprises SEQ. ID. NO. 8.

21. A plasmid of claim 17, where the DNA molecule comprises SEQ. ID. NO. 9.

22. A plasmid of claim 17, where the DNA molecule comprises SEQ. ID. NO. 10.

23. An isolated mammalian cell culture or cell line containing the plasmid of claim 17.

24. An isolated mammalian cell culture or cell line comprising the plasmid of claim 18.

25. An isolated mammalian cell culture or cell line comprising the plasmid of claim 19.

26. An isolated mammalian cell culture or cell line comprising the plasmid of claim 20.

27. An isolated mammalian cell culture or cell line comprising the plasmid of claim 21.

28. An isolated mammalian cell culture or cell line comprising the plasmid of claim 22.

29. A method to screen for compounds that modulate human kidney potassium channel activity, comprising, a) growing the mammalian cell culture or cell line of claim 23, b) equilibrating the cells with a balanced salt solution, c) making baseline measurements of membrane potentials of the equilibrated cells, d) adding one test compound or a cocktail of test compounds to the cells and recording changes in membrane potential, e) adding compounds identified in step d) to wild type or mock transfected control cells and recording changes in membrane potential to establish selectivity, and f) selecting the compounds that are shown to selectively modulate $K^+$ movement through the $K^+$ channel.

30. The method of screening of claim 29, where the mammalian cell culture or cell line contains the plasmid which comprises the DNA molecule comprising SEQ. ID. NO. 6.

31. The method of screening of claim 29, where the mammalian cell culture or cell line contains the plasmid which comprises the DNA molecule comprising SEQ. ID. No. 7.

32. The method of screening of claim 29, where the mammalian cell culture or cell line contains the plasmid which comprises the DNA molecule comprising SEQ. ID. NO. 8.

33. The method of screening of claim 29, where the mammalian cell culture or cell line contains the plasmid which comprises the DNA molecule comprising SEQ. ID. NO. 9.

34. The method of screening of claim 29, where the mammalian cell culture or cell line contains the plasmid which comprises the DNA molecule comprising SEQ. ID. NO. 10.

35. An isolated protein functioning in a mammalian cell as a human kidney potassium channel protein, where the protein comprises the amino acid sequence of SEQ. ID. NO.s 11, 12, or 13.

* * * * *